(12) United States Patent
Jishage et al.

(10) Patent No.: US 11,793,180 B2
(45) Date of Patent: Oct. 24, 2023

(54) GENE-MODIFIED MOUSE EXPRESSING HUMAN GPC3 POLYPEPTIDE

(71) Applicant: CHUGAI SEIYAKU KABUSHIKI KAISHA, Tokyo (JP)

(72) Inventors: Koichi Jishage, Shizuoka (JP); Hiroshi Hino, Shizuoka (JP); Takahiro Ishiguro, Tokyo (JP); Yasuko Kinoshita, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/327,218

(22) PCT Filed: Aug. 21, 2017

(86) PCT No.: PCT/JP2017/029766
§ 371 (c)(1),
(2) Date: Feb. 21, 2019

(87) PCT Pub. No.: WO2018/038046
PCT Pub. Date: Mar. 1, 2018

(65) Prior Publication Data
US 2019/0174731 A1   Jun. 13, 2019
US 2020/0229408 A9   Jul. 23, 2020

(30) Foreign Application Priority Data
Aug. 22, 2016  (JP) .................................. 2016-161777

(51) Int. Cl.
| A01K 67/027 | (2006.01) |
| C12N 15/85 | (2006.01) |
| G01N 33/50 | (2006.01) |
| C07K 16/28 | (2006.01) |
| C07K 16/30 | (2006.01) |
| C12N 5/10 | (2006.01) |
| C07K 14/705 | (2006.01) |
| A61K 39/00 | (2006.01) |

(52) U.S. Cl.
CPC ........ *A01K 67/0278* (2013.01); *C07K 14/705* (2013.01); *C07K 16/2809* (2013.01); *C07K 16/303* (2013.01); *C12N 5/10* (2013.01); *C12N 15/85* (2013.01); *G01N 33/5041* (2013.01); *G01N 33/5088* (2013.01); *A01K 2217/052* (2013.01); *A01K 2217/072* (2013.01); *A01K 2217/206* (2013.01); *A01K 2227/105* (2013.01); *A61K 2039/505* (2013.01); *C07K 2317/31* (2013.01); *C12N 2015/8518* (2013.01)

(58) Field of Classification Search
None
See application file for complete search history.

(56) References Cited

U.S. PATENT DOCUMENTS

| 2005/0064474 A1* | 3/2005 | Urnov .................... A61K 35/12 435/6.18 |
| 2005/0208489 A1* | 9/2005 | Carroll .................... C12N 9/22 435/6.16 |
| 2012/0117671 A1* | 5/2012 | Yoneyama ........... A01K 67/027 800/9 |
| 2015/0225481 A1* | 8/2015 | Jishage .............. G01N 33/6869 800/3 |
| 2015/0266966 A1 | 9/2015 | Smith et al. |
| 2018/0192623 A1 | 7/2018 | Jishage et al. |

FOREIGN PATENT DOCUMENTS

| EP | 2896291 A1 | 7/2015 | |
| JP | 2017536126 A | 12/2017 | |
| WO | WO-9937764 A2 * | 7/1999 | ......... C07K 14/4725 |
| WO | WO-03006639 A1 | 1/2003 | |
| WO | WO-2012143524 A2 | 10/2012 | |
| WO | WO-2014042251 A1 * | 3/2014 | .............. A61P 29/00 |
| WO | WO-2015095392 A1 | 6/2015 | |
| WO | WO-2016085889 A1 * | 6/2016 | ......... A01K 67/0276 |
| WO | WO 2017010423 A1 | 1/2017 | |

OTHER PUBLICATIONS

Brevini et al., Theriogenology, vol. 74, pp. 544-550 (Year: 2010).*
Paris et al. Theriogenology, vol. 74, pp. 516-524 (Year: 2010).*
Ezashi Annu. Rev. Anim. Biosci. . 4:223-53 (Year: 2016).*
Hong et al. (Stem Cells and Development,vol. 21(9), pp. 1571-1586 (Year: 2012).*
Patil et al.,Indian Journal of Public Health research & Development, vol. 2, No. 1, 106-109 (Year: 2011).*
Ramirez Nature Methods,, 5(5): 374-375 (Year: 2008).*
Christian Genetics, 757-761 (Year: 2010).*
Hauschild PNAS, 108( 29), 12013-12017 (Year: 2011).*
Liu et al Hepatology, 52, 3, 1060-1067 (Year: 2010).*
Willinger et al Trends in Immunology Jvol. 32, No. 7, 321-327). (Year: 2011).*
Feng et al FEBS Letter, , 588(2), 377-382 (Year: 2014).*
Rongvaux et al., PNAS, 108:2378-2383 (Year: 2011).*
Zhu et al Nature communication 10, 1845-1-13 (Year: 2019).*
Cano-Gauci et al The Journal of Cell Biology, vol. 146, No. 1, 255-264 (Year: 1999).*
Bettini, M. L., et al., "Membrane Association of the CD3ε Signaling Domain Is Required for Optimal T Cell Development and Function," J Immunol., 193:258-267 (2014).

(Continued)

*Primary Examiner* — Anoop K Singh
(74) *Attorney, Agent, or Firm* — Nixon & Vanderhye P.C.

(57) ABSTRACT

Genetically modified non-human animals which are deficient in expression of an endogenous GPC3 polypeptide and express a human GPC3 polypeptide at a physiologically adequate level; methods for producing the non-human animals; and methods for evaluating test substances using the non-human animals. Furthermore, methods for evaluating test substances regarding their safety, therapeutic effects on diseases, pharmacokinetics, in vivo distribution, and such, using the non-human animals as models.

4 Claims, 36 Drawing Sheets

Specification includes a Sequence Listing.

(56) References Cited

OTHER PUBLICATIONS

Billerbeck, E., et al., "Development of human CD4+FoxP3+ regulatory T cells in human stem cell factor-, granulocyte-macrophage colony-stimulating factor-, and interleukin-3-expressing NOD-SCID IL2Rγ$^{null}$ humanized mice," Blood, 117(11):3076-3086 (2011).

Brinster, R. L., et al., "Introns increase transcriptional efficiency in transgenic mice," Proc Natl Acad Sci. USA, 85:836-840 (1988).

Dejarnette, J. B., et al., "Specific requirement for CD3ε in T cell development," Proc Natl Acad Sci. USA, 95:14909-14914 (1998).

Fernandez-Malave, E., et al., "Overlapping functions of human CD3δ and mouse CD3γ in αβ T-cell development revealed in a humanized CD3γ-deficient mouse," Blood, 108:3420-3427 (2006).

Göbel, T. W. F. and Dangy, J.-P., "Evidence for a Stepwise Evolution of the CD3 Family," J Immunol., 164:879-883 (2000).

Kuhn, C., et al., "Human CD3 Transgenic Mice: Preclinical Testing of Antibodies Promoting Immune Tolerance," Sci Transl Med., 3(68):68ra10 (2011).

Liu, B., et al., "Suppression of Liver Regeneration and Hepatocyte Proliferation in Hepatocyte-Targeted Glypican 3 Transgenic Mice," Hepatology 52:1060-1067 (2010).

Malissen, M., et al., "Altered T cell development in mice with a targeted mutation of the CD3-ε gene," The EMBO Journal, 14(19):4641-4653 (1995).

Pan, Q., et al., "Different role for mouse and human CD3δ/ε heterodimer in preT cell receptor (preTCR) function: Human CD3δ/ε heterodimer restores the defective preTCR function in CD3γ- and CD3δ-deficient mice," Mol Immunol., 43:1741-1750 (2006).

Rongvaux, A., et al., "Development and function of human innate immune cells in a humanized mouse model," Nature Biotechnol., 32(4):364-372 (2014).

Ryan, K. and Bauer, D. L. V., "Finishing touches: Post-translational modification of protein factors involved in mammalian pre-mRNA 3' end formation," Intl J Biochem Cell Biol., 40:2384-2396 (2008).

Vlasova, I. A. and Bohjanen, P. R., "Posttranscriptional regulation of gene networks by GU-rich elements and CELF proteins," RNA Biol., 5(4):201-207 (2008).

Von Roretz, C. and Gallouzi, I.-E., "Decoding ARE-mediated decay: is microRNA part of the equation?" J Cell Biol., 181(2):189-194 (2008).

Wang, R., et al., "A block in both early T lymphocyte and natural killer cell development in transgenic mice with high-copy numbers of the human CD3E gene," Proc Natl Acad Sci. USA, 91:9402-9406 (1994).

Wang, N., et al., "Expression of a CD3ε transgene in CD3ε$^{null}$ mice does not restore CD3γ and δ expression but efficiently rescues T cell development from a subpopulation of prothymocytes," Intl Immunol., 10(12):1777-1788 (1998).

Weidle, U. H., et al., "Tumor-Antigen-Binding Bispecific Antibodies for Cancer Treatment," Seminars in Oncology, 41(5):653-660 (2014).

Willinger, T., et al., "Human IL-3/GM-CSF knock-in mice support human alveolar macrophage development and human immune responses in the lung," PNAS, 108(6):2390-2395 (2011).

Xu, C., et al., "Regulation of T Cell Receptor Activation by Dynamic Membrane Binding of the CD3ε Cytoplasmic Tyrosine-Based Motif," Cell, 135:702-713 (2008).

Feng, M., et al., "Therapeutically targeting glypican-3 via a conformation-specific single-domain antibody in hepatocellular carcinoma," PNAS, 110(12):E1083-E1091 (2013).

Feng, M. and Ho, M., "Glypican-3 antibodies: a new therapeutic target for liver cancer," FEBS Lett., 588(2):377-382 (2014).

Lute, K. D., et al., "Human CTLA4 knock-in mice unravel the quantitative link between tumor immunity and autoimmunity induced by anti-CTLA-4 antibodies," Blood, 106(9):3127-3133 (2005).

U.S. Patent Publication No. US 20180192623 A1 (U.S. Appl. No. 15/743,248, 371(c) date Jan. 9, 2018, Jishage, K., et al.).

Brevini, T. A. L., et al., "No shortcuts to pig embryonic stem cells," Theriogenology, 74:544-550 (2010).

Buehr, M., et al., "Capture of Authentic Embryonic Stem Cells from Rat Blastocysts," Cell, 135:1287-1298 (2008).

Ezashi, T., et al., "Pluripotent Stem Cells from Domesticated Mammals," Annu Rev Anim Biosci., 4:223-253 (2016).

Hong, J., et al., "Derivation and Characterization of Embryonic Stem Cells Lines Derived from Transgenic Fischer 344 and Dark Agouti Rats," Stem Cells Dev., 21(9):1571-1586 (2012).

Li, P., et al., "Germline Competent Embryonic Stem Cells Derived from Rat Blastocysts," Cell, 135(7):1299-1310 (2008).

Munoz, M., et al., "Constraints to Progress in Embryonic Stem Cells from Domestic Species," Stem Cell Rev Rep., 5:6-9 (2009).

Paris, D. B. B. P. and Stout, T. A. E., "Equine embryos and embryonic stem cells: Defining reliable markers of pluripotency," Theriogenology, 74:516-524 (2010).

Tong, C., et al., "Production of p53 gene knockout rats by homologous recombination in embryonic stem cells," Nature, 467(7312):211-213 (2010).

\* cited by examiner

A

B

GENE-MODIFIED MOUSE EXPRESSING HUMAN GPC3 POLYPEPTIDE

CROSS-REFERENCE TO RELATED APPLICATIONS

This application is a U.S. National Phase of PCT Application No. PCT/JP2017/029766, filed Aug. 21, 2017, which claims the benefit of Japanese Patent Application No. 2016-161777, filed Aug. 22, 2016, each of which is incorporated herein by reference in its entirety.

TECHNICAL FIELD

The present invention relates to genetically modified non-human animals expressing a human GPC3 polypeptide and methods for evaluating compounds by using the genetically modified non-human animals expressing the human GPC3 polypeptide.

BACKGROUND ART

Recently, many therapeutic agents with high specificity to molecular targets, such as therapeutic antibodies, have been developed, and to appropriately carry out preclinical evaluation on them, there is an increasing demand for humanized non-human animals such as humanized mice. Methods for preparing humanized mice include gene targeting methods in which a mouse gene is substituted with a human gene. So far, methods for substituting a human genomic gene for a homologous mouse gene have been reported, but the expression level of the substituting human gene is lower than the expression level of the homologous mouse gene, and the expression is difficult to be regulated (Non-patent Document 1). When a coding sequence of a full-length human gene is inserted into a target mouse gene, the transcribed mRNA will have a structure in which a termination codon (premature termination codon (PTC)) of the inserted human gene is present far upstream of the termination codon of the mouse gene, and the exon-exon junction derived from the mouse gene is present downstream of this premature termination codon. Since this structure is recognized by a nonsense mutation-mediated mRNA decay mechanism (NMD mechanism) and the mRNA undergoes decay, the desired gene expression level cannot be obtained in many cases. As measures against this, for example, there is a report of a method that inserts a sequence called hp7 to the 3' side of a DNA coding for a foreign gene to avoid decay of the foreign gene mRNA by the NMD mechanism, and thereby stably expressing the foreign gene in a mouse (Patent Document 1). Other than hp7, as one method for avoiding NMD, a polyadenylation signal is added immediately downstream of the cDNA sequence of a foreign gene, and this is inserted into a mouse. As a result, the transcribed mRNA has a structure in which a targeted gene-derived exon-exon junction is not produced downstream of the PTC, and thus NMD does not occur. In addition, examples of factors involved in mRNA stability include 3' untranslated regions (3'UTR) and splicing mechanisms. There are reports that a polyadenylation signal present in 3'UTR contributes to mRNA stability (Non-patent Document 2), and that the presence of adenine/uridine-rich elements (Non-patent Document 3) and GU-rich elements (Non-patent Document 4) contribute to protein translation regulation. Furthermore, there are reports that expression levels of genes with no introns, that is, expression levels of mRNAs that do not undergo splicing-out decrease (Non-patent Document 5). Meanwhile, as for a gene having an exon-intron structure, the genome region can be substituted with a desired genome region for insertion when the length of the gene is as short as tens of kilobases. However, when the length of the gene exceeds hundreds kilobases, substitution in the region is difficult (Non-patent Document 5). Thus, there has been no generally effective method for producing non-human animals that suppresses expression of the non-human animal endogenous gene and is capable of expressing a foreign gene at a physiologically adequate level.

Under such circumstances, there has been no non-human animal which is deficient in expression of the non-human animal endogenous GPC3 polypeptide and is capable of expressing a human GPC3 polypeptide at a physiologically adequate level, and method for production thereof had been unknown.

CITATION LIST

Non-Patent Documents

[Non-patent Document 1] Proc. Natl. Acad. Sci. U.S.A. 2011 Feb. 8; 108(6):2390-2395.
[Non-patent Document 2] Int. J. Biochem. Cell. Biol. 2008, 40(11):2384-2396.
[Non-patent Document 3] J. Cell. Biol. 2008 Apr. 21; 181(2):189-194.
[Non-patent Document 4] RNA. Biol. 2008. October-December; 5(4):201-207
[Non-patent Document 5] Proc. Natl. Acad. Sci. U.S.A. 85:836-840.

Patent Document

[Patent Document 1] WO 2014042251 A1

SUMMARY OF THE INVENTION

Problems to be Solved by the Invention

The present invention was achieved in view of the above circumstances. An objective of the present invention is to provide genetically modified non-human animals expressing a human GPC3 polypeptide, methods for producing the genetically modified non-human animals, and methods of screening for therapeutic agents for various diseases using the genetically modified non-human animals.

Means for Solving the Problems

The present inventors have carried out dedicated research on methods for producing non-human animals which are deficient in expression of the non-human animal endogenous GPC3 polypeptide and capable of expressing a human GPC3 polypeptide at a physiologically adequate level. As a result, surprisingly, use of an exon-intron structure sequence and the 3' untranslated region of the wild-type GPC3 gene of a non-human animal enabled generation of a non-human animal that expresses the human GPC3 gene at a physiologically adequate level.

Furthermore, the present inventors have discovered that the non-human animals which are deficient in expression of the non-human animal endogenous GPC3 polypeptide and capable of expressing a human GPC3 polypeptide at a physiologically adequate level show immune tolerance to human GPC3. That is, the use of the non-human animals as models enables accurate and convenient evaluation of test substances for their safety, therapeutic effects on diseases, pharmacokinetics, in vivo distribution, and such. Furthermore, by using this evaluation system, antibodies having a desired activity can be developed efficiently.

More specifically, for example, the following invention is provided:

[1] a genetically modified non-human animal, wherein the animal is deficient in expression of an endogenous GPC3 polypeptide and expresses a human GPC3 polypeptide;

[2] the genetically modified non-human animal of [1], wherein the animal expresses the human GPC3 polypeptide at a physiologically adequate level;

[3] the genetically modified non-human animal of [1] or [2], wherein a copy number of human GPC3 mRNA in total RNA is equivalent to a copy number of non-human animal GPC3 mRNA in total RNA in a wild-type non-human animal;

[4] the genetically modified non-human animal of any one of [1] to [3], wherein the mRNA copy number of human GPC3 in total RNA is equivalent to either one or both of mRNA copy number of monkey GPC3 in total RNA in a wild-type monkey and mRNA copy number of human GPC3 in total RNA in a human;

[5] the genetically modified non-human animal of any one of [1] to [4], wherein the animal shows immune tolerance to the human GPC3 polypeptide or a fragment thereof;

[6] the genetically modified non-human animal of any one of [1] to [5], wherein the non-human animal is a non-human mammal, and preferably a rodent;

[7] the genetically modified non-human animal of any one of [1] to [6], wherein the non-human animal is a mouse;

[8] a tissue or cell, which is isolated from the genetically modified non-human animal of any one of [1] to [7];

[9] the genetically modified non-human animal of any one of [1] to [7], wherein the non-human animal comprises a human GPC3 polypeptide-expressing cancer tissue or cancer cell;

[10] the genetically modified non-human animal of [9], which is for use in screening for a therapeutic agent for cancer;

[11] a DNA construct comprising a human GPC3 gene-coding DNA, wherein the DNA comprises an exon-intron structure-comprising nucleotide sequence added to the 5' side and a 3' untranslated region of the non-human animal GPC3 gene added to the 3' side;

[12] a knock-in vector, which comprises the DNA construct of [11];

[13] a method of screening for a therapeutic agent for cancer, the method comprising the steps of:
  (1) administering an antigen-binding molecule that binds to a human GPC3 polypeptide to the genetically modified non-human animal of any one of [1] to [7], [9], and [10];
  (2) measuring at least one evaluation index selected from the group consisting of cancer cell proliferation inhibitory effect, safety, pharmacokinetics, and in vivo distribution characteristics in the genetically modified non-human animal to which the test substance has been administered; and
  (3) selecting the antigen-binding molecule when it is superior in the evaluation index measured in step (2) compared to the evaluation index of a control;

[14] the screening method of [13], wherein the antigen-binding molecule is an antibody;

[15] a method for producing an antibody, wherein the method comprises obtaining information on amino acid sequences of the antibody selected by the screening method of [13] or [14], and introducing gene(s) coding for the amino acid sequences into a host cell;

[16] the method of [15], wherein the host cell is a CHO cell.

Furthermore, for example, the following invention is provided:

[17] a genetically modified non-human animal comprising a human GPC3 gene-coding DNA, wherein the DNA comprises an exon-intron structure-comprising nucleotide sequence added to the 5' side and a 3' untranslated region of the non-human animal GPC3 gene added to the 3' side, and wherein the DNA is inserted into the same reading frame as that of a non-human animal endogenous GPC3 gene;

[18] the genetically modified non-human animal of [17], wherein the DNA is a cDNA;

[19] the genetically modified non-human animal of [17] or [18], wherein the exon-intron structure-comprising nucleotide sequence is a sequence comprising a beta globin second exon sequence, intron sequence, and third exon sequence;

[20] the genetically modified non-human animal of any one of [17] to [19], wherein the beta globin is a beta globin of the non-human animal;

[21] the genetically modified non-human animal of any one of [17] to [20], wherein the 3' untranslated region of the non-human animal GPC3 gene is a region comprising a polyadenylation signal sequence;

[22] the genetically modified non-human animal of any one of [17] to [21], which shows immune tolerance to a human GPC3 polypeptide or a fragment thereof;

[23] the genetically modified non-human animal of any one of [17] to [22], wherein the non-human animal is a non-human mammal, and preferably a rodent;

[24] the genetically modified non-human animal of any one of [17] to [23], wherein the non-human animal is a mouse;

[25] a tissue or cell, which is isolated from the genetically modified non-human animal of any one of [17] to [24];

[26] the genetically modified non-human animal of any one of [17] to [24], wherein the non-human animal comprises a human GPC3 polypeptide-expressing cancer tissue or cancer cell;

[27] the genetically modified non-human animal of [26], which is for screening for a therapeutic agent for cancer.

Furthermore, for example, the following invention is provided:

[28] a DNA construct comprising a human GPC3 gene-coding DNA, wherein the DNA comprises an exon-intron structure-comprising nucleotide sequence added to the 5' side and a 3' untranslated region of the non-human animal GPC3 gene added to the 3' side;

[29] the DNA construct of [28], wherein the DNA is a cDNA;

[30] the DNA construct of [28] or [29], wherein the exon-intron structure-comprising nucleotide sequence is a sequence comprising a beta globin second exon sequence, intron sequence, and third exon sequence;

[31] the DNA construct of any one of [28] to [30], wherein the beta globin is a mouse beta globin;

[32] the DNA construct of any one of [28] to [31], wherein the 3' untranslated region of the non-human animal GPC3 gene is a region comprising a polyadenylation signal sequence;

[33] the DNA construct of any one of [28] to [32], which further comprises recombinase substrate sequences, a drug selection marker, and/or another sequence;

[34] a knock-in vector, which comprise the DNA construct of any one of [28] to [33];

[35] the knock-in vector of [34], which comprises a nucleotide sequence homologous to the 5'-side upstream region of a non-human animal GPC3 gene target region at the 5' side of the DNA construct, and a nucleotide sequence homologous to the 3'-side downstream region of the non-human animal GPC3 gene target region at the 3' side of the DNA construct;

[36] a non-human animal cell, wherein the knock-in vector of [35] has been introduced;

[37] the non-human animal cell of [36], wherein the cell is an embryonic stem cell (ES cell), an induced pluripotent stem cell (iPS cell), a germline stem cell, or a fertilized egg.

Furthermore, for example, the following invention is provided:

[38] a method for evaluating therapeutic effects of a test substance on cancer, the method comprising the steps of:
  (1) administering a test substance to the genetically modified non-human animal of any one of [1] to [7], [9], [10], [17] to [24], [26], and [27] wherein the animal comprises a human GPC3 polypeptide-expressing cancer tissue or cancer cell;
  (2) measuring a cancer cell proliferation inhibitory effect in the genetically modified non-human animal to which the test substance was administered; and
  (3) selecting a test substance having a significantly high cancer cell proliferation inhibitory effect measured in (2) compared to that of a control;

[39] a method for evaluating safety of a test substance, the method comprising the steps of:
  (1) administering a test substance to the genetically modified non-human animal of any one of [1] to [7], [9], [10], [17] to [24], [26], and [27];
  (2) measuring cytokine release in the genetically modified non-human animal to which the test substance was administered; and
  (3) comparing the cytokine level measured in step (2) to the cytokine level of a control, wherein the change in cytokine level indicates the safety risk to be caused;

[40] the method of [39], wherein the non-human animal comprises a human GPC3 polypeptide-expressing cancer tissue or cancer cell;

[41] a method for evaluating pharmacokinetic characteristics of a test substance, the method comprising the steps of:
  (1) administering a test substance to the genetically modified non-human animal of any one of [1] to [7], [9], [10], [17] to [24], [26], and [27]; and
  (2) measuring the time-dependent changes in blood concentration of the test substance in the genetically modified non-human animal to which the test substance was administered;

[42] the method of [41], wherein the non-human animal comprises a human GPC3 polypeptide-expressing cancer tissue or cancer cell;

[43] a method for evaluating in vivo distribution characteristics of a test substance, the method comprising the steps of:
  (1) administering a test substance to the genetically modified non-human animal of any one of [1] to [7], [9], [10], [17] to [24], [26], and [27];
  (2) measuring the in vivo distribution of the test substance in the genetically modified non-human animal to which the test substance was administered; and
  (3) indicating the in vivo distribution characteristics of the test substance through localization of the test substance;

[44] the method of [43], wherein the non-human animal comprises a human GPC3 polypeptide-expressing cancer tissue or cancer cell;

[45] the method of any one of [38] to [44], wherein the test substance is an antigen-binding molecule that binds to a human GPC3 polypeptide;

[46] the method of [45], wherein the antigen-binding molecule is an antibody.

Furthermore, for example, the following invention is provided.

[47] the genetically modified non-human animal of any one of [1] to [10], [17] to [24], [26], and [27], wherein the animal is functionally deficient for at least one or more types of CD3 genes selected from the group consisting of endogenous CD3ε, CD3δ, and CD3γ in its genome and functionally expresses at least one or more types of human CD3 genes selected from the group consisting of human CD3ε, CD3δ, and CD3γ;

[48] the genetically modified non-human animal of [47], which functionally expresses human CD3 genes comprising human CD3☐, CD3☐, and CD3☐;

[49] the genetically modified non-human animal of [47] or [48], wherein a full-length nucleotide sequence of at least one or more types of human CD3 genes selected from the group consisting of human CD3☐, CD3☐, and CD3☐ has been inserted into the genome;

[50] the genetically modified non-human animal of any one of [47] to [49], wherein a T cell receptor derived from the non-human animal and human CD3 molecule(s) form a complex on the cellular membrane of a T cell carried by the non-human animal;

[51] the genetically modified non-human animal of any one of [47] to [50], the animal additionally expressing a human immune checkpoint gene, a human cancer-specific antigen gene, and/or a human immune costimulatory molecule gene;

[52] the genetically modified non-human animal of any one of [47] to [51], wherein the non-human animal is a non-human mammal;

[53] the genetically modified non-human animal of [52], wherein the non-human mammal is a mouse;

[54] the genetically modified non-human animal of any one of [47] to [53], which is for screening for a therapeutic agent for malignant neoplastic disease or autoimmune disease;

[55] the genetically modified non-human animal of [54], which is for screening for a therapeutic agent for malignant neoplastic disease, wherein a cancer cell has been transplanted into the non-human animal;

[56] the genetically modified non-human animal of [55], wherein the cancer cell is a cell derived from lung cancer, gastric cancer, liver cancer, esophageal cancer, or ovarian cancer;

[57] a method of screening for a therapeutic agent for malignant neoplastic disease or autoimmune disease, the method comprising the steps of:
  (1) contacting a test substance with the genetically modified non-human animal of any one of [47] to [56], or an organ, tissue, or cell thereof; and
  (2) selecting a candidate test substance using as an indicator drug efficacy and/or toxicity of the test substance in the genetically modified non-human animal individual, or the organ, tissue, or cell thereof;

[58] a method of screening for a therapeutic agent for malignant neoplastic disease, the method comprising the steps of:
  (1) administering one from a library of antigen-binding molecules as a test substance to a first genetically modified non-human animal of any one of [47] to [57], the antigen-binding molecules comprising a human CD3-binding domain and a cancer-specific antigen-binding domain;
  (2) measuring a cell proliferation inhibitory effect and/or pharmacokinetic characteristics of the test substance on a cell expressing the cancer-specific antigen; and
  (3) comparing the cell proliferation inhibitory effect and/or pharmacokinetic characteristics of the test substance with the cell proliferation inhibitory effect and/or pharmacokinetic characteristics of a control antibody administered to a second genetically modified non-human animal which is different from the first non-human animal;

[59] a method for producing a non-human animal expressing a human GPC3 polypeptide and functionally expressing human CD3 genes, the method comprising the steps of:
  (1) preparing a genetically modified non-human animal which is deficient in the expression of the endogenous GPC3 polypeptide and expresses a human GPC3 polypeptide;
  (2) preparing a genetically modified non-human animal which is functionally deficient in at least one or more types of CD3 genes selected from the group consisting of endogenous CD3ε, CD3δ, and CD3γ in its genome and functionally expresses at least one or more types of human CD3 genes selected from the group consisting of human CD3ε, CD3δ, and CD3γ; and
  (3) crossing the genetically modified non-human animal expressing the human GPC3 polypeptide with the genetically modified non-human animal functionally expressing the human CD3 genes.

BRIEF DESCRIPTION OF THE DRAWINGS

In FIG. 1, "a" indicates the mouse beta globin second exon, "b" indicates the mouse beta globin second intron, "c" indicates the mouse beta globin third exon, and "d" indicates the mouse beta globin third exon containing the polyadenylation signal.

FIG. 17 presents the representative examples of PCR analyses of genotypes of ES cell clones obtained by introducing into mouse Cd3 gene-modified ES cells the human CD3 gene region introduction vector along with a Cre expression vector and a Dre expression vector.

FIG. 25B. See the explanation under FIG. 25A.
FIG. 25C. See the explanation under FIG. 25A.
FIG. 25D. See the explanation under FIG. 25A.

MODE FOR CARRYING OUT THE INVENTION

1. Definition

Figure 1:
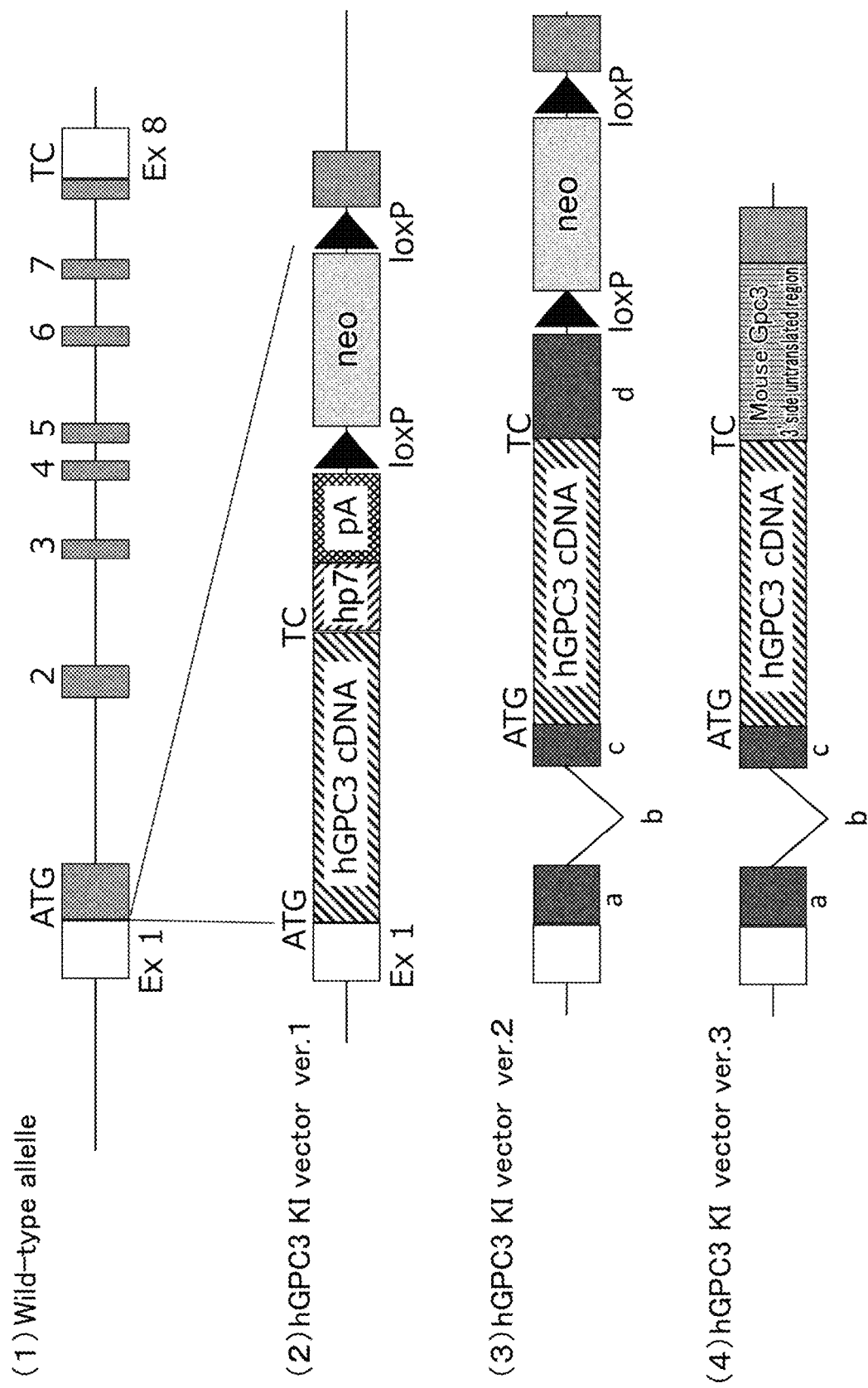
FIG. 1 schematically presents the relationship between the structure of a genomic DNA of the mouse glypican-3 (mGPC3) gene (1), and the knock-in vectors ver. 1 (2), ver. 2 (3), and ver. 3 (4) to be inserted. Knock-in vector ver. 1 (2) carries a human glypican-3 (hGPC3) cDNA, an hp7 sequence, a polyadenylation signal (pA), and a neomycin-resistance gene (neo) flanked by loxPs which are substrate sequences for Cre recombinase. Allowing Cre to act causes site-specific recombination between the loxPs, and the neomycin resistance gene flanked by the loxPs is removed. Knock-in vector ver. 2 (3) carries the approximately 800-nucleotide 5' upstream region of the mGpc3 gene target region; the mouse beta globin second exon, intron, and third exon; hGPC3 cDNA; the polyadenylation signal in the mouse beta globin third exon; loxP sequences; neo gene; and the approximately 800-nucleotide 3' downstream region of the mGpc3 gene target region. Knock-in vector ver. 3 (4) is a vector in which the polyadenylation signal in the mouse beta globin third exon of knock-in mouse ver. 2 (3) has been changed to the 3' untranslated region of the mGpc3 gene.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the specific methods and materials are described herein. All publications referred to herein are incorporated in their entirety by reference into this description.

Herein, unless a limitation referring to a numerical quantity such as "a single" or "multiple" is specifically used to describe a term, the terms recited herein should not be interpreted as being particularly limited in numerical quantity, and should be understood as terms with the meaning "one or more of".

"Conservative substitution" takes place within a family of amino acids that are related with regard to their side chains and chemical properties. For example, amino acids can be classified into the groups on the basis of their commonly shared side chain properties:
  (1) hydrophobic: norleucine, methionine (Met), alanine (Ala), valine (Val), leucine (Leu), and isoleucine (Ile);
  (2) neutral hydrophilic: cysteine (Cys), serine (Ser), threonine (Thr), asparagine (Asn), and glutamine (Gln);
  (3) acidic: aspartic acid (Asp) and glutamic acid (Glu);
  (4) basic: histidine (His), lysine (Lys), and arginine (Arg);
  (5) residues that affect the chain orientation: glycine (Gly) and proline (Pro); and
  (6) aromatic: tryptophan (Trp), tyrosine (Tyr), and phenylalanine (Phe).

Non-conservative substitution refers to an exchange of a member of any one of these classes with a member of a different class. In a non-limiting embodiment, the present invention includes genetically modified non-human animals that express a human GPC3 polypeptide containing a conservative amino acid substitution in an amino acid sequence described herein.

The term "target gene" includes endogenous genes of a non-human animal which becomes a target for insertion of a foreign gene. The term "target region" includes specific regions of endogenous genes of a non-human animal which becomes a target for insertion of a foreign gene. In a non-limiting embodiment, target regions refer to endogenous gene-containing regions which are adjacent to the 5' side and 3' side of an inserted foreign gene. In another embodiment, a target region refers to regions of an endogenous gene whose expression becomes deleted due to insertion of a foreign gene.

The term "endogenous" includes substances derived natively from inside organisms, tissues, cells, or such. For example, endogenous nucleic acids or peptides are present inside cells, and refer to nucleic acids or peptides that were not introduced into cells using recombinant engineering techniques.

The term "foreign" includes substances derived from other organisms, tissues, cells, or such that are different from organisms, tissues, or cells to be targeted. For example, "foreign genes" include genes introduced into non-human animals of the present invention. Foreign genes in the present invention may be used without being limited to a certain organism species from which they are derived, but they are preferably human genes. Furthermore, as foreign genes, reporter genes such as green fluorescent protein (GFP) and β-galactosidase, and selection marker genes such as drug-resistance genes (such as neomycin-resistance gene) may be used. A combination of two or more genes may also be used as foreign genes. Furthermore, foreign genes may have enhancers that regulate their expression, added to them. The forms of foreign genes are not particularly limited, and may be, for example, cDNA or genomic DNA.

The term "isolated" refers to being separated from the components of its original environment.

The term "functionally linked" includes a condition where a gene is linked under conditions that allow the gene to exhibit the function of interest. For example, a nucleic acid sequence coding for a protein may be operably linked to regulatory sequences (for example, promoter, enhancer, silencer sequence, etc.) to retain proper transcriptional regulation. As long as the sequence functions in that manner, the promoter does not have to be contiguously linked to the sequence. Herein, the term "functionally linked" may be used interchangeably with the term "operably linked".

Examples of the "vector" include genetically engineered plasmid or virus that is derived from a bacteriophage, adenovirus, retrovirus, poxvirus, herpesvirus, or artificial chromosome, but are not limited thereto.

The term "non-human animal" is not particularly limited as long as it is an animal other than a human, and examples include mouse, rat, guinea pig, hamster, rabbit, goat, cattle, horse, pig, dog, cat, and monkey. The non-human animal is preferably a mammal, an animal classified as a rodent, and more preferably a mouse. Examples of the preferred mouse include C57/BL/6, ICR, and BALB/c, but are not limited thereto.

Herein, "wild-type" includes having ordinary structure and/or activity found in nature. Wild-type nucleic acid or peptide includes a plurality of different forms and polymorphisms such as allelic mutations. Furthermore, "wild-type" non-human animals include, in some cases, animals having a wild-type GPC3 gene, or more specifically, animals not subjected to genetic engineering of GPC3.

Herein, the term "antibody" is used in the broadest sense and encompasses various antibody structures so long as they exhibit the desired antigen-binding activity, including but being not limited to monoclonal antibodies, polyclonal antibodies, multispecific antibodies (for example, bispecific antibodies), and antibody fragments.

An "antibody fragment" refers to a molecule other than an intact antibody that comprises a portion of the intact antibody, which portion binds to an antigen bound by the intact antibody. Examples of an antibody fragment include but are not limited to Fv, Fab, Fab', Fab'-SH, and F(ab')2; diabodies; linear antibodies; single-chain antibody molecules (for example, scFv); and multispecific antibodies formed from antibody fragments.

Herein, the terms such as "cancer", "carcinoma", "tumor", and "neoplasm" are not differentiated from each other, and are mutually interchangeable, and mean the generally expressed term "cancer".

2. Glypican 3 (GPC3)

Glypican 3 (GPC3) is a member of a family of heparin sulfate proteoglycans present on cell surfaces. While it is suggested to be possibly involved in cell division during development and proliferation of cancer cells, its function has not yet been clearly elucidated. In a non-limiting embodiment, examples of a GPC3 polypeptide sequence include SEQ ID NO: 1 (human, NCBI RefSeq: NP_004475.1), SEQ ID NO: 2 (monkey, NCBI RefSeq: XP_005594665.1), and SEQ ID NO: 3 (mouse, NCBI RefSeq: NP_057906.2), and examples of the DNA sequence include SEQ ID NO: 4 (human, NCBI RefSeq: NM_004484.3), SEQ ID NO: 5 (monkey, NCBI RefSeq: XM_005594608.2), and SEQ ID NO: 6 (mouse, NCBI RefSeq: NM_016697.3). In a non-limiting embodiment, glypican 3 (GPC3) or GPC3 polypeptide includes a full-length GPC3 polypeptide and a fragment thereof, and they may contain amino acid mutations.

In a non-limiting embodiment, a "GPC3 gene" is not particularly limited as long as it is a GPC3 polypeptide-coding gene, and may be a genomic DNA or a cDNA. Furthermore, a GPC3 gene includes its polymorphic or mutant forms.

3. Non-Human Animals Expressing a Human GPC3 Polypeptide

In a non-limiting embodiment, the present invention provides non-human animals expressing a human GPC3 polypeptide which comprise a human GPC3 gene-coding DNA. In another embodiment, non-human animals of the present invention include non-human animals in which the human GPC3 gene-coding DNA has been inserted into the same reading frame as that of an endogenous GPC3 gene which was present in the non-human animal genome. The above-mentioned human GPC3 gene-coding DNA may be a genomic DNA or a cDNA. Preferably, it is a cDNA, and specifically, examples include cDNA containing an amino acid sequence-coding region (CDS). An amino acid sequence-coding region includes a signal sequence.

In a non-limiting embodiment, the term "same reading frame" means a nucleotide sequence unit of every three bases that are read when a mRNA is translated into a protein. The phrase "inserted into the same reading frame" includes inserting a human GPC3 gene so that the initiation codon ATG of the human GPC3 gene comes to the site of the initiation codon ATG of an endogenous GPC3 gene of the non-human animal. Furthermore, the phrase "inserted into the same reading frame or insert(s)/inserting . . . into the same reading frame" also includes the case where an exon-intron structure sequence is added to the 5' side of the initiation codon ATG of the human GPC3 gene and the human GPC3 gene is inserted so that the initiation codon ATG of the endogenous GPC3 gene of the non-human animal is aligned with the 5' end of the exon-intron structure.

Thus, the promoter for the endogenous GPC3 gene in the non-human animal is operatively linked to the inserted human GPC3 gene, and the human GPC3 gene becomes expressed in response to activation of the promoter. When such constitution is employed, the foreign human GPC3 is expressed under the endogenous GPC3 expression regulation system; therefore, human GPC3 can be regulated to be expressed at a similar timing and place (tissues) as the endogenous GPC3. GPC3 is a gene also predicted to be involved in development. Therefore, employing the above-mentioned constitution is expected to act to reduce effects of gene modification on the survival and development of the non-human animal.

In another embodiment, it is preferable to delete a sequence having a number of bases that is not a multiple of three from the sequence following ATG of the endogenous GPC3 gene when inserting the human GPC3 gene, from the viewpoint of eliminating the possibility of retranslation of the disrupted endogenous GPC3 gene in the original reading frame. Furthermore, the human GPC3 gene in the present invention is preferably inserted nowhere else than the exon in which the original translation start site of the endogenous GPC3 gene is present (i.e., homologous recombination has taken place only with the target exon of the endogenous GPC3 gene).

In a non-limiting embodiment, the human GPC3 gene carried by the non-human animals of the present invention includes human GPC3 genes that are at least 50%, 60%, or 70%, preferably 75% or more, 80% or more, or 85% or more, more preferably 90% or more, 91% or more, 92% or more, 93% or more, 94% or more, 95% or more, 96% or more, 97% or more, 98% or more, or 99% or more homologous to SEQ ID NO: 4. In another embodiment, the human GPC3 gene includes its polymorphic or mutant forms. In another embodiment the human GPC3 gene may be a gene coding for a human GPC3 polypeptide in which amino acid insertions, deletions, or conservative amino-acid substitutions have been made.

In a non-limiting embodiment, the human GPC3 polypeptide expressed by the non-human animals of the present invention includes human GPC3 polypeptides that are at least 50%, 60%, or 70%, preferably 75% or more, 80% or more, or 85% or more, more preferably 90% or more, 91% or more, 92% or more, 93% or more, 94% or more, 95% or more, 96% or more, 97% or more, 98% or more, or 99% or more homologous to SEQ ID NO: 1. In another embodiment, the human GPC3 gene includes its polymorphic or mutant forms. In another embodiment, in the human GPC3 polypeptide, amino acid insertions, deletions, or conservative amino-acid substitutions may be made. In the present invention, homologies of the nucleotide sequences or amino acid sequences can be determined by a known algorithm. Algorithms for determining the homology among multiple sequences are known. Homology of sequence information is determined in some cases by considering the degeneracy of codons in the comparison among nucleotide sequences or by considering commonalities of different amino acid residues in the comparison among amino acid sequences. In other cases, the homology is determined simply by comparing sequence information without considering these factors. For the latter cases, comparison results are preferably presented as sequence identity.

In a non-limiting embodiment, the non-human animals of the present invention are deficient in expression of the non-human animal endogenous GPC3 polypeptide and can express the human GPC3 polypeptide at a physiologically adequate level. A human GPC3 gene (including mRNA) inserted into a non-human animal of the present invention or the human GPC3 polypeptide expressed from the gene can be detected by various methods well known to those skilled in the art, such as PCR, Southern blotting, Restriction Fragment Length Polymorphism (RFLP) method, Western blotting, IHC, and ELISA.

In a non-limiting embodiment, for example, embodiments of "deficient in expression of an endogenous GPC3 polypeptide" are not particularly limited as long as the endogenous GPC3 polypeptide in the non-human animal is not expressed. Specifically, for example, the endogenous GPC3 gene may be deleted (abolished) in a non-human animal genome using knockout technology based on genome editing techniques such as homologous recombination, CRISPR-Cas (CRISPR/Cas9), zinc finger nucleases, or TALEN. Alternatively, a method for completely suppressing the expression of an endogenous GPC3 gene by siRNA and such may be used. Furthermore, as long as an endogenous GPC3 polypeptide is not expressed, a foreign gene may be inserted at the position of the GPC3 gene in the non-human animal genome, for example, using knock-in technology.

In a non-limiting embodiment, the phrase "express the human GPC3 polypeptide at a physiologically adequate level" includes, for example, the case where an expression level of a human GPC3 polypeptide or a human GPC3 mRNA in a non-human animal is equivalent to any one expression level selected from the expression levels consisting of (i) to (iii) below:
(i) an expression level of a mouse GPC3 polypeptide or a mouse GPC3 mRNA in a wild-type mouse;
(ii) an expression level of a monkey GPC3 polypeptide or a monkey GPC3 mRNA in a wild-type monkey; and
(iii) an expression level of a human GPC3 polypeptide or a human GPC3 mRNA in a human.

Furthermore, it includes, for example, the case where an expression level of a human GPC3 polypeptide or a human GPC3 mRNA in one or more of organs in a non-human animal is equivalent to any one expression level selected from the expression levels consisting of (i) to (iii) below:
(i) an expression level of a mouse GPC3 polypeptide or a mouse GPC3 mRNA in the organ of a wild-type mouse;
(ii) an expression level of a monkey GPC3 polypeptide or a monkey GPC3 mRNA in the organ of a wild-type monkey; and
(iii) an expression level of a human GPC3 polypeptide or a human GPC3 mRNA in the organ of a human.

Preferably, the expression level of a human GPC3 polypeptide or a human GPC3 mRNA in one or more of organs in a non-human animal of the present invention is equivalent to the expression level of the human GPC3 polypeptide or the human GPC3 mRNA in the organ of a human. Herein, organs include lungs and trachea, but are not limited thereto. In the present invention, ordinarily, when expression level of one comparate is defined as 100 and expression level of the other is 50% to 150%, for example 70% to 130%, and more specifically 80% to 120%, the expression levels can be regarded as equivalent. Polypeptide and mRNA expression levels are desirably compared among common tissues or cells.

In a non-limiting embodiment, the GPC3 polypeptide expression level can be presented as the GPC3 polypeptide weight per total protein weight, and the GPC3 mRNA expression level can be presented as the copy number of the GPC3 mRNA in the total RNA. Methods for quantitatively evaluating the copy number of RNA are known. Specifically, by performing amplification reactions, for example by real-time PCR, using standard preparations with known amounts of RNA as the samples, a calibration curve (standard curve) can be drawn on the basis of the number of reaction cycles needed to reach a certain signal intensity. By performing a similar amplification reaction on an RNA sample to be quantified and measuring the number of reaction cycles needed to reach the same signal intensity, the amount of RNA in the sample can be determined through application of the obtained measurement result to the standard curve prepared in advance. Methods for determining the amount of total RNA by electrophoresis or absorbance measurements are known. In the present invention, total RNA may be total mRNA.

In another embodiment, "expressing/express(es) the human GPC3 polypeptide at a physiologically adequate level" can be determined when human GPC3-binding antibodies are administered to genetically modified non-human animals that express a human GPC3 polypeptide and the pharmacokinetic properties such as half-life in blood of the antibodies are similar to those in the case where the antibodies are administered to humans.

In a non-limiting embodiment, genetically modified non-human animals that express a human GPC3 polypeptide show immune tolerance to the human GPC3 polypeptide. More specifically, organisms activate their acquired immune response system against antigens that are foreign substances to the organism (itself). Thus, when a human GPC3 polypeptide is administered to or human GPC3 polypeptide-expressing cell is transplanted into a non-human animal, the human GPC3 polypeptide or the human GPC3 polypeptide-expressing cell is recognized as a foreign substance and is eliminated. However, genetically modified non-human animals of the present invention express the human GPC3 polypeptide, and thus, the non-human animals recognize the human GPC3 polypeptide as the animal's own biological component and do not show immune response against the polypeptide. Whether a genetically modified non-human animal of the present invention shows immune tolerance to human GPC3 can be confirmed by various methods known to those skilled in the art, for example, by administering the human GPC3 polypeptide or a fragment thereof to the non-human animal and measuring the anti-human GPC3 antibody titer in the body of the non-human animal. In another embodiment, non-human animals of the present invention which express the human GPC3 polypeptide have a normal immune system.

In a non-limiting embodiment, whether a non-human animal shows immune tolerance to a human GPC3 polypeptide can be confirmed by administering the human GPC3 polypeptide or a fragment thereof to a non-human animal, and then measuring the antibody titer of the anti-human GPC3 antibody in the plasma of the non-human animal. In doing so, an adjuvant may be administered together with the human GPC3 polypeptide or the fragment thereof. The antibody titer can be measured, for example, on day 0, day 14, day 21, day 28, day 35, day 42, and/or day 49 counting from the day of administration of the human GPC3 polypeptide or the fragment thereof. For example, when the antibody titer of the anti-human GPC3 antibody in the plasma of the genetically modified non-human animal that expresses the human GPC3 polypeptide is significantly lower than the antibody titer of the anti-human GPC3 antibody of a wild-type non-human animal, the genetically modified non-human animal can be recognized as presenting immune tolerance to the human GPC3 polypeptide.

In the present invention, that the genetically modified non-human animal is immunologically tolerant to the human GPC3 polypeptide is an advantageous characteristic for evaluating the various properties of antigen-binding molecules against human GPC3 in the animal. For example, one can assume a case where properties of an antigen-binding molecule are evaluated in model animals produced by transplanting human GPC3-expressing cancer cells into the genetically modified non-human animals of the present invention. In this instance, if a host animal shows immune response to human GPC3 and generates antibodies against human GPC3, the generated antibodies may interfere with the evaluation of the effects of the antigen-binding molecule. For example, if immunodeficient animal transplant models are used, there may be no problems associated with host immune response. However, an evaluation system using immunodeficient animals whose immune system has been made deficient does not allow evaluation of, for example, effects of the antigen-binding molecule on the immune system. On the other hand, since the genetically modified non-human animals of the present invention possess the immune system, such limitations will not be present.

4. DNAs and Knock-In Vectors

In a non-limiting embodiment, the present invention provides DNA constructs for producing non-human animals that express a human GPC3 polypeptide, and provides knock-in vectors carrying the DNA construct and transformed cells into which the knock-in vector has been introduced or progeny cells thereof.

In a non-limiting embodiment, DNA constructs of the present invention include DNA constructs containing a human GPC3 gene-coding DNA which has an exon-intron structure sequence added to the 5' side and a 3' untranslated region of the non-human animal GPC3 gene added to the 3' side. In another embodiment, the DNA construct of the present invention may further contain recombinase substrate sequences (for example, loxP sequences which are the substrate sequences for Cre), a drug selection marker (for example, the neo gene), and/or other sequences.

In a non-limiting embodiment, DNA constructs of the present invention include a DNA construct containing a human GPC3 gene-coding DNA which has an exon-intron structure sequence added to the 5' side and a 3' untranslated region of the non-human animal beta globin added to the 3' side. In another embodiment, the DNA construct of the present invention may further contain recombinase substrate sequences (for example, loxP sequences which are the substrate sequences for Cre), a drug selection marker (for example, the neo gene), and/or other sequences.

In a non-limiting embodiment, the term "exon-intron structure sequence" means a sequence containing both an exon which is not removed by splicing reaction and an intron which is removed by splicing reaction. The exon-intron structure sequence may be any sequence as long as it is a sequence containing both an exon and an intron and in which the introns are removed by splicing. Examples of the exon-intron structure sequence of the present invention include but are not limited to a sequence comprising the beta globin second exon sequence, intron sequence, and third exon sequence.

In a non-limiting embodiment, the DNA constructs of the present invention include a DNA construct comprising a human GPC3 gene-coding DNA which has the beta globin second exon, intron, and third exon added to the 5' side, and 3' untranslated region of the non-human animal GPC3 gene added to the 3' side. In another embodiment, the DNA constructs of the present invention include a DNA construct comprising a human GPC3 gene-coding DNA which has the beta globin second exon, intron, and third exon added to the 5' side, and which has 3' untranslated region of the non-human animal GPC3 gene, drug resistance marker, and recombinase substrate sequences added to the 3' side. The beta globin is not particularly limited, but is preferably a beta globin derived from the genetically modified non-human animal. For example, when the genetically modified non-human animal is a mouse, the beta globin is preferably a mouse beta globin, but it may be another beta globin (for example, rabbit beta globin). The length of the 3' untranslated region of the non-human animal GPC3 gene added to the 3' side is preferably approximately 800 bp or longer.

Meanwhile, in a knock-in vector of the present invention, the human GPC3 gene-coding DNA may ordinarily be a cDNA. Preferably, the human GPC3 cDNA may comprise its coding sequence. For example, the nucleotide sequence of SEQ ID NO: 10 includes the initiation codon (atg) to the stop codon (tga) in the human GPC3 cDNA, and encodes the full-length amino acid sequence of human GPC3 (580 amino acids including the signal sequence).

In a non-limiting embodiment, the DNA constructs of the present invention include a DNA construct comprising a human GPC3 gene-coding DNA which has the beta globin second exon, intron, and third exon added to the 5' side, and 3' untranslated region of beta globin added to the 3' side. In another embodiment, the DNA constructs of the present invention include a DNA construct comprising a human GPC3 gene-coding DNA which has the beta globin second exon, intron, and third exon added to the 5' side, and which has 3' untranslated region of beta globin of the non-human animal, drug selection marker, and recombinase substrate sequences added to the 3' side. The beta globin is not particularly limited, but is preferably a beta globin derived from the genetically modified non-human animal. For example, when the genetically modified non-human animal is a mouse, the beta globin is preferably a mouse beta globin, but it may be another beta globin (for example, rabbit beta globin).

Examples of the structures of the above-described DNA constructs may include DNA constructs comprising the following nucleotide sequence: 5'-coding sequence of hGPC3 (SEQ ID NO: 10)—hp7 sequence (SEQ ID NO: 11)-polyadenylation signal (SEQ ID NO: 12)—3'; or 5'-mouse beta globin second exon (SEQ ID NO: 14)—intron (SEQ ID NO: 15), third exon (SEQ ID NO: 16)—coding sequence of hGPC3 gene (SEQ ID NO: 10)—polyadenylation signal in the third exon of mouse beta globin-3'.

Furthermore, a 5'-side upstream sequence of the mouse GPC3 gene can be positioned in the 5'-side upstream region of the above-mentioned structure. For the 5'-side upstream sequence of the mouse GPC3 gene, for example, the upstream 800 bp of the translation start site can be used. On the other hand, similarly, a 3'-side downstream sequence of the mouse GPC3 gene can be positioned in the 3'-side downstream region of the above-mentioned structure. As the 3'-side downstream sequence of the mouse GPC3 gene, for example, 800 bp of the downstream region of the stop codon can be used.

As a recombinase that acts sequence specifically in the present invention, recombinases such as Cre, Dre, and Flp may be used. A specific recombinase for a substrate sequence inserted into the genomic region is used. That is, the loxP sequence is used for Cre, the Rox sequence is used for Dre, and the Frt sequence is used for Flp. Here, without being limited to the following, the nucleotide sequence of ATAACTTCGTA TAGCATACATTATACGAAGTTAT (SEQ ID NO: 7) may be used as the "loxP sequence", the nucleotide sequence of TAACTTTAAATAATTGGCATT-ATTTAAAGTTA (SEQ ID NO: 8) may be used as the "Rox sequence", and the nucleotide sequence of GAAGTTCCT-ATTCTCTAGAAAGTATAGGAACTTC (SEQ ID NO: 9) may be used as the "Frt sequence".

As a drug selection marker in the present invention, for example, neomycin-resistance gene (neo), hygromycin B phosphotransferase gene, or such may be used for positive selection, and herpesvirus thymidine kinase gene (HSV-tk), diphtheria toxin A gene, or such may be used for negative selection.

In a non-limiting embodiment, the phrase "knock-in vector carrying the DNA construct" of the present invention refers to a vector having the ability to insert the above-described DNA construct for producing the non-human animals into the target gene region in a host through homologous recombination; and having a 5' arm (a nucleotide sequence homologous to a nucleotide sequence 5' upstream of the target region) positioned on the 5' side of the DNA construct for producing the non-human animals, and a 3' arm (a nucleotide sequence homologous to a nucleotide sequence 3' downstream of the target region) positioned on the 3' side of the DNA construct. In the present invention, a knock-in vector is constructed so that it inserts the DNA construct for producing the non-human animals into the same reading frame as that of the target gene in a host. In one embodiment, in the knock-in vector, it is preferable that a foreign gene is inserted into the exon containing a translation start site such that the translation start site of the foreign gene comes at the position where the translation start site of the target gene was. In this case, in the knock-in vector, a nucleotide sequence further upstream of the translation start site of the target gene is preferably positioned at the 5' side of the translation start site of the foreign gene. In another embodiment, when an exon-intron structure sequence has been added to the 5' side of a foreign gene in the knock-in vector, the foreign gene is preferably inserted into an exon containing a translation start site such that the 5' end of the exon-intron structure comes at the position where the translation start site of the target gene was. In this case, in the knock-in vector, a nucleotide sequence further upstream from the translation start site of the target gene is preferably positioned at the 5' side upstream of the 5' end of the exon-intron structure.

Furthermore, the knock-in vectors of the present invention preferably have the ability to replicate in host cells. Such vectors can be constructed, for example, by inserting a DNA for producing the non-human animals into a known vector. The knock-in vectors are not particularly limited as long as they are vectors used in genetic engineering, and examples of known vectors include plasmid vectors, cosmid vectors, bacterial artificial chromosome (BAC) vectors, yeast artificial chromosome (YAC) vectors, retrovirus vectors, lentivirus vectors, and other virus vectors, but are not limited thereto.

In a non-limiting embodiment, the "transformed cells into which the knock-in vector has been introduced" of the present invention are cells into which the knock-in vector carrying the DNA for producing the non-human animals has been introduced. In another embodiment, the transformed cells of the present invention are cells in which a human GPC3 gene-coding DNA that has an exon-intron structure sequence added to the 5' side and a 3' untranslated region of the non-human animal GPC3 gene added to the 3' side has been inserted into the same reading frame as that of the endogenous GPC3 gene present in the non-human animal genome.

Furthermore, in another embodiment, the transformed cells of the present invention are cells in which a human GPC3 gene-coding DNA that has an exon-intron structure sequence added to the 5' side and a 3' untranslated region of the non-human animal beta globin added to the 3' side has been inserted into the same reading frame as that of an endogenous GPC3 gene present in the non-human animal genome. The host cells into which the knock-in vector is introduced are cells of the non-human animals, or cells (including a cell population) that can differentiate into cells of the non-human animals. Various cells can be used as such host cells according to the objective, and examples include pluripotent stem cells such as embryonic stem cells (ES cells) and induced pluripotent stem cells (iPS cells), germ-line stem cells having the ability to differentiate into reproductive cells such as sperm stem cells, or fertilized eggs. The knock-in vector can be introduced into the host cell by known methods such as electroporation. Alternatively, the present invention provides cells transformed with knock-in vectors of the present invention, genetically modified non-human animals that developed from the cells, and model animals produced by transplanting cancer cells to the genetically modified non-human animals or by inducing carcinogenesis in the genetically modified non-human animals. Furthermore, the present invention relates to methods for evaluating properties such as cell proliferation inhibitory effect, safety, or pharmacokinetic characteristics of an antigen-binding substance or a test substance to be evaluated for its therapeutic effects on cancer, using these genetically modified non-human animals and model animals.

5. Methods for Producing a Non-Human Animal that Expresses a Human GPC3 Polypeptide In a non-limiting embodiment, the method for producing a non-human animal that expresses a human GPC3 polypeptide includes introducing into a host cell, a knock-in vector carrying a human GPC3 gene-coding DNA. Methods for introducing a knock-in vector carrying a human GPC3 gene-coding DNA is not particularly limited, and known methods can be used appropriately, including microinjection of knock-in vectors into the pronuclei of fertilized eggs; and introduction of knock-in vectors into pluripotent stem cells such as ES cells and iPS cells, and germline stem cells such as sperm stem cells by electroporation, lipofection, viral infection, transformation, and such.

In a non-limiting embodiment, the knock-in vector is injected into a host cell together with an artificial nuclease such as zinc finger nuclease (ZFN) or transcription activator-like effector nuclease (TALEN), or with clustered regularly interspaced short palindromic repeat (CRISPR)/Cas9, which causes cleavage by binding to a specific target sequence in the target region in the genome.

In a non-limiting embodiment, a chimeric animal can be obtained by injecting into an early embryo, a pluripotent stem cell into which a knock-in vector has been introduced, through a known method such as microinjection, and transplanting the embryo into a foster parent for development. Furthermore, an individual that is homozygous for the knock-in allele can be yielded from progeny by breeding this chimeric animal.

In another embodiment, when using germline stem cells, a knock-in animal can be produced by transplanting the cells in which the knock-in vector has been introduced by a known method for target recombination, into the gonad of an animal to allow the cells to be differentiated into germ cells, and mating the animal, or by use of the germ cells collected from the animal (Kanatsu-Shinohara, M. et al. (2008) Biol. Reprod. 79, 1121-1128).

In another embodiment, when using the fertilized eggs, a knock-in animal can be produced by transplanting the fertilized eggs into which the knock-in vector has been injected together with artificial nucleases or such, into a foster parent for development. The methods using ZFN and TALEN are described in the document (Cui, X. et al. (2011) Nat.

Biotechnol. 29, 64-67) and the document (Li, T. et al. (2011) Nucleic Acids Res. 39, 6315-6325), respectively. The method using CRISPR/Cas9 is described in the document (Yang, H. et al. (2013) Cell. in press.).

Furthermore, in another embodiment, an individual having a knock-in allele can be obtained by injecting the knock-in vector into the testis or ovary of an animal, and directly causing gene recombination in its germ cells by a technique such as electroporation, followed by mating (Niu, Y et al. (2008) J. Genet. Genomics. 35, 701-714).

In the present invention, the genetically modified non-human animal may be a homozygous animal having the two knock-in alleles on homologous chromosomes, or a hemizygous animal having a single copy of the knock-in allele. In breeding, to stably retain the modified phenotype, homozygous animals are preferred. Since GPC3 is positioned on the X chromosome, females (XX) can be homozygous, but males (XY) will be hemizygous. On the other hand, hemizygous females express human GPC3 by the presence of the knock-in allele, but since they are being deficient in their endogenous GPC3 allele, endogenous GPC3 expression is suppressed.

Alternatively, the present invention relates to a method for producing non-human animals that express a human GPC3 polypeptide, the method comprising the steps of:
(A) introducing a knock-in vector of the present invention into a stem cell of a non-human animal to incorporate a human GPC3-coding gene into an endogenous GPC3 allele in the stem cell genome of the non-human animal;
(B) transplanting the non-human animal stem cell of step (A) into an early embryo of the same non-human animal;
(C) transplanting the early embryo of step (B) into the uterus of a non-human animal foster parent for development, and obtaining a chimeric animal of a non-human animal having in its somatic cells a genome in which the knock-in vector has been introduced; and
(D) breeding the chimeric animal of step (C) and obtaining from its progeny an individual which is homozygous for the knock-in allele.

Alternatively, the present invention relates to a method for producing non-human animals that express a human GPC3 polypeptide, the method comprising the steps of:
(A) introducing a knock-in vector of the present invention into a fertilized egg of a non-human animal to incorporate a human GPC3-coding gene into an endogenous GPC3 allele in the fertilized egg genome of the non-human animal;
(B) transplanting the non-human animal fertilized egg of step (A) into the uterus of a non-human animal foster parent for development, and obtaining a non-human animal having in its somatic cells a genome in which the knock-in vector has been introduced; and
(C) breeding the non-human animal of step (B) and obtaining from its progeny an individual which is homozygous for the knock-in allele.

In the production methods of the present invention, the knock-in vector ordinarily carries a human GPC3 cDNA in a manner that allows the expression, and has an expression cassette containing the human GPC3 cDNA and the expression regulatory region that is bracketed by recombination regions for incorporating the cassette into the endogenous GPC3 allele in the non-human animal genome.

6. Methods for Evaluating Test Substances Using Non-Human Animals that Express a Human GPC3 Polypeptide In a non-limiting embodiment, non-human animals of the present invention can be used for various evaluations of test substances for their safety, therapeutic effects on a disease, pharmacokinetics, in vivo distribution, and such. Accordingly, the present invention also provides methods for evaluating a test substance using such non-human animals of the present invention. In another embodiment, the present invention includes non-human animals for use in various evaluations of test substances for their safety, therapeutic effects on a disease, pharmacokinetics, in vivo distribution, or such, and/or screening. Furthermore, in another embodiment, the present invention includes use of the non-human animals of the present invention for use in various evaluations of the test substances for their safety, therapeutic effects on a disease, pharmacokinetics, in vivo distribution, or such, and/or screening.

Examples of the "test substance" to subject to the evaluation method of the present invention include, but are not particularly limited to, peptides, proteins, non-peptide compounds, synthetic compounds, fermentation products, and cell extracts. The test substance is preferably an antibody against human GPC3. Examples of the antibody include known antibodies described in WO2003/000883, WO2004/022739, WO2006/006693, WO2007/047291, WO2006/046751, WO2009/041062, WO2016/047722, and such. The test substance can be administered to the non-human animal, for example, to the tail vein, subcutaneously, intraperitoneally, orally, transnasally, percutaneously, or transpulmonarily, but not limited thereto.

Embodiments of evaluation of test substances are exemplified below. For example, a test substance can be evaluated for its safety towards a living body by administering the test substance to the non-human animal of the present invention and measuring the plasma concentration of cytokines (for example, IFN-gamma, IL-10, IL-17, IL-2, IL-4, IL-6, and TNF, but not limited thereto). More specifically, the cytokine level is compared to the level of the same cytokine in a control, and when the two levels are found to be different, safety risk of the test compound is indicated. Here, "safety risk" refers to prediction of a biological reaction that yields some kind of disadvantage in a living body, due to change in cytokine levels. The roles of cytokines, represented by previously exemplified IFN-gamma, IL-10, IL-17, IL-2, IL-4, IL-6, and TNF, in a living body are well known, and a lot of information has been accumulated regarding the relationship between change in the levels of each of the cytokines during disease treatment and biological response. Therefore, those skilled in the art can predict the safety risk suggested by changes in cytokine levels. Here, when the expression levels of the human GPC3 gene in one or more of organs of the non-human animals are equivalent to those of mice, monkeys, or humans, results of safety tests using the non-human animals can be extrapolated to those of mice, monkeys, or humans, and effects on mice, monkeys, or humans can be predicted. In another embodiment, the non-human animals may comprise human GPC3-expressing cancer cells.

Furthermore, therapeutic effect of a test substance can be evaluated by administering the test substance to the non-human animal of the present invention which carries human GPC3 polypeptide-expressing cancer cells, and determining whether proliferation of the cancer cells is suppressed. Here, therapeutic effect can be rephrased as anti-tumor effect or cytotoxic activity. Whether proliferation of cancer cells comprised in the non-human animal is suppressed can be evaluated by measuring the size of the cancer cells and its change.

The non-human animals of the present invention which comprise human GPC3 polypeptide-expressing cancer cells include non-human animals in which human GPC3 polypeptide-expressing cancer cells have been transplanted. As described above, in a non-limiting embodiment, a non-human animal that expresses a human GPC3 polypeptide shows immune tolerance to the human GPC3 polypeptide. Accordingly, even when human GPC3 polypeptide-expressing cancer cells are transplanted to the non-human animals expressing the human GPC3 polypeptide of the present invention, the non-human animals do not present immune response to the cancer cells. Therefore, use of the non-human animals of the present invention as models enables a more accurate evaluation of therapeutic effects of test substances.

In another embodiment, the non-human animals of the present invention which comprise human GPC3 polypeptide-expressing cancer cells are non-human animals of the present invention that have developed cancer. The cancer may have developed spontaneously, or its onset may have been induced artificially. Non-human animal models in which onset of cancer is induced, and methods for their production are known. Specifically, for example, animal models and methods for producing such animal models are known, which models are prepared by inducing insulin resistance and loading high-fat diet in non-human animals, develop pathological conditions that progress from hepatitis to hepatic fibrogenesis and to liver cirrhosis, and develop liver cancer associated with the progress in pathological conditions (WO2011013247 A1). Furthermore, animal models developing pathological conditions that progress from hepatitis to hepatic fibrogenesis and to liver cirrhosis by being fed a choline-deficient L-amino acid-defined high fat diet containing 0.1% methionine (CDAHFD) and methods for producing such models are known (International Journal of Experimental Pathology, 2013 April; 94(2): 93-103). It is also possible to induce onset of liver cancer by continuing to feed CDAHFD to the animal models.

Therefore, the present invention provides model animals for evaluating therapeutic effects of test compounds on cancer. Model animals for evaluating therapeutic effects on cancer based on the present invention can be produced using the genetically modified non-human animals of the present invention. More specifically, the present invention relates to methods for producing model animals for evaluating therapeutic effects of test compounds on cancer, the method comprising the steps of:

(A) introducing a knock-in vector of the present invention into a stem cell of a non-human animal to incorporate a human GPC3-coding gene into an endogenous GPC3 allele in the stem cell genome of the non-human animal;

(B) transplanting the non-human animal stem cell of step (A) into an early embryo of the same non-human animal;

(C) transplanting the early embryo of step (B) into the uterus of a non-human animal foster parent for development, and obtaining a chimeric animal of a non-human animal having in its somatic cells a genome into which the knock-in vector has been introduced;

(D) breeding the chimeric animal of step (C) and obtaining from its progeny an individual in which the knock-in allele has been made homozygous; and (E) transplanting cancer cells or inducing onset of cancer in the homozygote individual of step (D) to produce a model animal for evaluation of therapeutic effects on cancer.

Furthermore, the present invention provides other model animals for evaluating therapeutic effects of test compounds on cancer. Model animals for evaluating therapeutic effects on cancer based on the present invention can be produced using the genetically modified non-human animals of the present invention. More specifically, the present invention relates to methods for producing model animals for evaluating therapeutic effects of test compounds on cancer, the method comprising the steps of:

(A) introducing a knock-in vector of the present invention into a fertilized egg of a non-human animal to incorporate a human GPC3-coding gene into an endogenous GPC3 allele in the fertilized egg genome of the non-human animal;

(B) transplanting the non-human animal fertilized egg of step (A) into the uterus of a non-human animal foster parent for development, and obtaining a non-human animal having in its somatic cells a genome in which the knock-in vector has been introduced;

(C) breeding the non-human animal of step (B) and obtaining from its progeny an individual in which the knock-in allele has been made homozygous; and (D) transplanting cancer cells or inducing onset of cancer in the homozygote individual of step (C) to produce a model animal for evaluation of therapeutic effects on cancer.

In a non-limiting embodiment, suitable examples of cancer cells transplanted into non-human animals of the present invention include ovarian cancer cells, prostate cancer cells, breast cancer cells, esophageal cancer cells, kidney cancer cells, uterine cancer cells, liver cancer cells, lung cancer cells, pancreatic cancer cells, stomach cancer cells, bladder cancer cells, or colorectal cancer cells. The term "cancer" as described herein refers not only to epithelial malignant tumors such as ovarian cancer and stomach cancer, but also to non-epithelial malignant tumors including hematopoietic cancers such as chronic lymphocytic leukemia and Hodgkin's lymphoma. Furthermore, the cancer cells for transplantation of the present invention are desirably GPC3-expressing cancer cells to evaluate pharmaceutical agents that target GPC3.

In the present invention, cancer cells to be transplanted to a genetically modified non-human animal may be cancer cells derived from any animals. Particularly, cancer cells derived from the same species as the non-human animal that will serve as a host are preferred as the cancer cells for transplantation (allogeneic transplantation). Furthermore, by using species for which the strains are managed, such as mice or rats for laboratory use, for the genetically modified non-human animals, cancer cells derived from the same strain, not just from the same species, can be transplanted (isogeneic transplantation). Use of cancer cells having as high genetic similarity as possible in this way for the cancer cells for transplantation can suppress actions not resulting from test compounds, such as immune response of a host against the cells, and enable more specific evaluation of therapeutic effects of the test compounds on cancer. In the present invention, cancer cells can be transplanted subcutaneously and such. Alternatively, by transplantation into a specific tissue, transitional characteristics of the test compounds into tissues can be evaluated.

Furthermore, effective blood concentration or pharmacokinetic characteristics of the test substance can be evaluated by measuring the blood concentration of a test substance in the non-human animal of the present invention to which the test substance has been administered. Herein, the term "pharmacokinetic characteristics" refers to properties of a test substance in the body of an animal, such as blood half-life, and elimination rate. For example, in a non-limiting embodiment, a substance having a lower effective blood concentration, a longer blood half-life, or a slower elimination rate is determined to have superior pharmacokinetic characteristics. The method for measuring the blood concentration of a test substance is not particularly limited. When the test substance is a protein (including an antibody), the method may be ELISA, and when the test substance is a small molecule compound, the method may be liquid chromatography-mass spectrometry (LC-MS). Regarding the methodology for evaluating pharmacokinetic characteristics based on the blood concentration, see the document by Igawa et al. (2010) Nat. Biotechnol. 28:1203-1207. Use of the above-mentioned methods for evaluating test substances of the present invention enables efficient selection of therapeutic agents which target human GPC3 and have a desired activity. Therefore, the present invention also provides a method for selecting such an antibody.

Furthermore, the degree to which the test substance reaches the targeted site and the in vivo distribution properties of the test substance can be evaluated by observing the distribution of the test substance in the body of a non-human animal of the present invention to which the test substance has been administered. For example, the distribution of a test substance in a body can be observed by administering a human GPC3-targeting therapeutic agent conjugated with an imaging agent as the test substance to the non-human animal of the present invention to which the human GPC3-expressing cancer cells have been transplanted, and detecting the imaging agent. Radionuclides used for imaging include but are not limited to I-131, I-123, In-111, and Tc-99m for SPECT imaging, and F-18, I-124, Cu-64, Y-86, and such for PET imaging. In a non-limiting embodiment, as a result of detecting the imaging agent, when the test substance shows high degree of accumulation in cancer cells, the test substance is recognized as having high specificity towards cancer cells.

As a non-limiting embodiment, the present invention provides a method of screening for therapeutic agents for malignant neoplastic disease or autoimmune disease, the method comprising the steps of:
(1) contacting a test substance with the non-human animal of the present invention, or an organ, tissue, or cell thereof; and
(2) selecting a candidate test substance using as an indicator either one or both of drug efficacy and toxicity of the test substance in the non-human animal individual, or the organ, tissue, or cell thereof.
In another embodiment, human GPC3-expressing cancer cells may have been transplanted into the non-human animal.

In a non-limiting embodiment, therapeutic effect (drug efficacy) and/or safety (toxicity) of a test substance in the non-human animal individuals of the present invention, organs, tissues, or cells thereof can be measured to select the test substances found to have drug efficacy or high drug efficacy, or to select the test substances with low or no toxicity. Alternatively, similar measurements can be performed using substances having drug efficacy as a comparative control, and test substances having high drug efficacy or low toxicity compared to that of the control can be selected. Drug efficacy is not particularly limited, and includes for example cell proliferation inhibitory effect, cytotoxicity, or tumor growth inhibitory effect.

For example, the present invention provides a method of screening for a therapeutic agent for malignant neoplastic disease, the method comprising the steps of:
(1) administering as a test substance an antigen-binding molecule comprising a human GPC3-binding domain to a first non-human animal individual of the present invention into which human GPC3-expressing cancer cells have been transplanted;
(2) measuring either one or both of a cell proliferation inhibitory effect and pharmacokinetic characteristics of the test substance on the cancer cells; and
(3) comparing either one or both of the cell proliferation inhibitory effect and pharmacokinetic characteristics of the test substance with either one or both of the cell proliferation inhibitory effect and pharmacokinetic characteristics of a control antibody administered to a second non-human animal individual of the present invention into which human GPC3-expressing cancer cells have been transplanted and which is different from the first individual. The screening step of the present invention can additionally include the step of (4) selecting a test substance having either one or both of excellent cell proliferation inhibitory effect and pharmacokinetic characteristics based on the results of step (3).

In the present invention, cell proliferation inhibitory effect and pharmacokinetic characteristics of the control antibody do not necessarily have to be both exceeded at the same time. Rather, by repeating the process of screening for candidates using test substances that have a certain level of recognition for one of the characteristics, the test substances can be efficiently narrowed down as a result, to those having more superior effects with regard to both characteristics.

Selection refers to using the method for evaluating the test substances of the present invention to efficiently produce anti-human GPC3 antibodies having the desired activities. Therefore, the present invention provides such methods for selecting antibodies.

Antibodies that efficiently inhibit proliferation of human GPC3-expressing cancer cells can be obtained by determining whether cancer cell line proliferation has been suppressed in a non-human animal to which a human GPC3-expressing cancer cell line has been transplanted and then antibodies against human GPC3 have been administered as a test substance and by selecting antibodies that suppress cancer cell proliferation. Furthermore, antibodies against human GPC3 that have a desired kinetics in the body can be obtained by measuring the blood concentration of the antibodies in non-human animals to which antibodies against human GPC3 have been administered, and by selecting antibodies having the desired blood concentration. When antibodies thus evaluated for the activity and selected are mouse monoclonal antibodies and such, these antibodies can be chimerized or humanized to obtain antibodies with low antigenicity as well as few side effects when administered to humans. Antibodies thus obtained can be used as useful therapeutic agents in the treatment of GPC3-expressing cancer.

In a non-limiting embodiment, as long as cancer highly expresses GPC3 to be targeted, any cancer falls under cancer to be targeted by the therapeutic agents evaluated, screened, or selected by the above-mentioned method. An example of such a cancer is a cancer selected from among breast cancer, uterine cervical cancer, colorectal cancer, endometrial cancer, head and neck cancer, liver cancer, lung cancer, malignant carcinoid, malignant glioma, malignant lymphoma, malignant melanoma, ovarian cancer, pancreatic cancer, prostate cancer, kidney cancer, skin cancer, stomach cancer, testicular cancer, thyroid cancer, and urothelial carcinoma.

7. CD3

A T-cell receptor (TCR) complex is an antigen-receptor molecule expressed mainly on T cells. It is composed of antigen-binding TCRα and β chains (or δ and γ chains), and multiple CD3 molecules (CD3-epsilon (ε), CD3-delta (δ), and CD3-gamma (γ)) and CD247 that mainly have a function of transducing signals into cells.

Generally, regarding the way for describing the gene names, in some biological species, CD3ε, CD3δ, and CD3γ may be written as CD3E, CD3D, and CD3G, respectively; however, the gene names of CD3ε, CD3δ, and CD3γ are used herein independent of the biological species. More specifically, in the present invention, CD3ε includes CD3E and CD3e, CD3δ includes CD3D and CD3d, and CD3γ includes CD3G and CD3g. For example, when denoted herein as "human CD3ε", this refers to a human CD3 epsilon gene, and when denoted as "mouse Cd3ε", this refers to a mouse Cd3 epsilon gene. When denoted herein as "human CD3δ", this refers to a human CD3 delta gene, and when denoted as "mouse Cd3δ", this refers to a mouse Cd3 delta gene. Furthermore, when denoted herein as "human CD3γ", this refers to a human CD3 gamma gene, and when denoted as "mouse Cd3γ", this refers to a mouse Cd3 gamma gene.

In the present invention, one or more types of CD3ε selected from the group consisting of human CD3ε, CD3δ, and CD3γ are not particularly limited, but may be, for example, human CD3ε. CD3ε may be two or more types of CD3ε selected from the group consisting of human CD3ε, CD3δ, and CD3γ, and may be, for example, human CD3ε and CD3δ, human CD3ε and CD3γ, or human CD3δ and CD3γ. They may also be CD3ε comprising human CD3ε, CD3δ, and CD3γ, i.e., all three types.

8. Non-Human Animals Functionally Expressing Human CD3 Genes

The present invention also relates to a genetically modified non-human animal which is functionally deficient in at least one or more types of CD3 genes selected from the group consisting of endogenous CD3ε, CD3δ, and CD3γ in its genome and functionally expresses at least one or more types of human CD3 genes selected from the group consisting of human CD3ε, CD3δ, and CD3γ.

In the present invention, the phrase "functionally deficient in an endogenous gene in a genome" is not particularly limited as long as an endogenous target gene (for example, CD3ε, CD3δ, or CD3γ) in a non-human animal genome does not express its function, and may include an embodiment in which an endogenous target gene (for example, CD3ε, CD3δ, or CD3γ) in a non-human animal genome or its protein is not expressed. For example, a targeted gene may be deleted (abolished) in a non-human animal genome using knockout technology based on genome editing techniques such as homologous recombination, CRISPR-Cas (CRISPR/Cas9), zinc finger nucleases, or TALEN, or a method for completely suppressing the expression of a targeted gene by siRNA and such may be used. Furthermore, as long as an endogenous target gene is not expressed, a foreign gene may be inserted at the position of the target gene in the non-human animal genome, for example, using knock-in technology.

In a non-limiting embodiment of the present invention, differentiation and production of mature T cells is inhibited in an animal which is functionally deficient in at least one or more types of CD3 genes selected from the group consisting of endogenous CD3ε, CD3δ, and CD3γ in its genome, when the animal is not made to express foreign CD3 such as human CD3 gene(s). Herein, mature T cells are, for example, T cells in which either CD4 or CD8 (not both) is positive (referred to as CD4 single positive cells and CD8 single positive cells, respectively). More specifically, in the spleen of an animal which is deficient in at least one or more types of CD3 genes selected from the group consisting of endogenous CD3ε, CD3δ, and CD3γ in its genome, when the animal does not express foreign CD3 such as human CD3 gene(s), a total of CD4 single positive cells and CD8 single positive cells is for example, 70% or less, preferably 60% or less, more preferably 50% or less, 40% or less, 30% or less, 20% or less, 10% or less, 5% or less, 3% or less, or 1% or less compared to the level of a wild type or the level generally regarded as normal. The developmental stage at which the mature T cells are counted may be any stage as long as it is a stage at which mature T cells are produced in the wild type, and preferably the age when an animal typically reaches adulthood (becomes fertile), for example, 8- to 12-weeks old, such as 12-weeks old, for mice.

Furthermore, in a non-limiting embodiment of the present invention, antibody production is inhibited in an animal which is deficient in at least one or more types of CD3 genes selected from the group consisting of endogenous CD3ε, CD3δ, and CD3γ in the genome, when the animal dose not express foreign CD3 such as human CD3 gene(s). Herein, the types of antibodies are not particularly limited, and for example, production of IgG (such as IgG1), and/or production of IgE may be inhibited. Whether antibody production is inhibited can be determined by inoculating a foreign antigen, and observing whether antibodies are produced or measuring the amount of antibodies produced. The foreign antigen is not particularly limited, and antibody production can be confirmed using a desired antigen, for example, chicken ovalbumin (OVA). In an animal which is deficient in at least one or more types of CD3 genes selected from the group consisting of endogenous CD3ε, CD3δ, and CD3γ in the genome when the animal does not express foreign CD3 such as human CD3 gene(s), the antibody titer is for example, 70% or less, preferably 60% or less, more preferably 60% or less, 50% or less, 40% or less, 30% or less, 20% or less, 10% or less, 5% or less, 3% or less, or 1% or less compared to the level of a wild type or the level generally regarded as normal. The developmental stage at which the antibody production is measured may be any stage as long as it is a stage at which antibodies are produced in the wild type, preferably the age when an animal typically reaches adulthood, for example, 8- to 12-weeks old, such as 12-weeks old, for mice.

In the present invention, endogenous CD3 gene(s) whose function is to be deleted may be any one or more types selected from the group consisting of CD3ε, CD3δ, and CD3γ, but for example, at least the endogenous CD3ε gene may be functionally deleted. It is also preferable to functionally delete two or more types thereof, for example, at least the endogenous CD3ε and CD3δ, the endogenous CD3ε and CD3γ, or the endogenous CD3δ and CD3γ are functionally deleted. Alternatively, all of the endogenous CD3ε, CD3δ, and CD3γ may be functionally deleted.

In the present invention, the phrase "functionally express human CD3 gene(s)" refers to the condition where human CD3 molecule(s) is/are expressed on T cells of non-human animals and immunocompetent cells including the T cells maintain normal functions in the non-human animals. Whether the immunocompetent cells maintain normal functions can be determined by using as indicators, for example, the differentiation process of T cells, maturation process of T cells, thymus weight, number of thymocytes, and the ratio of CD4-positive and CD8-positive cells among functional T cells in the spleen, in the non-human animals.

Preferably, the genetically modified non-human animals of the present invention have an ability of mature T cell differentiation and production. More specifically, in the present invention, functionally expressing human CD3 gene may mean that mature T cells are produced in such animals. For example, when the genetically modified non-human animals of the present invention are mice, preferably, their T cell differentiation and maturation processes are not affected and the thymus weight and the number of thymocytes are equivalent to those of a normal mouse. The number of thymocytes equivalent to that of a normal mouse means that the number of thymocytes in a genetically modified non-human animal is at least $1×10^4$ cells or more, preferably $1×10^5$ cells or more, $5×10^5$ cells or more, $1×10^6$ cells or more, $5×10^6$ cells or more, $1×10^7$ cells or more, or particularly preferably $5×10^7$ cells or more, and most preferably the number of thymocytes of a genetically modified non-human animal is in the range of $5×10^7$ to $6×10^7$ cells.

Furthermore, the ratio of cells positive for a surface marker for functional T cells, Cd4 or Cd8, is preferably equivalent to that of a normal mouse. Here, being equivalent to the ratios of Cd4- and Cd8-positive cells among mature T cells in a normal mouse means that when evaluated in the spleen, the ratio of Cd4-positive cells to the total number of mature T cells is preferably 10% to 40%, 12% to 38%, 14% to 36%, 16% to 34%, 18% to 32%, and particularly preferably 20% to 30%. Furthermore, the ratio of Cd8-positive cells to the total number of mature T cells is preferably 5% to 30%, 7% to 28%, 9% to 26%, 11% to 24%, 13% to 22%, and particularly preferably 15% to 20%.

In methods for evaluating the thymus weight, number of thymocytes, and abundance ratios of CD4-positive cells and CD8-positive cells in the periphery of a non-human animal, those skilled in the art can appropriately use, for example, well-known analysis methods, such as the analysis methods described in the following Examples, to conduct the evaluation.

Immunocompetent cells including T cells of the human CD3-substituted mice preferably have an equivalent cell proliferation ability after mitogen stimulation, as compared to those of wild-type mice. Being equivalent means that after mitogen stimulation the evaluated values of thymidine uptake, bromodeoxyuridine uptake, MTS assay, and 5-(and 6)-carboxyfluorescein diacetate succinimidyl ester (CFSE) assay are preferably 65% to 135%, 70% to 130%, 75% to 125%, 80% to 120%, and particularly preferably 85% to 115% of those of the wild-type.

In a non-limiting embodiment of the present invention, a genetically modified non-human animal of the present invention has increased ability to produce mature T cells as compared to a control that does not express the human CD3 genes (an animal deficient in the same combination of endogenous CD3 genes as that of the above-mentioned animal). More specifically, a total of CD4 single positive cells and CD8 single positive cells in the spleen is, for example, 1.3-times or more, preferably 1.5-times or more, more preferably 1.6-times or more, 2-times or more, 3-times or more, 4-times or more, 5-times or more, 10-times or more, 20-times or more, 50-times or more, or 100-times or more compared to that of the control. The developmental stage at which mature T cells are counted can be any stage as long as it is a stage at which mature T cells are produced in an animal of the present invention, preferably, the age when an animal typically reaches adulthood, for example, 8- to 12-weeks old, such as 12-weeks old, for mice.

Furthermore, the genetically modified non-human animals of the present invention have the ability to produce antibodies, for example, against foreign antigens. The types of antibodies are not particularly limited, and for example, it may be IgG (such as IgG1) or IgE. The foreign antigens are not particularly limited, and antibody production can be confirmed using a desired antigen, such as chicken ovalbumin (OVA).

In a non-limiting embodiment of the present invention, genetically modified non-human animals of the present invention has high antibody-producing ability as compared to a control that does not express the human CD3 genes (an animal deficient in the same combination of endogenous CD3 genes as that of the above-mentioned animals). Herein, the types of antibodies are not particularly limited, and for example, it may be IgG (such as IgG1) or IgE. Whether antibody-producing ability is increased can be determined by, following foreign antigen inoculation, observing whether antibodies are produced or measuring the amount of antibodies produced. The foreign antigen is not particularly limited, and antibody production can be confirmed using a desired antigen, for example, chicken ovalbumin (OVA). The antibody titer in the genetically modified non-human animals of the present invention is, for example, 1.3-times or more, preferably 1.5-times or more, more preferably 1.6-times or more, 2-times or more, 3-times or more, 4-times or more, 5-times or more, 10-times or more, 20-times or more, 50-times or more, or 100-times or more as compared to that of the control animal. The developmental stage at which antibody production is induced can be any stage as long as it is a stage at which antibodies are produced in an animal of the present invention, preferably, the age when an animal typically reaches adulthood, for example, 8- to 12-weeks old, such as 12-weeks old, for mice. The timing for antigen immunization and the timing for antibody measurement can be set appropriately, and for example, immunization can be performed twice with a four-week interval, where an initial immunization is performed by subcutaneously applying 100 μg of an antigen with complete Freund's adjuvant to the dorsal region, four weeks thereafter, a similar immunization is performed by subcutaneously applying the antigen with incomplete Freund's adjuvant to the dorsal region, then blood is collected one week after the second immunization, and the antibody titer can be measured.

Furthermore, in a non-limiting embodiment of the present invention, the condition where immunocompetent cells including T cells maintain normal functions includes a condition where functions relating to acquired immunity (humoral immunity, and cellular immunity) in the genetically modified non-human animals are kept normal.

In a non-limiting embodiment of the present invention, a genetically modified non-human animal of the present invention is a genetically modified non-human animal, in which a full-length nucleotide sequence of at least one or more types of human CD3 genes selected from the group consisting of human CD3ε, CD3δ, and CD3γ is inserted into the genome. Regarding the full-length nucleotide sequences to be inserted into the genome, the one or more types of CD3ε selected from the group consisting of human CD3ε, CD3δ, and CD3γ are not particularly limited, and the sequence may be for example, a full-length nucleotide sequence of human CD3ε. Furthermore, CD3ε may be two or more types of CD3ε selected from the group consisting of human CD3ε, CD3δ, and CD3γ and the sequences may be for example, a full-length nucleotide sequence of human CD3ε and a full-length nucleotide sequence of CD3δ, a full-length nucleotide sequence of human CD3ε and a full-length nucleotide sequence of CD3γ, or a full-length nucleotide sequence of human CD3δ and a full-length nucleotide sequence of CD3γ. The sequences may also be those of CD3ε comprising a full-length nucleotide sequence of human CD3ε, a full-length nucleotide sequence of CD3δ, and a full-length nucleotide sequence of CD3γ, i.e., all three types. In a non-limiting embodiment of the present invention, a "full-length nucleotide sequence" of a CD3 gene refers to a nucleotide sequence coding for a CD3 molecule (CD3ε, CD3δ, or CD3γ) including the extracellular, transmembrane, and cytoplasmic regions, and the nucleotide sequence may also include an expression regulatory region (promoter).

A non-limiting embodiment of the present invention provides genetically modified non-human animals, in which a non-human animal-derived T cell receptor and human CD3 molecule(s) form a complex on T cells carried by the above-mentioned genetically modified non-human animals.

Here, CD3ε forms a dimer with CD3δ or CD3γ, and then these dimers form a complex with the T cell receptor (TCR) α chain and the TCRβ chain, thereby forming a functional TCR complex. Without being bound to a particular theory, in genetically modified non-human animals of the present invention, human-derived CD3ε, CD3δ, and/or CD3γ can form a complex together with a non-human animal-derived TCR α chain and β chain on the T cells of the above-mentioned non-human animals.

In a non-limiting embodiment of the present invention, the above-mentioned genetically modified non-human animals of the present invention may be genetically modified non-human animals which further express human cancer-specific antigen gene, human immune checkpoint gene, and/or human immune costimulatory molecule gene. A human cancer-specific antigen refers to an antigen expressed by a cancer cell, which enables discrimination between cancer cells and healthy cells, and for example, it includes antigens that are expressed as cells become malignant or abnormal sugar chains that appear on the cell surfaces or on protein molecules when cells become cancerous. An "immune checkpoint" refers to a molecule that is expressed on immunocompetent cells and binds to a ligand to thereby transduce signals to the immunocompetent cells, which signals inhibit the cells' immune response. Examples of the immune checkpoints and their ligands include but are not limited to PD-1, CTLA-4, TIM3, LAG3, PD-L1, PD-L2, BTNL2, B7-H3, B7-H4, CD48, CD80, 2B4, BTLA, CD160, CD60, CD86, and VISTA. An "immune costimulatory molecule" refers to a molecule that is expressed on immunocompetent cells and binds to a ligand to thereby transduce signals that activate immune response caused by the immunocompetent cells. Examples of the immune costimulatory molecules include but are not limited to CD28, ICOS, CD137, CD137L, CD40, CD40L, OX40, OX40L, CD27, CD70, HVEM, LIGHT, RANK, RANKL, CD30, CD153, GITR, and GITRL. The above-mentioned genetically modified animals further expressing human cancer-specific antigen gene, human immune checkpoint gene, and/or human immune costimulatory molecule gene can be produced by appropriately using a method known to those skilled in the art, such as crossing a genetically modified animal expressing a human CD3 gene with a genetically modified animal expressing a human cancer-specific antigen gene, a human immune checkpoint gene, and/or a human immune costimulatory molecule, but not limited thereto.

In a non-limiting embodiment, examples of the non-human animals functionally expressing human CD3 genes of the present invention are the genetically modified non-human animals disclosed in WO2017/010423 and WO2016/085889. Examples of the method for producing the non-human animals functionally expressing human CD3 genes are the methods disclosed in WO2017/010423 and WO2016/085889.

9. Non-Human Animals which Express a Human GPC3 Polypeptide and Functionally Express Human CD3 Genes The present invention also relates to non-human animals which express a human GPC3 polypeptide and also functionally express human CD3 genes.

In a non-limiting embodiment, the non-human animal of the present invention which expresses a human GPC3 polypeptide and functionally expresses human CD3 genes is a genetically modified non-human animal which:
(i) is deficient in expression of an endogenous GPC3 polypeptide and expresses a human GPC3 polypeptide; and
(ii) is functionally deficient in at least one or more types of CD3 genes selected from the group consisting of endogenous CD3ε, CD3δ, and CD3γ in its genome, and functionally expresses at least one or more types of human CD3 genes selected from the group consisting of human CD3ε, human CD3δ, and human CD3γ.

In a non-limiting embodiment, the non-human animal of the present invention which expresses a human GPC3 polypeptide and functionally expresses human CD3 genes can be obtained by crossing a non-human animal expressing the human GPC3 polypeptide disclosed herein with a non-human animal functionally expressing the human CD3 genes disclosed herein. In doing so, whether the non-human animal of interest is obtained can be determined by crossing a non-human animal expressing the human GPC3 polypeptide with a non-human animal functionally expressing the human CD3 genes, analyzing the genotype of the obtained next generation individual, and confirming the transmission of the human GPC3 knock-in allele, an allele deficient in the non-human CD3 gene region, and an allele carrying the human CD3 gene region.

10. Methods for Evaluating Test Substances Using Non-Human Animals which Express a Human GPC3 Polypeptide and Functionally Express Human CD3 Genes In a non-limiting embodiment, the non-human animal of the present invention which expresses a human GPC3 polypeptide and functionally expresses human CD3 genes can be used in various evaluations of test substances for their safety, therapeutic effects on a disease, pharmacokinetics, in vivo distribution, or such. Accordingly, the present invention also provides methods for evaluating a test substance using such non-human animals. In another embodiment, the present invention includes a non-human animal for use in various evaluations of test substances for their safety, therapeutic effects on a disease, pharmacokinetics, in vivo distribution, or such, and/or screening. Furthermore, in another embodiment, the present invention includes use of a non-human animal expressing a human GPC3 polypeptide and functionally expressing human CD3 genes for use in various evaluations of test substances for their safety, therapeutic effects on a disease, pharmacokinetics, in vivo distribution, or such, and/or screening.

The test substances to be used in the evaluation methods are not particularly limited to the following, but are preferably human GPC3-binding peptides, proteins, non-peptide compounds, synthetic compounds, fermentation products, cells, cell extracts, antibodies, or antibody fragments or human CD3-binding peptides, proteins, non-peptide compounds, synthetic compounds, fermentation products, cells, cell extracts, antibodies, or antibody fragments. Preferably, they are human GPC3-binding antibodies or human CD3-binding antibodies, and more preferably multispecific antibodies that bind to human GPC3 and human CD3. Examples of multispecific antibodies that bind to human GPC3 and human CD3 include known antibodies described in WO2016/047722.

Furthermore, it is possible to carry out various evaluation methods disclosed herein as "methods for evaluating test substances using a non-human animal expressing a human GPC3 polypeptide" by using a non-human animal which expresses a human GPC3 polypeptide and functionally expresses human CD3 genes, as a matter of course.

11. Antigen-Binding Molecules

"Antigen-binding molecules" as used herein are not particularly limited as long as they are molecules containing an antigen-binding domain, and they may further contain a peptide or protein having a length of approximately five amino acids or more. The molecules are not limited to biologically derived peptides and proteins, and may be, for example, polypeptides comprising an artificially designed sequence. Furthermore, they may be any of naturally-occurring polypeptides, synthetic polypeptides, recombinant polypeptides, or such.

In a non-limiting embodiment, preferred examples of the antigen-binding molecules include antigen-binding molecules comprising an FcRn-binding domain included in Fc regions of antibodies. As a method for extending the blood half-life of a protein administered to a living organism, the method of adding an antibody FcRn-binding domain to the protein of interest and utilizing the function of FcRn-mediated recycling is well known. In another embodiment, preferred examples of antigen-binding molecules include antibodies.

12. Antibodies

Herein, an "antibody" refers to a naturally occurring immunoglobulin or an immunoglobulin produced by partial or complete synthesis, or fragments thereof. Antibodies can be isolated from natural sources such as plasma and serum where antibodies are naturally-occurring, or culture supernatants of antibody-producing hybridoma cells. Alternatively, antibodies can be partially or completely synthesized using techniques such as genetic recombination. Suitable examples of the antibodies include antibodies of an immunoglobulin isotype or subclass of such isotype. Known human immunoglobulins include those of the following nine classes (isotypes): IgG1, IgG2, IgG3, IgG4, IgA1, IgA2, IgD, IgE, and IgM. Of these isotypes, antibodies of the present invention can include IgG1, IgG2, IgG3, and IgG4.

In a non-limiting embodiment, antibodies provided herein are chimeric antibodies. Certain chimeric antibodies are described, for example, in U.S. Pat. No. 4,816,567 and Morrison et al., Proc. Natl. Acad. Sci. USA, 81:6851-6855 (1984). In one example, a chimeric antibody comprises non-human variable regions (for example, variable regions derived from a mouse, rat, hamster, rabbit, or a non-human primate such as a monkey) and human constant regions. In a further example, a chimeric antibody is a "class-switched" antibody in which the class or subclass has been changed from that of the parent antibody. Chimeric antibodies also include antigen-binding fragments thereof.

In a non-limiting embodiment, antibodies provided herein are humanized antibodies. Humanized antibodies and methods for producing them are reviewed, for example, in Almagro and Fransson, Front. Biosci. 13:1619-1633 (2008), and these antibodies can be produced by various techniques known in the art.

In a non-limiting embodiment, antibodies provided herein are human antibodies. Human antibodies can be produced by various techniques known in the art. Human antibodies is described generally in van Dijk and van de Winkel, Curr. Opin. Pharmacol. 5: 368-74 (2001) and Lonberg, Curr. Opin. Immunol. 20:450-459 (2008).

Antibodies of the present invention can be isolated by screening combinatorial libraries for antibodies having one or more of desired activities. For example, various methods are known in the art for generating phage display libraries and screening such libraries for antibodies possessing the desired binding properties. Such methods are reviewed, for example, by Hoogenboom et al. in Methods in Molecular Biology 178:1-37, and O'Brien et al., ed., Human Press, Totowa, NJ, 2001.

In certain embodiments, antibodies provided herein are multispecific antibodies (for example, bispecific antibodies). Multispecific antibodies are monoclonal antibodies that have binding specificities for at least two different sites. Techniques for producing multispecific antibodies include, but are not limited to, recombinant co-expression of two immunoglobulin heavy chain-light chain pairs having different specificities (see Milstein and Cuello, Nature 305: 537 (1983), WO 93/08829, and Traunecker, et al., EMBO J. 10:3655 (1991)), and "knob-in-hole" technique (see, for example, U.S. Pat. No. 5,731,168). Multispecific antibodies may also be produced by engineering electrostatic steering effects for producing Fc-heterodimeric molecules (WO 2009/089004A1); crosslinking two or more antibodies or fragments (see U.S. Pat. No. 4,676,980, and Brennan et al., Science 229:81 (1985)); using leucine zippers to produce bispecific antibodies (see Kostelny et al., J. Immunol., 148(5):1547-1553 (1992); using "diabody" technology for producing bispecific antibody fragments (see Holliger et al., Proc. Natl. Acad. Sci. USA 90:6444-6448 (1993)); using single-chain Fv (scFv) dimers (see Gruber et al., J. Immunol. 152:5368 (1994)); and preparing trispecific antibodies as described, for example in Tutt et al., J. Immunol. 147:60 (1991).

Modified antibodies with three or more functional antigen binding sites, including "octopus antibodies" are also included in the antibodies herein (see, for example, US Patent Application No. 2006/0025576-A1).

The antibody or fragment herein also includes a "dual acting Fab" or "DAF" comprising an antigen binding site that binds to a certain antigen as well as another, different antigen (see, for example, US Patent Application No. 2008/0069820).

In certain embodiments, the antibody or antibody fragment has a sequence including substitutions (for example, conservative substitutions), insertions, or deletions relative to a reference sequence, and includes post-translational modification of that sequence. Post-translational modifications include but are not limited to a modification of glutamine or glutamic acid in N-terminal of heavy chain or light chain to pyroglutamic acid by pyroglutamylation.

EXAMPLES

Herein below, the present invention will be specifically described with reference to the Examples, but the present invention is not to be construed as being limited to the following Examples.

Example 1: Production of Human GPC3 Knock-in Mouse (1) Construction of Knock-in Vector For hGPC3 knock-in (hGPC3KI) vector ver. 1, an artificial chromosome (bacterial artificial chromosome (BAC)) clone was used, into which the genomic region of the mouse glypican-3 gene (mGpc3) was cloned. The coding sequence (SEQ ID NO: 10) of the human glypican-3 gene (hGpc3), an hp7 sequence (SEQ ID NO: 11), a polyadenylation signal (SEQ ID NO: 12), loxP sequences (SEQ ID NO: 7), and a neomycin resistance (neo) gene (SEQ ID NO: 13) were introduced to the target region of the Gpc3 gene on the BAC clone through homologous recombination using Red/ET System (Gene Bridge). In the introducing, the translation initiation site of hGPC3 was inserted such that it comes to the very position where the translation initiation site of mGpc3 was. The construct of the vector is shown in FIG. 1(2).

For hGPC3KI vector ver. 2, the approximately 800-bp 5' upstream region of the mGpc3 gene target region; the mouse beta globin second exon (SEQ ID NO: 14), intron (SEQ ID NO: 15), and third exon (SEQ ID NO: 16); hGPC3 gene-coding sequence; the polyadenylation signal in the third exon of mouse beta globin; loxP sequences; neo gene; and the approximately 800-bp 3' downstream region of the mouse Gpc3 gene target region were inserted into the plasmid vector. The construct of the vector is shown in FIG. 1(3).

For hGPC3KI vector ver. 3, the approximately 800-bp 5' upstream region of the mGpc3 gene target region; the mouse beta globin second exon, intron, and third exon; hGPC3 gene-coding sequence; 3' untranslated region of the mGpc3 gene (SEQ ID NO: 17); and the approximately 800-bp 3' downstream region of the mGpc3 gene target region were inserted into the plasmid vector. The construct of the vector is shown in FIG. 1(4).

(2) Designing a Zinc Finger Nuclease (ZFN)

ZFN was designed so that it causes a double strand break (DSB) in the gene near the translation initiation site of the mGpc3 gene. ZFN is a fusion protein in which a protein capable of binding to some specific sequence is linked to a nuclease capable of causing a double strand break in a gene. By binding to a specific sequence, ZFN repeatedly causes DSB at that site. Since DSB induces homologous recombination, repeated DSB at the target region can increase the efficiency of inserting a foreign gene into the target region.

(3) Introduction of hGPC3KI Vector Ver. 1 and hGPC3KI Vector Ver. 2 into ES Cells hGPC3KI vector ver. 1 was introduced into embryonic stem (ES) cells of C57BL(B6) by electroporation, and drug resistant clones obtained after selective culture using G418 were screened for homologous recombinants by PCR.

hGPC3KI vector ver. 2 was introduced into ES cells by electroporation together with a ZFN mRNA or a ZFN plasmid vector that cleaves the target sequence, and drug resistant clones obtained after selective culture using G418 were screened for homologous recombinants by PCR.

In the screening, a genome extracted from the drug-resistant clone was used as a template for PCR.

The composition of the PCR reaction solution for the screening of hGPC3KI vector ver. 1 was made up of 1 μL of the sample, 12.5 μL of 2×GC buffer, 4 μL of dNTP (2.5 mM), 0.1 μL each of the primers (50 μM each), 0.25 μL of LA Taq (TAKARA), and 7.05 μL of distilled water (25 μL in total). The PCR conditions included preheating at 94° C. for five minutes, 35 cycles of an amplification cycle of 94° C. for 30 seconds, 58° C. for 30 seconds, and 72° C. for five minutes and 30 seconds, and additional heating at 72° C. for seven minutes. The primers used were forward primer [5'-AGATGGCTGCCTGTGACATTTCTGGAAGTGT-3' (SEQ ID NO: 18)] and reverse primer [5'-CTGAATTAGTTCCCTTCTTCGGCTGGATAA-3' (SEQ ID NO: 19)]. Using these primers, amplification of an approximately 5.5-kb band was expected provided that hGPC3KI vector ver. 1 was inserted into the same reading frame as that of the mouse endogenous GPC3 gene.

The composition of the PCR reaction solution for the screening of hGPC3KI vector ver. 2 was prepared in the same manner as the composition of the PCR reaction solution for the screening of hGPC3KI vector ver. 1. The PCR conditions included preheating at 94° C. for five minutes, 35 cycles of an amplification cycle of 94° C. for 30 seconds, 58° C. for 30 seconds, and 72° C. for three minutes, and additional heating at 72° C. for seven minutes. The primers used were forward primer [5'-ATGAGACCCAGCAAGCTACACGGGCT-3' (SEQ ID NO: 20)] and reverse primer [5'-ACTTGAGCTCCATACTTGCAGACT-3' (SEQ ID NO: 21)]. Using these primers, amplification of an approximately 2-kb band was expected provided that hGPC3KI vector ver. 2 was inserted into the same reading frame as that of the mouse endogenous GPC3 gene.

Figure 3:
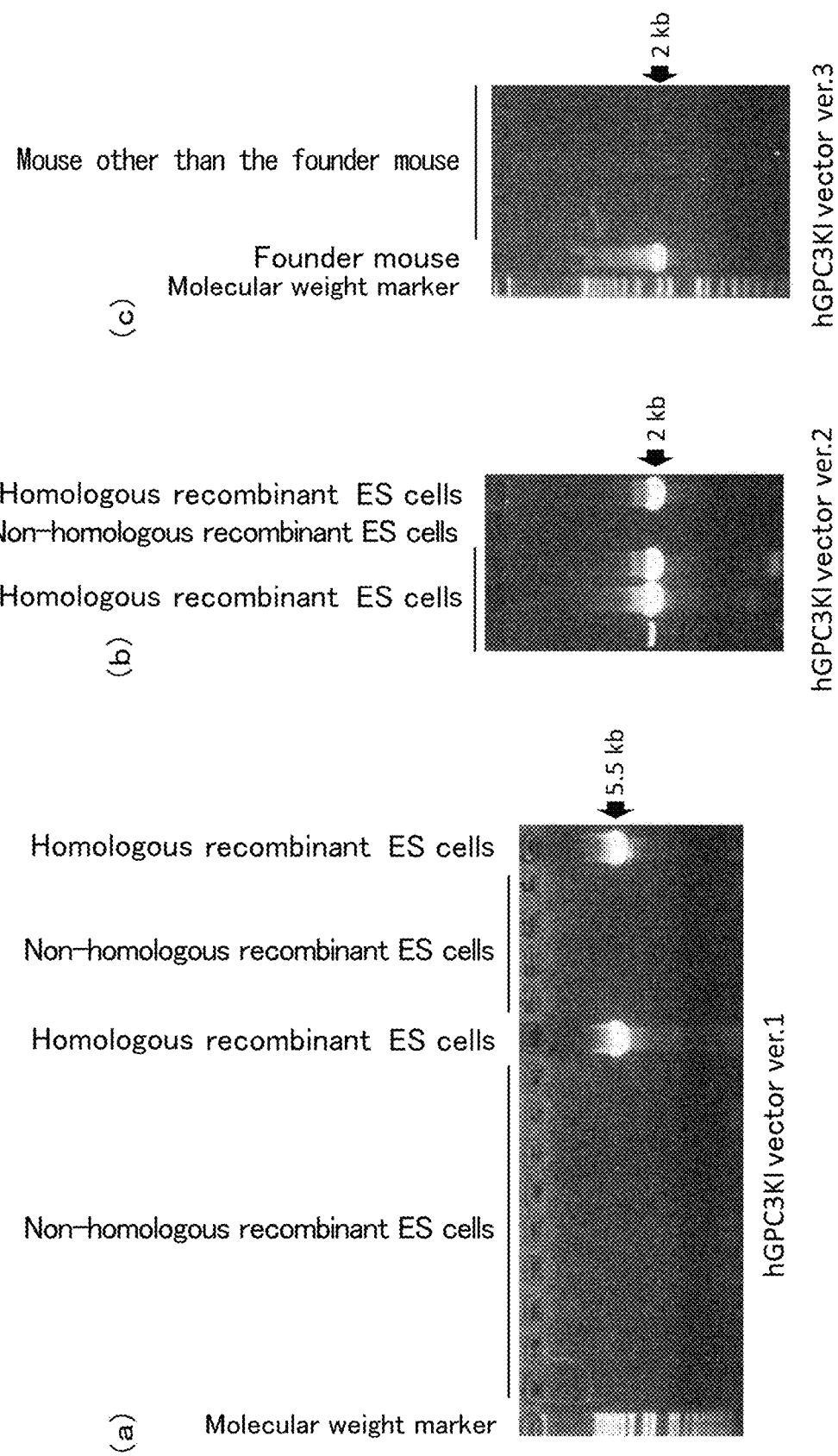
FIG. 3 presents the representative examples of PCR analyses performed to screen for homologous recombinant ES cells generated with hGPC3 knock-in vector ver. 1 and homologous recombinant ES cells generated with hGPC3 knock-in vector ver. 2 [hGPC3 knock-in vector ver. 1 (a) and hGPC3 knock-in vector ver. 2 (b)], and the representative example of PCR analyses (c) performed to detect founder mice carrying the hGPC3 knock-in vector ver. 3 gene.

In samples of the ES cells in which homologous recombination with hGPC3KI vector ver. 1 occurred, an approximately 5.5-kb band was amplified by the above-mentioned PCR reaction (FIG. 3(a)). Furthermore, in samples of the ES cells in which homologous recombination with hGPC3KI vector ver. 2 occurred, an approximately 2-kb band was amplified (FIG. 3(b)).

(4) Production of hGPC3KI Mouse Ver. 1 and hGPC3KI Mouse Ver. 2

The homologous recombinant ES clones generated with hGPC3KI vector ver. 1 and hGPC3KI vector ver. 2 were suspended by trypsin treatment, and washed with the ES cell medium. Female BALB/c mice which were subjected to superovulation treatment by administering 5 IU of equine chorionic gonadotropin (eCG) and human chorionic gonadotropin (hCG) intraperitoneally at 48-hour intervals were crossed with male mice of the same strain. The day when a plug was confirmed in a female mouse was regarded as day 0.5. On gestation day 3.5, blastocyst-stage embryos collected by perfusing the uterus were used as host embryos, in which 10 to 15 of the ES cells were injected. The embryos after the injection were transferred into the uterus of ICR recipient females on day 2.5 pseudopregnancy, and their offspring were obtained. Chimeric mice were yielded by injection of the ES cells to the blastocyst-stage embryos. After sexual maturation, the male chimeric mice were crossed with B6-female mice, and transmission of the knock-in allele to the next generation was confirmed by a PCR method. PCR was performed by the method described in Example 1(3). As a result, animals from which an approximately 5.5-kb signal and an approximately 2-kb signal were detected for hGPC3KI mouse ver. 1 and hGPC3KI mouse ver. 2, respectively were yielded, and the knock-in alleles were confirmed to be transmitted to these animals.

(5) Production of hGPC3KI Mouse Ver. 3

Production of a knock-in mouse using hGPC3KI vector ver. 3 was carried out by introducing KI vector ver. 3 and ZFN into fertilized eggs. KI vector ver. 3 and ZFN mRNA were injected by microinjection into the pronuclei of fertilized eggs collected from B6 mice. Among the fertilized eggs injected with KI vector ver. 3 and ZFN, those that developed to two-cell stage embryos were transferred into the fallopian tubes of ICR (recipient mice). Founder mice carrying the hGPC3KI vector ver. 3 gene were screened for by PCR from among the obtained mice. The PCR reaction composition was prepared in the same manner as that of Example 1(3), and the primers and PCR conditions used were the same as those of the screening for hGPC3KI vector ver. 2 described in Example 1(3). As a result, founder mice from which an approximately 2-kb signal was detected were yielded (FIG. 3(c)). After sexual maturation, the obtained founder mice were crossed with B6-female mice, and transmission of the knock-in allele to the next generation mice was confirmed.

(6) Removal of Neo Gene

Figure 2:
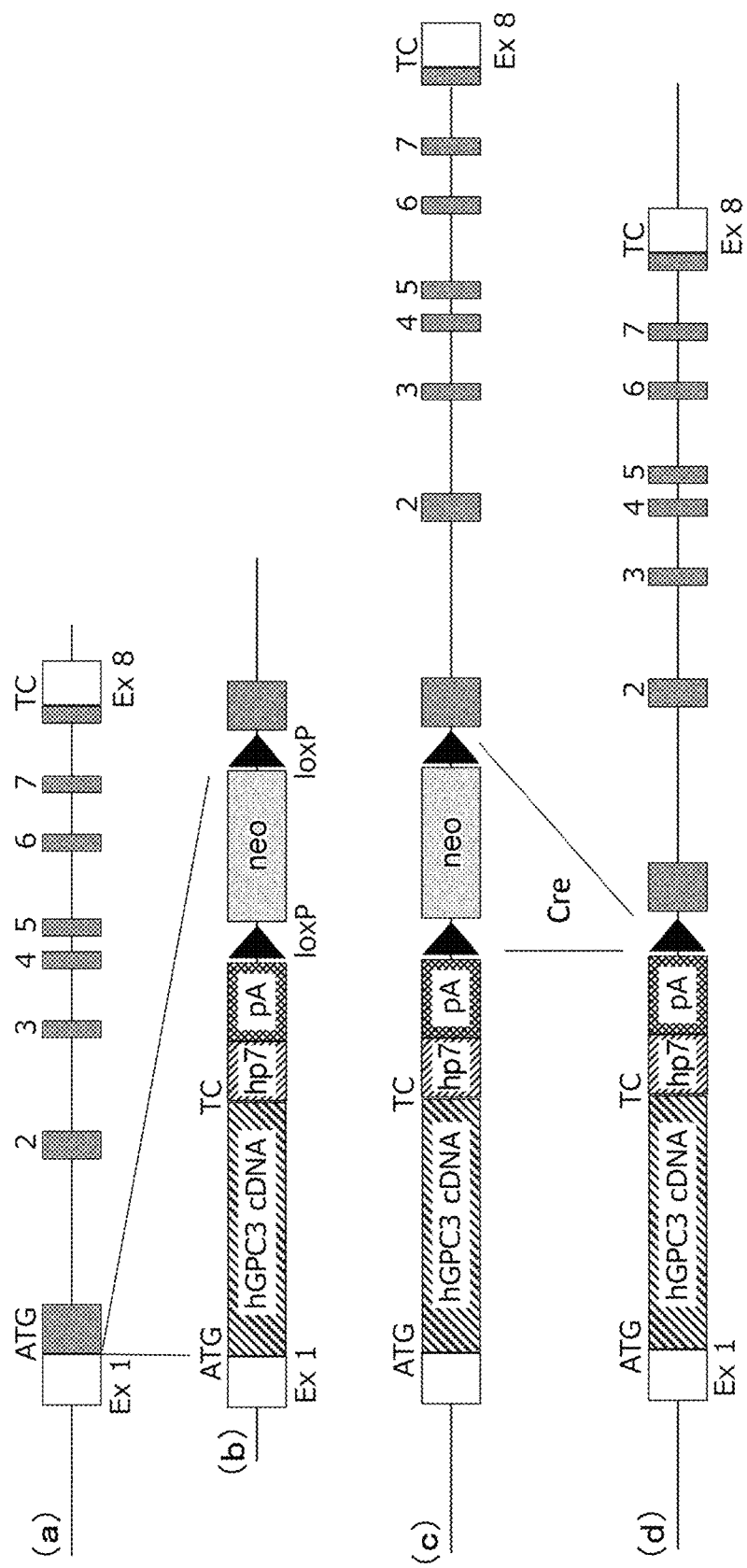
FIG. 2 presents a method of insertion (c) of knock-in vector ver. 1 (b) into a genomic DNA of the mGpc3 gene (a) by homologous recombination. It presents a process of subsequently removing the neomycin resistance gene (neo) flanked by loxPs using recombinase Cre to thereby complete a hGPC3 knock-in allele (d). Neo is removed from knock-in vector ver. 2 by a similar method.

The pronuclei of the fertilized eggs obtained by the breeding of the hGPC3KI mice ver. 1 and hGPC3KI mice ver. 2 that were confirmed to contain the transmitted knock-in allele was microinjected with a Cre recombinase circular expression vector to thereby remove the neo gene cassette. Specifically, transiently expressed Cre induces the recombination between the two loxPs positioned in the knock-in allele to remove the neo gene cassette (see FIG. 2). The fertilized eggs after the microinjection of the Cre expression vector were transferred into the fallopian tubes of ICR female recipients on day 0.5 pseudopregnancy. After 19 days, the offspring were obtained. The removal of the neo gene cassette was confirmed by PCR using a genomic DNA obtained from the offspring after weaning. PCR was performed using a PCR reaction composition prepared in the same manner as the composition in Example 1(3). The PCR conditions included preheating at 94° C. for five minutes, 35 cycles of an amplification cycle of 94° C. for 30 seconds, 58° C. for 30 seconds, and 72° C. for two minutes, and additional heating at 72° C. for seven minutes. The primers used were forward primer [5'-TGATGATGAAG ATGAGTGCAT-TGGA-3' (SEQ ID NO: 22)] and reverse primer [5'-TGGCCAGAACTA CGGGTCCAGCT-3' (SEQ ID NO: 23)].

For hGPC3KI mice ver. 1, the amplification product derived from the knock-in allele was detected as a signal of approximately 2.5 kb, whereas for samples of the animals after removal of the neo cassette, a signal of approximately 1 kb was detected (FIG. 4(a)). On the other hand, for hGPC3KI mice ver. 2, the amplification product derived from the knock-in allele was detected as a signal of approximately 3 kb, whereas for samples of the animals after removal of the neo cassette, a signal of approximately 1.6 kb was detected (FIG. 4(b))

(7) Establishment of hGPC3KI Mouse Ver. 1, hGPC3KI Mouse Ver. 2, and hGPC3KI Mouse Ver. 3

Animals which are homozygous and hemizygous for the knock-in allele were obtained by breeding hGPC3KI mice ver. 1 and hGPC3KI mice ver. 2 in which removal of the neo gene cassette has been confirmed. Similarly, animals which are homozygous and hemizygous for the knock-in allele were obtained by intercrossing hGPC3KI mice ver. 3 in which transmission of the knock-in allele to the next generation has been confirmed. The homozygote and hemizygote were confirmed by PCR. PCR was performed using a PCR reaction composition prepared in the same manner as the composition in Example 1(3).

The PCR conditions for hGPC3KI mice ver. 1 included preheating at 94° C. for five minutes, 35 cycles of an amplification cycle of 94° C. for 30 seconds, 58° C. for 30 seconds, and 72° C. for 15 seconds, and additional heating at 72° C. for seven minutes. The PCR conditions for hGPC3KI mice ver. 2 included preheating at 94° C. for five minutes, 35 cycles of an amplification cycle of 94° C. for 30 seconds, 58° C. for 30 seconds, and 72° C. for two minutes, and additional heating at 72° C. for seven minutes. The PCR conditions for hGPC3KI mice ver. 3 consisted of preheating at 94° C. for five minutes, 35 cycles of an amplification cycle of 94° C. for 30 seconds, 58° C. for 30 seconds, and 72° C. for 20 seconds, and additional heating at 72° C. for seven minutes.

The primers used for hGPC3KI mice ver. 1 and hGPC3KI mice ver. 3 were forward primer 1 [5'-AGGGCCCT-GAGCCAGTGGTCAGT-3' (SEQ ID NO: 24)], forward primer 2 [5'-TAGCGGCTCCTCTCTTGCTCTGT-3' (SEQ ID NO: 25)] and reverse primer [5'-GCCCGGGG-CATGTGGACAGAGTCCCATACT-3' (SEQ ID NO: 26)]. The primers used for hGPC3KI mice ver. 2 were the primers used in screening for hGPC3KI vector ver. 2 in Example 1(3).

Figure 5:
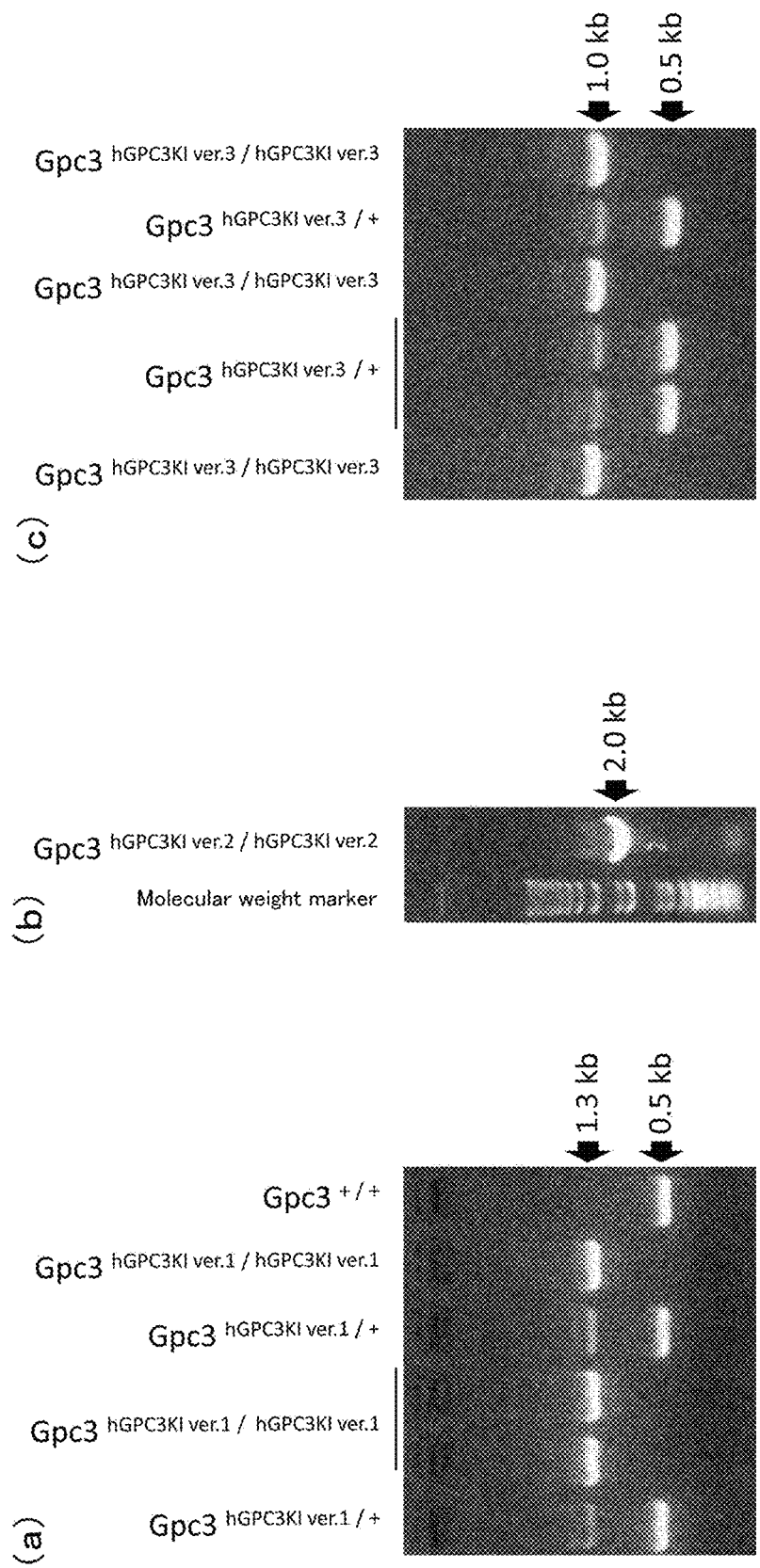
FIG. 5 presents the representative examples of PCR performed to detect homozygous and hemizygous hGPC3 knock-in mice ver. 1, hGPC3 knock-in mice ver. 2, and hGPC3 knock-in mice ver. 3 [hGPC3 knock-in mice ver. 1 (a), hGPC3 knock-in mice ver. 2 (b), and hGPC3 knock-in mice ver. 3 (c)]. hGPC3KI/hGPC3KI, hGPC3KI/−, hGPC3KI/+, and +/+ indicate homozygous knock-in mouse, hemizygous knock-in mouse, heterozygous knock-in mouse, and wild-type mouse, respectively.

The signal of approximately 1.3 kb derived from the knock-in allele is detected in the homozygous or hemizygous hGPC3KI mouse ver. 1, whereas the signal of approximately 0.5 kb derived from the wild-type allele is not detected therein. This feature was used as an indicator to confirm the homozygote and hemizygote (FIG. 5(a)). On the other hand, hGPC3KI mice ver. 2 were confirmed using a primer for detecting the hemizygote at approximately 2 kb (FIG. 5(b)). The signal of 1 kb derived from the knock-in allele is detected in the homozygous or hemizygous of hGPC3KI mice ver. 3, whereas the signal of 0.5 kb derived from the wild-type allele is not detected therein. This feature was used as an indicator to confirm the homozygote and hemizygote (FIG. 5(c)).

Example 2: Expression Analyses of hGPC3KI Mice (1) Confirmation of Protein Expression Expression of each GPC3 protein was confirmed by Western blotting using lung lysates of hGPC3KI mice and wild-type mice. The lung lysates of hGPC3KI mice and wild-type mice were prepared from one of the two lungs. To prepare samples for SDS-PAGE, a sample buffer (nacalai, catalogue no.) was added to each lung lysate, then heated at 95° C. for five minutes, and diluted to adjust the total amount of protein per lane to 50 μg to 450 μg. After fractionation by SDS-PAGE, proteins were transferred to a membrane. Detection was carried out by using an anti-human GPC3 antibody as the primary antibody, and an HRP-labeled anti-human IgG antibody as the secondary antibody. Tubulin alpha was used as the internal standard of the lysate, and detected using an anti-tubulin alpha antibody as the primary antibody, and an HRP-labeled anti-rat IgG antibody as the secondary antibody.

Figure 6:
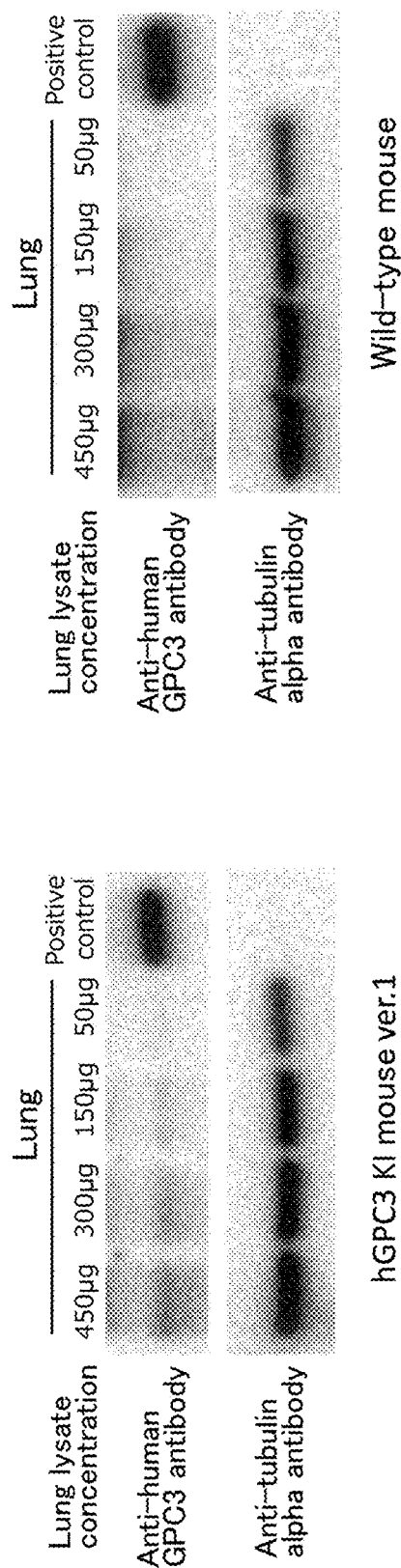
FIG. 6 presents the Western blotting results for the lungs of hGPC3 knock-in mice ver. 1 and wild-type mice, using an anti-human GPC3 antibody. Lysate concentration refers to total protein weight of the lung lysate applied to each lane.
Figure 7:
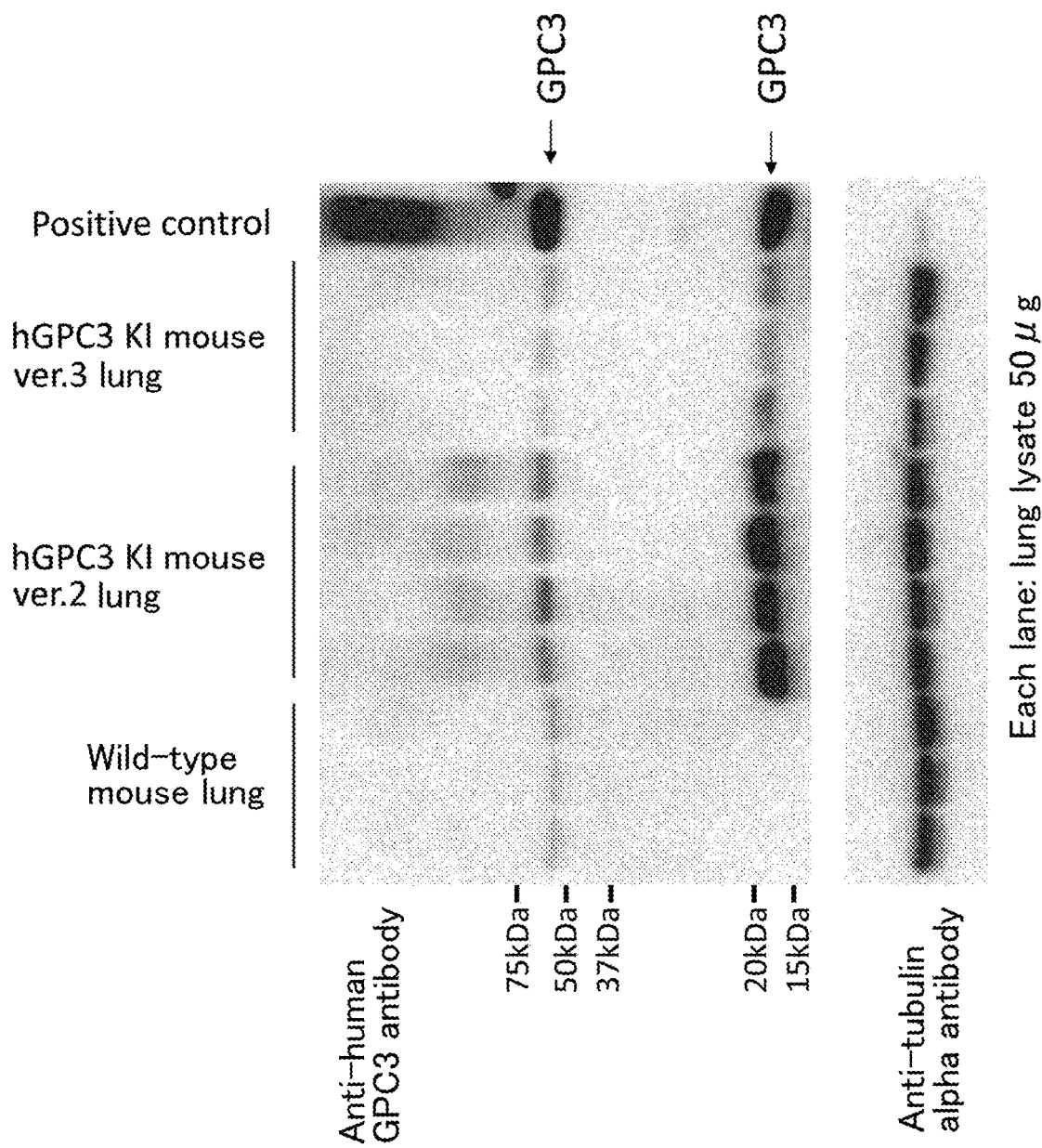
FIG. 7 presents the Western blotting results for the lungs of hGPC3 knock-in mice ver. 2, hGPC3 knock-in mice ver. 3, and wild-type mice, using an anti-human GPC3 antibody.

For hGPC3KI mice ver. 1, hGPC3 protein signal was hardly detected when using the lung lysate for 50 μg, but by increasing the lysate concentration, the detected signal intensity increased in a lysate concentration-dependent manner (FIG. 6). On the other hand, in lung lysates of hGPC3KI mice ver. 2 and hGPC3KI mice ver. 3, the hGPC3 protein signal was detected at 50 µg (FIG. 7). Since GPC3 usually undergoes processing, proteins with several different molecular weights are present. Among them, when using the anti-human GPC3 antibody used as the primary antibody, the GPC3 protein is detected near approximately 20 kDa and approximately 60 kDa. For the wild-type mice, a weak signal at a size equivalent to that of the positive control was detected near 60 kDa, but there was no signal detected near 20 kDa. Therefore, the signal detected near 60 kDa is very likely to be a nonspecific signal. Comparison of hGPC3KI ver. 2 and ver. 3 showed that both the 60-kDa and 20-kDa signals indicate higher expression levels for hGPC3KI ver. 2 than for ver. 3. On the other hand, the expression level of hGPC3KI ver. 1 was remarkably lower compared to those of hGPC3KI ver. 2 and ver. 3.

(2) Confirmation of mRNA Expression

Expression levels of each glypican-3 mRNA was analyzed by real-time PCR using lung total RNAs of hGPC3KI mice, wild-type mice, cynomolgus monkeys, and humans. Total RNAs were prepared from one of the two lungs of hGPC3KI mice and wild-type mice. For cynomolgus monkeys, total RNA of a portion of the bronchiole of the lung was prepared. Furthermore, for comparison of hGPC3KI mice ver. 3 with humans, total RNA samples were prepared by separating the lung of ver. 3 into accessory lobe, anterior lobe, middle lobe, posterior lobe, and the left lung. The amount of each of the obtained total RNA was determined by measuring the absorbance at 260 nm. For human lung total RNA, that purchased from Clontech was used.

Figure 8:
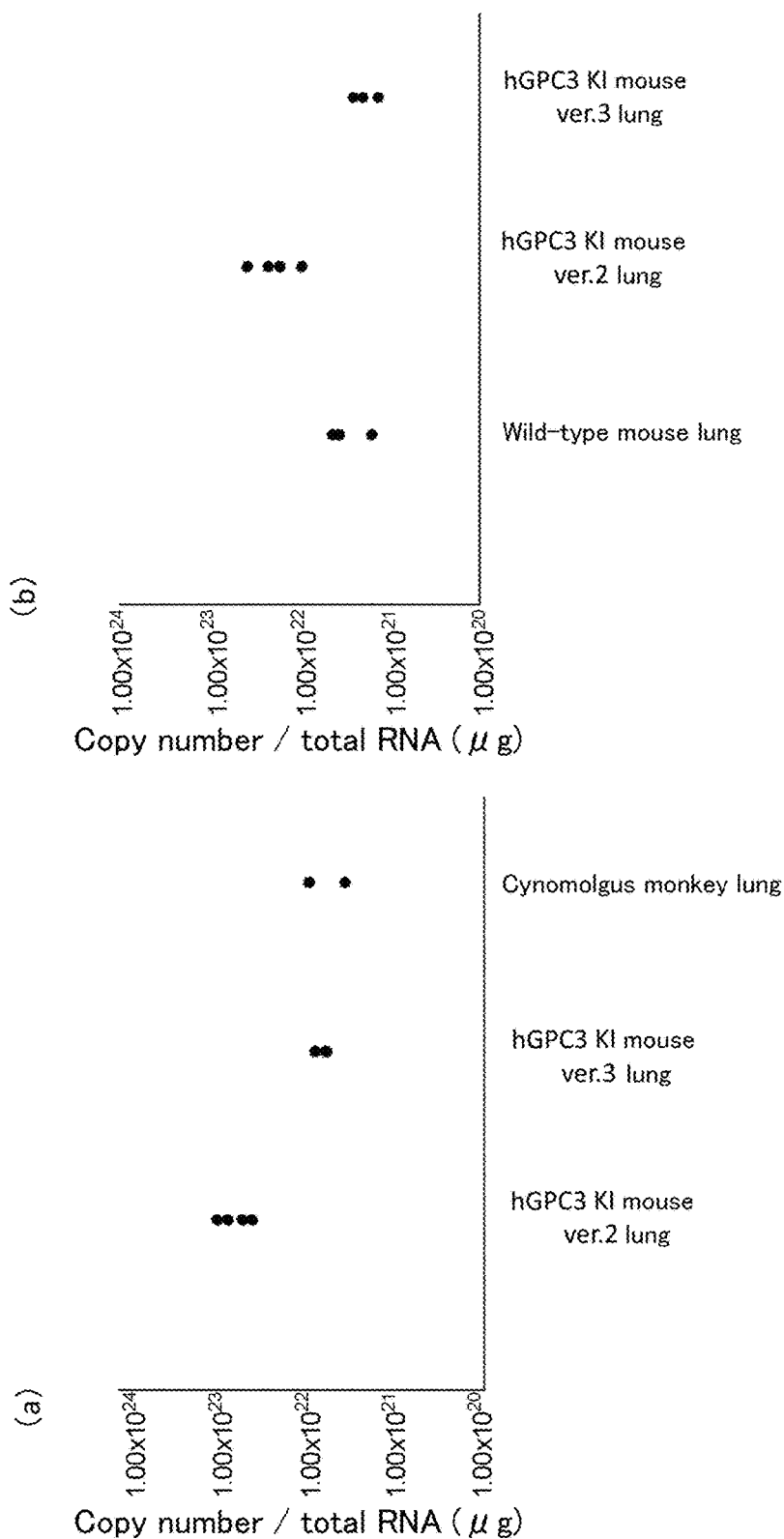
FIG. 8 shows graphs presenting the GPC3 mRNA expression levels in the lungs of hGPC3 knock-in mice ver. 2 and ver. 3, wild-type mice, and cynomolgus monkeys: (a) presents the results for hGPC3 knock-in mice ver. 2 and ver. 3, and cynomolgus monkeys, using Universal Probe #46; and (b) presents the results for wild-type mice, and ver. 2 and ver. 3, using Universal Probe #28.

The cDNAs used for comparison of hGPC3KI mice with monkeys (FIG. 8($a$)) and wild-type mice with hGPC3KI mice (FIG. 8($b$)) were synthesized by reverse transcription reaction using a Super Script III First-Strand Synthesis System for RT-PCR (Invitrogen) and using 2.5 µg each of the total RNAs as templates. The cDNA used for comparison of hGPC3KI mice ver. 3 with humans (FIG. 9) were synthesized by reverse transcription reaction using a Super Script VILO cDNA Synthesis Kit (Invitrogen) and using 0.5 µg each of the total RNAs as templates. Each glypican-3 was detected by real-time PCR using the synthesized cDNA as the template.

With regard to primers used for detection, for comparison among hGPC3KI mice, monkeys, and humans, primers were designed against the protein coding regions. The combination of primers used were forward primer [5'-GAAACCT-TATCCAGCCGAA GA-3' (SEQ ID NO: 27)] and reverse primer [5'-GCAAAGGGTGTCGTTTTCC-3' (SEQ ID NO: 28)]. For comparison of hGPC3KI mice with wild-type mice, primers were designed against the 5' untranslated region of the mGpc3 gene. The combination of primers used were forward primer [5'-CAGGTAGCTGCGAGGAAACT-3' (SEQ ID NO: 29)] and reverse primer [5'-CCGACAGAGCAAGAGAGGAG-3' (SEQ ID NO: 30)]. Analyses were carried out by the absolute quantification method. For comparison of hGPC3KI mice with monkeys and of wild-type mice with hGPC3KI mice, hGPC3 cDNA-inserted plasmids that are adjusted to the range of $2.2 \times 10^{16}$ to $2.2 \times 10^{23}$ were used to prepare calibration curve; for comparison of hGPC3KI mice ver. 3 with humans, hGPC3 cDNA-inserted plasmids that are adjusted to the range of $1.0 \times 10$ to $1.0 \times 10^8$ were used to prepare calibration curve; and the copy number of glypican-3 mRNA in each of the lung tissues was calculated.

The composition of the real-time PCR reaction solution was made up of 1 µL of the sample, 5 µL of Fast Start Universal Probe Master (Roche), 0.2 µL of Universal Probe (Roche), 0.2 µL each of the primers (10 µM each), and 3.4 µL of distilled water (10 µL in total). Regarding the Universal Probe, Universal Probe #46 (Roche) was used for comparison among hGPC3KI mice, monkeys, and humans, and Universal Probe #28 (Roche) was used for comparison of hGPC3KI mice with wild-type mice.

The PCR conditions included preheating at 50° C. for two minutes and 95° C. for ten minutes, followed by 50 cycles of an amplification cycle of 95° C. for 15 seconds and 60° C. for one minute.

Figure 9:
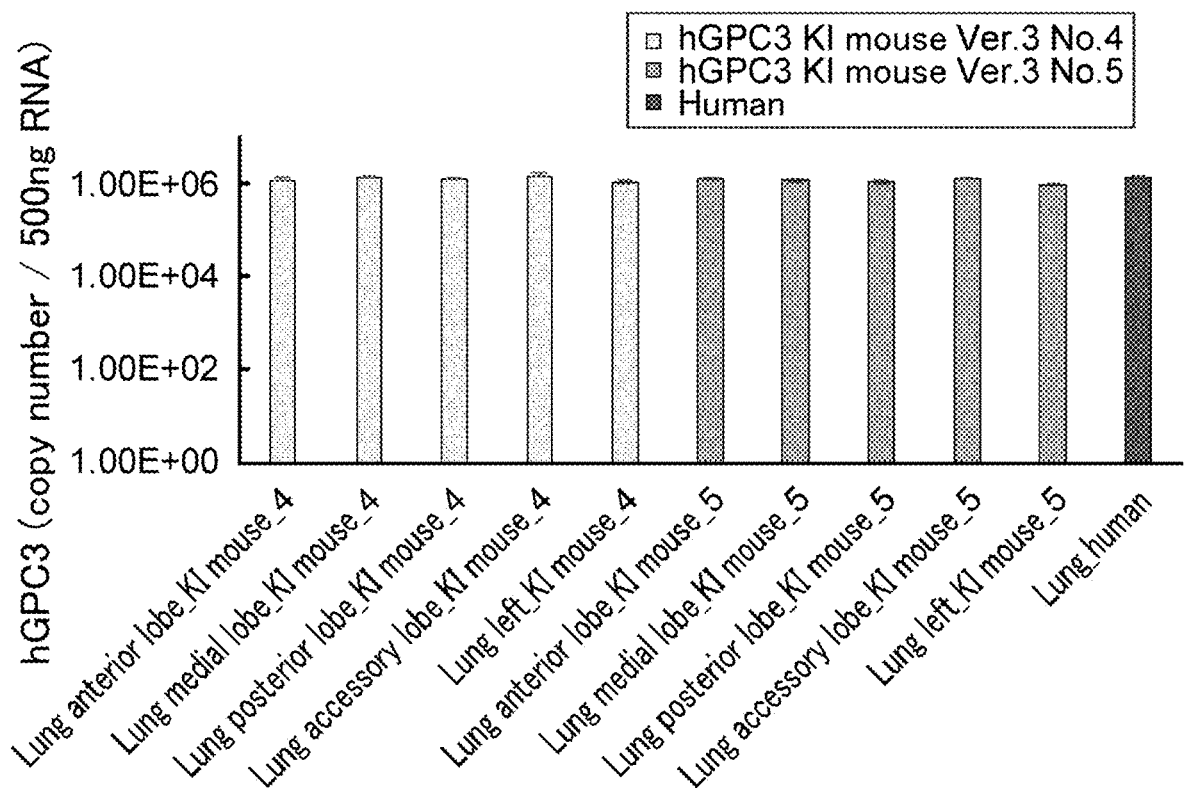
FIG. 9 shows a graph presenting the expression levels of GPC3 mRNA in the lungs of hGPC3 knock-in mice ver. 3 and humans.

When the expression levels of GPC3 mRNA in the lungs of hGPC3KI mice ver. 2 and ver. 3 and cynomolgus monkeys were compared, expression level in ver. 2 was the highest, and the expression levels in ver. 3 and cynomolgus monkeys were nearly equivalent (FIG. 8($a$)). The expression level in hGPC3KI mice ver. 3 was shown to be nearly equivalent to that of the wild-type mouse (FIG. 8($b$)). Furthermore, since the expression level in hGPC3KI mice ver. 3 and the expression level in the cynomolgus monkeys were nearly equivalent, expression levels in the lungs of ver. 3 and humans were compared. The results showed that the expression in ver. 3 was nearly equivalent to that in humans (FIG. 9).

(3) Comparison of Expression Levels

Results of determining the protein expression levels showed that the expression levels are higher in hGPC3KI mice ver. 2 and ver. 3 than in ver. 1. Since hGPC3KI mice ver. 2 and ver. 3 have an exon-intron structure inserted therein, they are designed to undergo splicing out (removal of intron by splicing). Accordingly, this contributes to the stability of mRNA, and may have resulted in the stable synthesis of the hGPC3 protein. Furthermore, compared to the mRNA expression level in hGPC3KI mice ver. 2, the expression level in hGPC3KI mice ver. 3 was shown to be closer to the expression level in humans and in monkeys. On the other hand, the expression level in ver. 2 was higher than that in the wild-type. This showed that the expression level of the transgene can be controlled by appropriately selecting the 3' untranslated region (3'UTR) for use in the transgene, and by using the 3'UTR of the mGpc3 gene, transgene expression level can be adjusted to the expression level in humans or monkeys. As described above, mRNA expression level is controlled by various factors, and it is very difficult to produce mice presenting an expression level of interest by a generally applicable fixed method for producing genetically modified mice. Contrary to this, we overcame the difficulties, and were able to establish hGPC3KI mice ver. 3 which present the expression level of interest.

Since hGPC3KI mice ver. 3 show an expression level closest to the expression level in humans, they were mainly used in the following function analyses.

Example 3: Immune Tolerance to a Human GPC3 Polypeptide (1) Antigen Immunization A soluble human GPC3 protein mixed with an adjuvant (Gerbu adjuvant 10, manufactured by Gerbu GmbH) was administered subcutaneously at 0.1 mg/0.1 mL to hGPC3KI mice ver. 3 and wild-type mice. The day of first administration was defined as day 0, and the administration was carried out on days 14, 21, 28, 35, 42, 49, and 56. The soluble human GPC3 protein was produced according to a method known to those skilled in the art.

(2) Measurement of Antibody Titer

Figure 10:
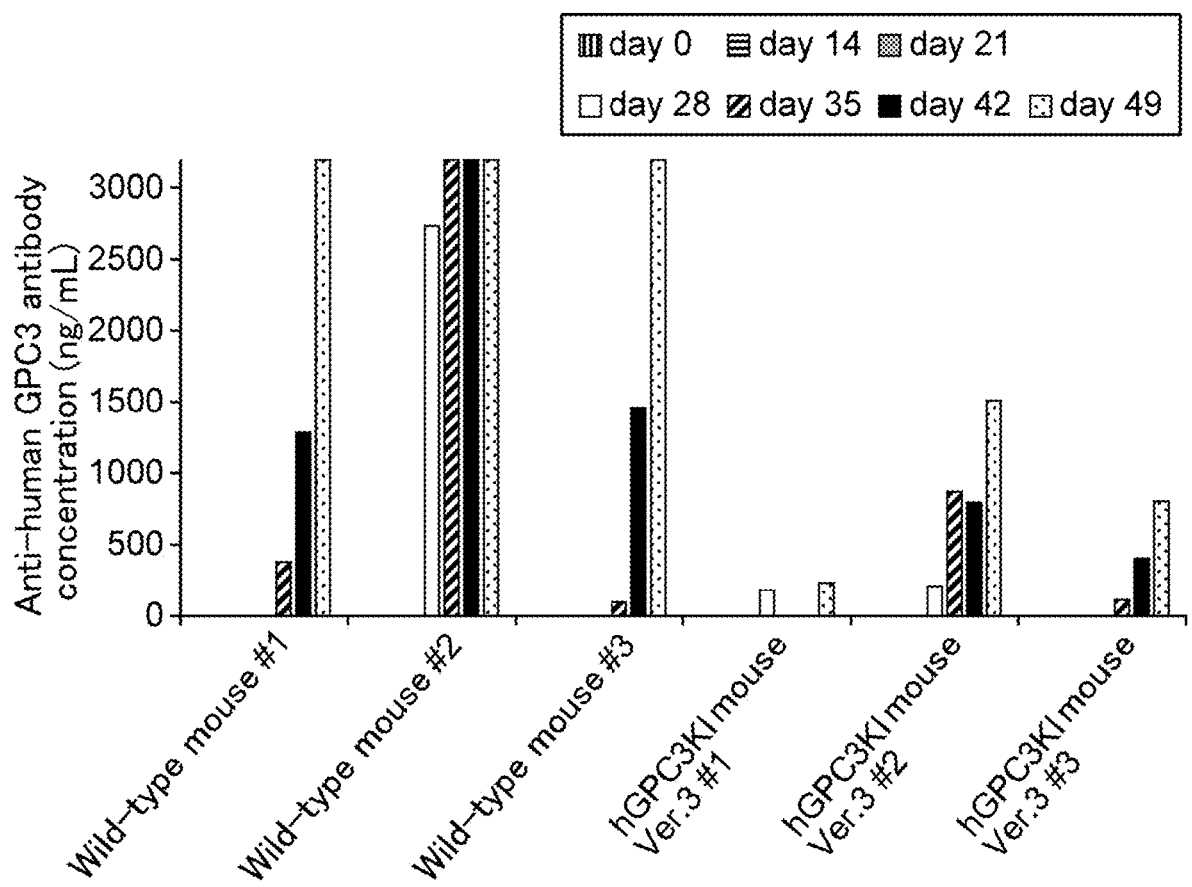
FIG. 10 shows a graph presenting the anti-human GPC3 antibody concentration in blood plasma of wild-type mice and hGPC3 knock-in mice ver. 3 when a human GPC3 protein was administered on days 0, 14, 21, 28, 35, 42, and 49.

The day of first administration was defined as day 0, and blood was collected with heparin treatment before each administration to obtain plasma. Concentration of the anti-human GPC3 antibody in plasma was measured by enzyme linked immunosorbent assay (ELISA) where a soluble human GPC3 (shGPC3) was coated. Coating was carried out using 4 µg/mL shGPC3 solution (pH9.6) on a 96-well plate. Each of the wells was washed with a PBS solution containing 0.05% tween20, and the samples were added. Goat HRP-Anti Mouse IgG (Sigma-Aldrich) was used as a secondary antibody, tetramethylbenzene (TMB) substrate solution (SurModics) was used as a coloring reagent, and the reaction was stopped using 1 N sulfuric acid. Using a UV plate reader, absorbances at 450 nm were measured. As a result, increase in anti-human GPC3 antibody titer was observed to be suppressed in hGPC3KI mice ver. 3 in comparison to the wild-type mice, and immune tolerance to human GPC3 was confirmed (FIG. 10). Since hGPC3 becomes an immunogen for wild-type mice, the transplanted human GPC3-expressing cancer cells may be eliminated by the mice's own immune function. On the other hand, in hGPC3KI mice ver. 3 which has established immune tolerance to human GPC3, human GPC3 does not become an endogenous immunological target; therefore, for attempts to evaluate test samples using cancer-bearing models produced by transplanting human GPC3-expressing cancer cells into mice, the test samples' drug efficacies can be evaluated more accurately.

Example 4: Antitumor Studies of Anti-Human GPC3 Anti-Mouse CD3 Bispecific Antibodies Using hGPC3KI Mice Ver. 3

(1) Cell Line

LLC1 cells (LLC1/hGPC3) forced to express human GPC3 in LLC1 cells (obtainable from ATCC; ATCC number: CRL-1642) were used. LLC1/hGPC3 cells were maintained and passaged in Dulbecco's Modified Eagle's Medium (manufactured by SIGMA) containing 10% FBS (manufactured by BIONET) and 0.5 mg/mL G418 (manufactured by Nacalai Tesque).

(2) Preparation of LLC1/hGPC3 Engrafted Models

LLC1/hGPC3 cells were prepared at 1×10' cells/mL in Dulbecco's Modified Eagle's Medium (manufactured by SIGMA). A 100 µL portion of this cell suspension (1×10$^6$ cells/mouse) was transplanted subcutaneously in the abdominal region of hGPC3KI mice ver. 3. The tumor volume was calculated using the following equation, and when the tumor volume reached 150-200 mm$^3$, the model was determined to be established.

An hGPC3/mCD3 bispecific antibody (hGPC3_mCD3) was produced by combining an anti-human GPC3 (hGPC3) antibody and an anti-mouse CD3 (mCD3) antibody. The heavy chain set forth in SEQ ID NO: 31 and the light chain set forth in SEQ ID NO: 32 were used for the hGPC3 arm. The heavy chain set forth in SEQ ID NO: 33 and the light chain set forth in SEQ ID NO: 34 were used for the mCD3 arm. The hGPC3_mCD3 antibody was prepared at 0.5 mg/mL (5 mg/kg administration group) and 0.1 mg/mL (1 mg/kg administration group) using PBS(-).

(4) Administration of a Pharmaceutical Agent

The LLC1/hGPC3 engrafted models prepared in (2) above were grouped according to the tumor volume, and the antibody samples prepared in (3) above were administered at 10 mL/kg through the tail vein. As a negative control, PBS(-) (Vehicle) was similarly administered at 10 mL/kg through the tail vein.

(5) Evaluation of Antitumor Effects

Figure 11:
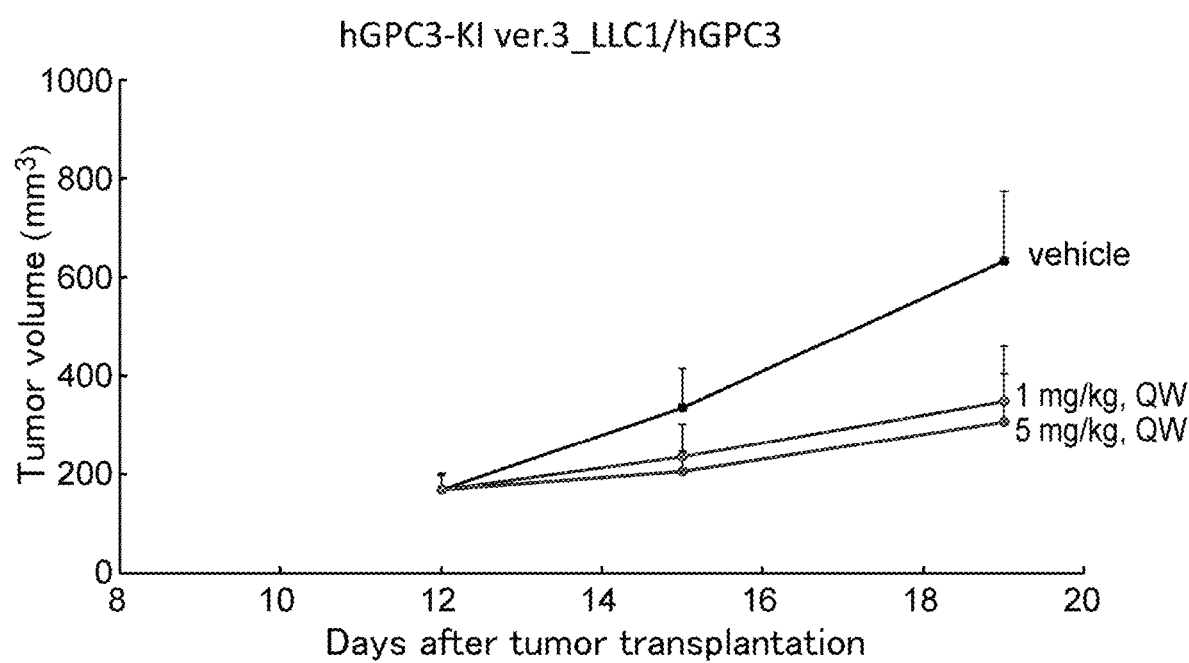
FIG. 11 shows a graph presenting the antitumor effects of the hGPC3_mCD3 antibody in the LLC1/hGPC3-transplanted model using hGPC3 knock-in mice ver. 3.

The antitumor effect of the hGPC3_mCD3 antibody in LLC1/hGPC3 engrafted models was evaluated from the tumor volume at 19 days after transplantation. As a result, tumor growth was found to be significantly inhibited by hGPC3_mCD3 antibody administration. (FIG. 11).

(6) Measurement of Antibody Concentration in Plasma

Approximately 30 µL of blood was collected with heparin treatment from hGPC3KI mice ver. 3 and ver. 1 two hours, one day, and seven days after administration of the above-mentioned antibody. Plasma was separated from the collected blood by centrifugation. Concentration of the hGPC3_mCD3 antibody in plasma was measured by enzyme linked immunosorbent assay (ELISA) where a soluble human GPC3 (shGPC3) was coated. Coating was carried out using 1 µg/mL shGPC3 solution (pH9.6) on a 96-well plate. Each of the wells was washed with a TBS solution containing 0.05% tween20, and the samples were added.

Figure 12:
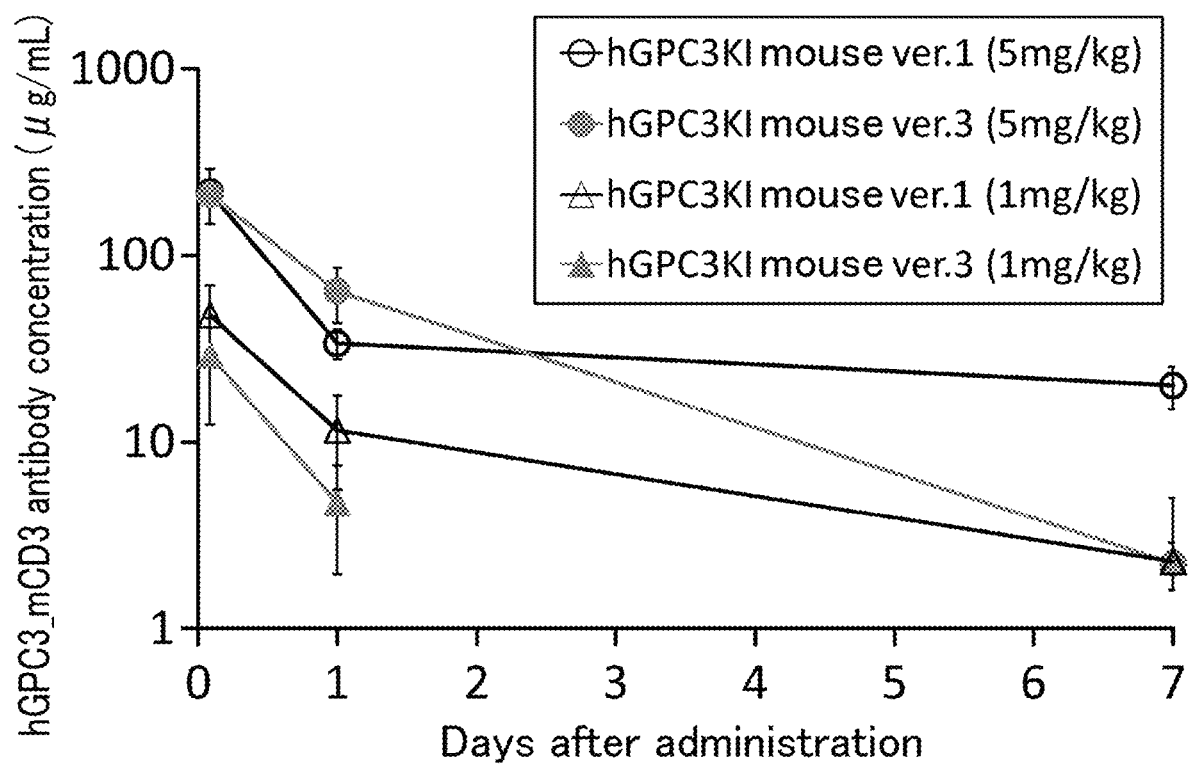
FIG. 12 shows a graph presenting the change in hGPC3_mCD3 antibody concentration in blood plasma of hGPC3 knock-in mice ver. 1 and hGPC3 knock-in mice ver. 3, two hours, one day, and seven days after hGPC3_mCD3 antibody administration.

Anti-Human Kappa Light chain Goat IgG Biotin (Immuno-Biological Laboratories) was added as a secondary antibody, and then Streptavidin-AP conjugate (Roche Diagnostics) was made to react. Using Blue Phos Microwell phosphatase Substrate System (Kirkegaard & Perry Laboratories) as a coloring reagent, absorbances at 650 nm were measured on a UV plate reader. As a result, the hGPC3_mCD3 antibody showed antigen-dependent elimination in hGPC3KI mice. In ver. 3 highly expressing hGPC3, elimination from plasma was confirmed to be faster than in ver. 1 (FIG. 12).

Example 5: Cytokine Release in hGPC3 mCD3 Antibody Administration

Figure 13:
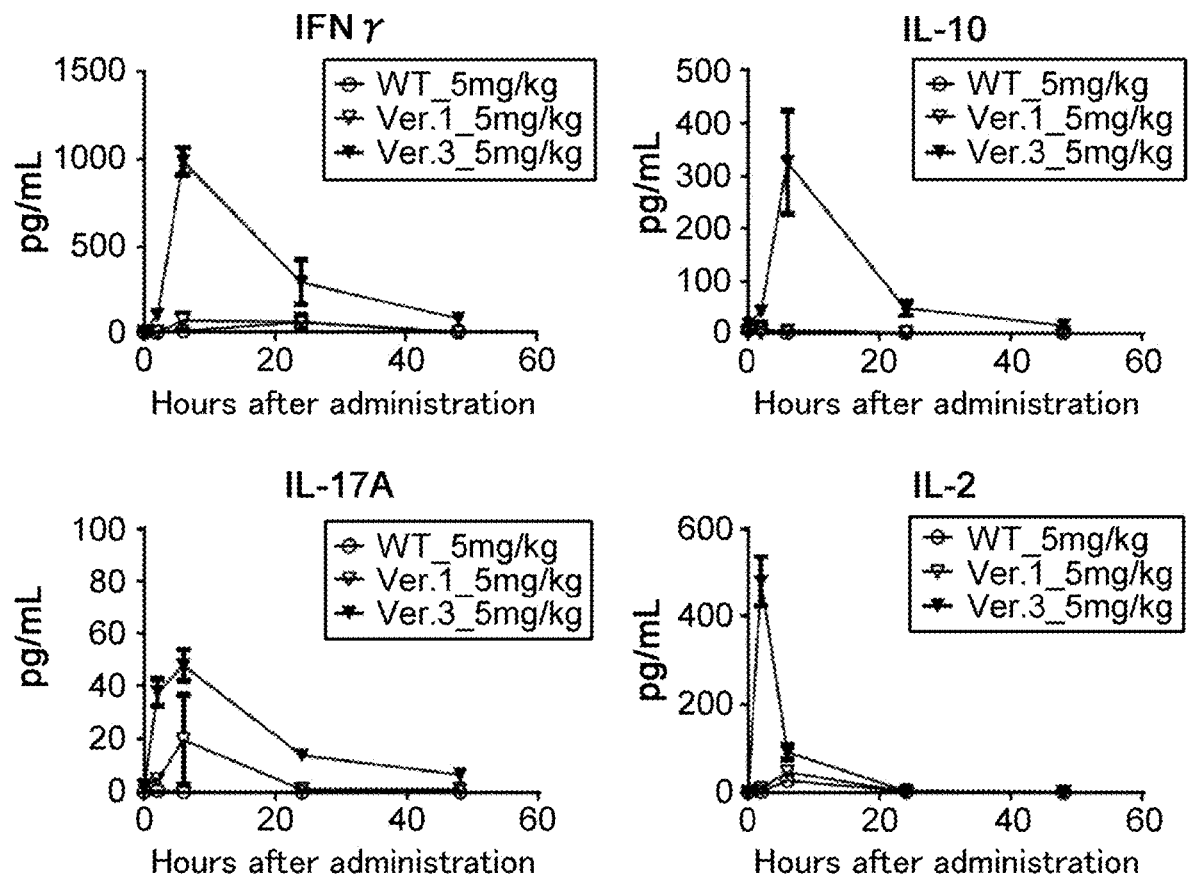
FIG. 13 shows graphs presenting the time course of the change in plasma concentrations of IFN-gamma, IL-10, IL-17, and IL-2 in wild-type mice, hGPC3 knock-in mice ver. 1, and hGPC3 knock-in mice ver. 3 after hGPC3_mCD3 antibody administration.
Figure 14:
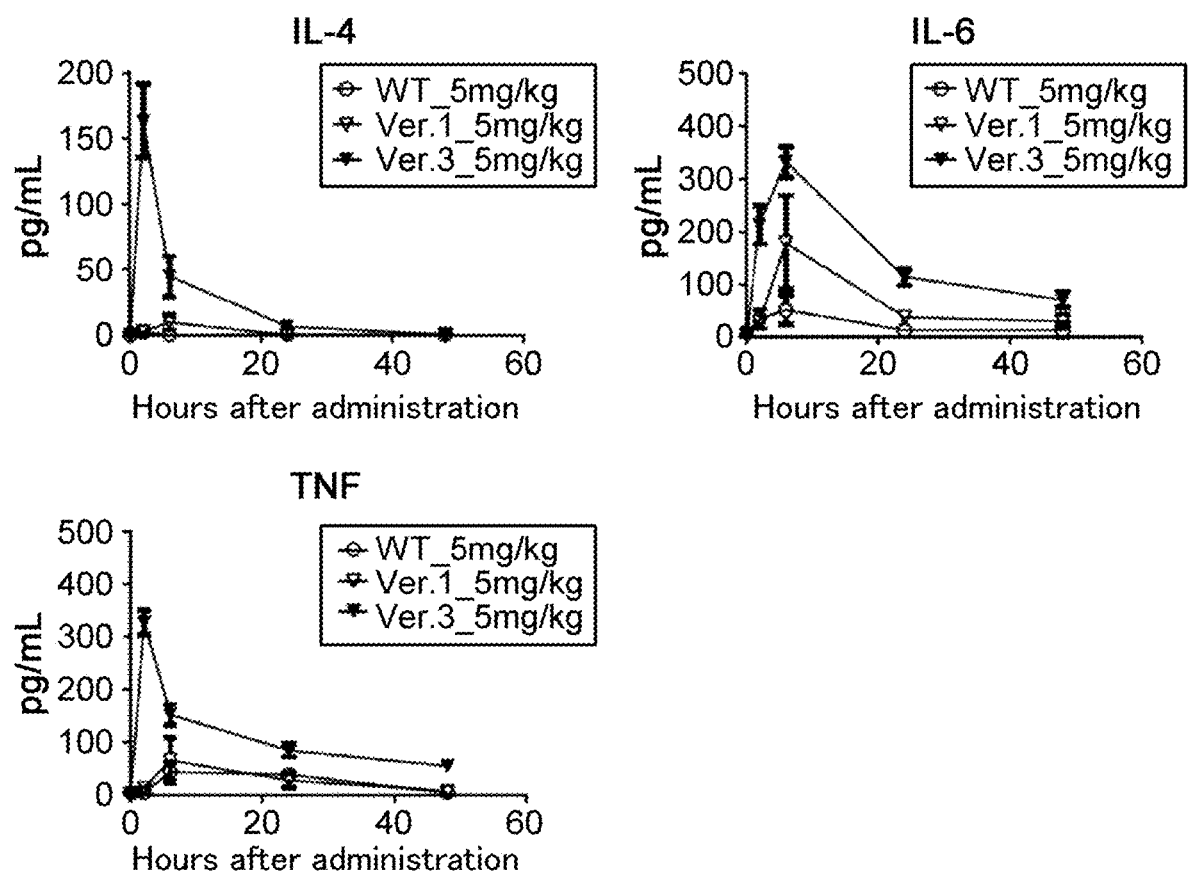
FIG. 14 shows graphs presenting the time course of the change in plasma concentrations of IL-4, IL-6, and TNF in wild-type mice, hGPC3 knock-in mice ver. 1, and hGPC3 knock-in mice ver. 3 after hGPC3_mCD3 antibody administration.

The hGPC3_mCD3 antibody was prepared as in Example 4, and administered to hGPC3KI mice ver. 1, hGPC3KI mice ver. 3, and wild-type mice. Approximately 30 µL of blood was collected with heparin treatment to obtain plasma on the day before antibody administration, and two hours, six hours, 24 hours, and 48 hours after antibody administration. Using the obtained plasma, concentrations of IFN-gamma, IL-10, IL-17A, IL-2, IL-4, IL-6, and TNF were determined using a BDTM cytometric bead array (CBA) mouse Th1/Th2/Th17 cytokine kit (manufactured by BD Bioscience). As a result, hGPC3 antigen-dependent cytokine release was confirmed in hGPC3KI mice ver. 3 and ver. 1, and the level of release was higher in ver. 3 than in ver. 1. On the other hand, since the hGPC3_mCD3 antibody does not bind to mouse GPC3, cytokine release was hardly observed in wild-type mice which do not express hGPC3 (FIGS. 13 and 14). Increase in cytokine is caused by activation of T cells due to binding of the hGPC3_mCD3 antibody to hGPC3 expressed in tissues. Increased cytokine in hGPC3KI mice ver. 3 indicates that the knocked-in hGPC3 gene reflects the original characteristics of GPC3 expression, such as expression on the membrane. Furthermore, when the anti-human GPC3 anti-human CD3 bispecific antibody was administered to monkeys, cytokine increase was observed; therefore, hGPC3KI mice ver. 3 were considered to be mice with which pharmacological action as in humans and monkeys can be seen, and were suggested to be useful for evaluating pharmacological actions in them, and usable in the development of pharmaceutical agents that act specifically to human-derived disease-related molecules.

Example 6: Production of Human CD3 Gene-Substituted Mice (1) Construction of a Mouse Cd3 Gene Region Modification Vector (FIG. 15A)

A bacterial artificial chromosome (BAC) clone was used, into which a genomic region where the mouse CD3ε, CD3δ, and CD3γ genes are positioned had been cloned. A loxP sequence was inserted at the position approximately 3.5 kb 5' upstream of the gene region coding for mouse Cd3ε in this BAC, and the genome region further upstream was removed leaving approximately 3.1 kb. At that time, the loxP sequence was introduced together with neomycin-resistance (neo) gene cassette and insertion was conducted by homologous recombination using a Red/ET system (GeneBridges). In that case, from among the *Escherichia coli* clones that grew in a kanamycin-supplemented medium, clones for which polymerase chain reaction (PCR) method resulted in correct amplification were selected. Next, loxP sequence and Rox sequences were placed at 3' downstream of the Cd3γ gene on the BAC. More specifically, the loxP sequence and Rox sequences were introduced along with hygromycin-resistance (Hyg) gene cassette, and insertion was conducted by homologous recombination using a Red/ET system. In that case, from among the *Escherichia coli* clones that grew in a hygromycin-supplemented medium, clones in which the loxP sequence and Rox sequences were inserted as expected were selected by PCR method. Next, the genomic region 3' downstream of the Hyg gene cassette was removed leaving approximately 3.4 kb.

Figure 15A:
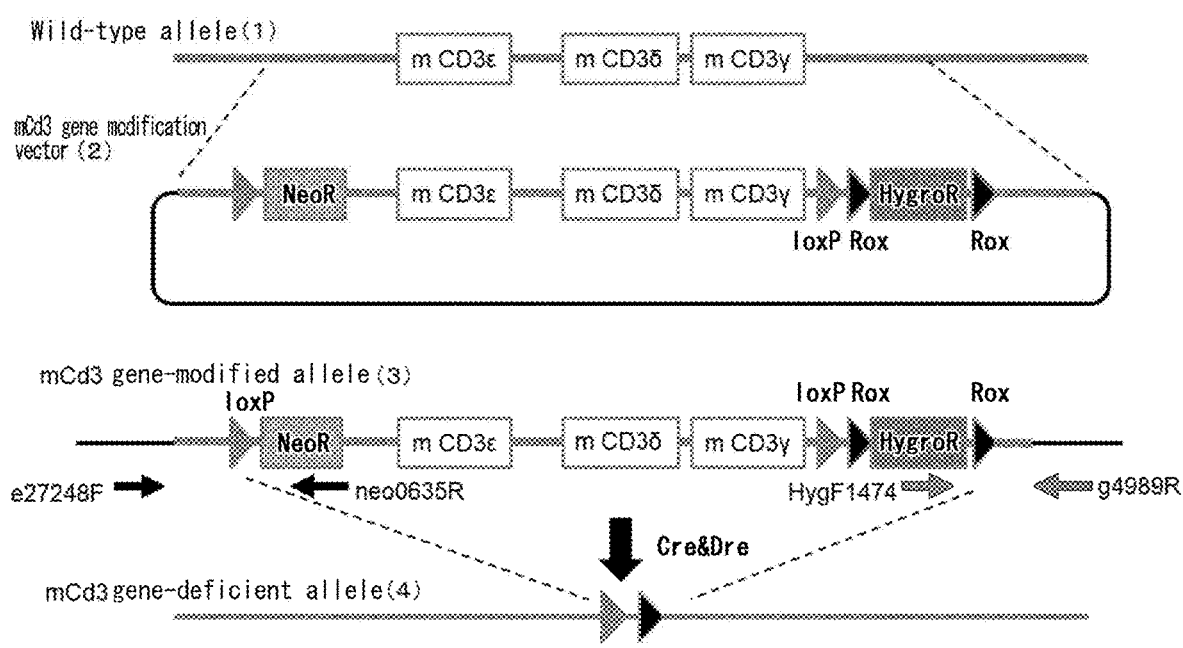
FIG. 15A presents (1) the structure of a genomic DNA containing mouse Cd3ε, Cd3δ, and Cd3γ genes, (2) a mouse Cd3 gene modification vector constructed by modifying a bacterial artificial chromosome (BAC) clone containing the whole gene region, (3) the structure of a genomic DNA in which loxP and Rox sequences have been inserted at the target position using the above-mentioned vector, and (4) the structure of a Cd3ε, Cd3δ, and Cd3γ-gene deficient allele produced by the actions of Cre and Dre recombinases.

(2) Introduction of a Mouse Cd3 Gene Region Modification Vector into Mouse Embryonic Stem Cells (ES Cells) (FIG. 15A)

The above-mentioned mouse Cd3 gene region modification vector was introduced into mouse ES cells (C57BL/6N mouse-derived cells) via electroporation, and after selective culturing with G418, drug-resistant clones were obtained. From these clones, screening for homologous recombinants was performed by a PCR method. For electroporation, 60 μg of the mouse Cd3 gene region modification vector was linearized with NotI or the NotI-untreated circular vector was extracted with phenol/chloroform, precipitated with ethanol, and then dissolved in PBS.

ES cells used in screening were cultured on a 96-well plate and washed twice using 200 μl of PBS solution per well. Then, the cells were treated at 55° C. for two hours after adding a cell lysis buffer having the following composition (5 μl of 10×LA buffer II (TAKARA LA for Taq), 5 μl of 25 mM MgCl$_2$, 5 μl of 5% NP-40, 2 μl of proteinase K (TAKARA, 20 mg/ml), and 33 μl of distilled water), and subsequently treated at 95° C. for 15 minutes to inactivate proteinase K, to thereby serve as PCR samples.

The PCR reaction mixture was made up of 1 μl of the sample, 2.5 μl of 10×LA buffer II, 2.5 μl of 25 mM MgCl$_2$, 4 μl of dNTP (2.5 mM), 0.1 μl each of the primers (50 μM each), 0.25 μl of LA Taq (TAKARA), and 14.55 μl of distilled water (25 μl in total). The PCR conditions included preheating at 94° C. for two minutes, 35 cycles of an amplification cycle of 98° C. for ten seconds and 68° C. for 4 minutes 30 seconds, and additional heating at 68° C. for five minutes.

Figure 16:
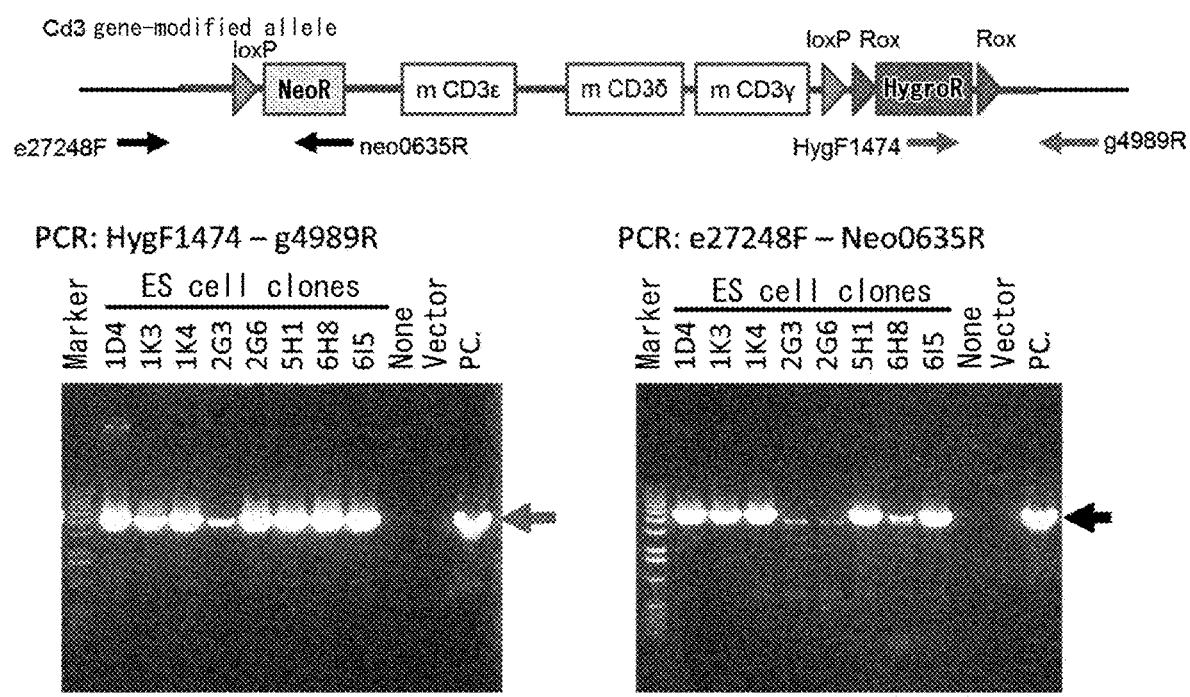
FIG. 16 presents the representative examples of PCR analyses performed for establishing mouse Cd3 gene-modified ES cells.

The following primers were used. The primers were HygF1474 which was positioned within the Hyg gene cassette as a forward primer, and g4989R which was positioned as a reverse primer at the mouse genomic region on the 3' downstream side of the 3' homology arm in the mouse Cd3 gene modification vector (see FIG. 16). In samples of the ES cells in which homologous recombination occurred, an approximately 4-kb band was amplified. HygF1474 (forward) 5'-TATCAGAGCTTGGTTGACGG-3' (SEQ ID NO: 35); and g4989R (reverse) 5'-ACTCGTTGTGGCTTAGAAGCAGTAACAATACC-3' (SEQ ID NO: 36). Furthermore, clones from which amplification signals were obtained using the above-mentioned primer set were subjected to validation using a different primer set. More specifically, e27248F was positioned as a forward primer at the mouse genomic region on the 5' upstream side of the 5' homology arm in the mouse Cd3 gene modification vector, and Neo0635R was positioned as a reverse primer within the Neo gene cassette. In samples of ES cells in which homologous recombination occurred, an approximately 4-kb band was amplified. e27248F (forward) 5'-ACTGTAATCCTAGTA CTTAGGAGGCTGAGG-3' (SEQ ID NO: 37); and Neo0635R (reverse) 5'-AATCCATC TTGTTCAATGGCCGATCC-3' (SEQ ID NO: 38).

Figure 15B:
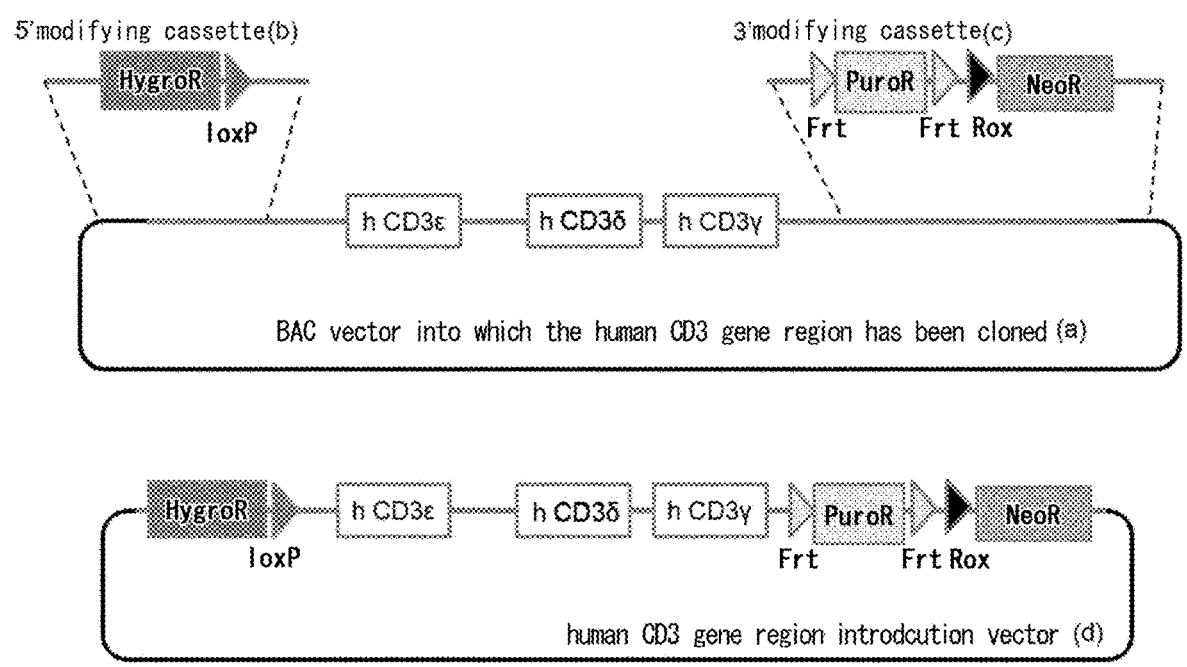
FIG. 15B presents (a) the structures of a BAC clone containing human CD3ε, CD3δ, and CD3γ genes; (b) 5'-modifying cassette and (c) 3'-modifying cassette, both of which are for modifying the BAC clone; and (d) a human CD3 gene region introduction vector constructed through modifications using those above.

(3) Construction of a Human CD3 Gene Region Introduction Vector (FIG. 15B)

A BAC clone was used, into which a genomic region where the human CD3ε, CD3δ, and CD3γ genes are positioned had been cloned. A loxP sequence was inserted at 5' upstream of the gene region coding for human CD3ε in this BAC. At that time, the loxP sequence was introduced along with Hyg gene cassette, and insertion was conducted by homologous recombination using a Red/ET system (GeneBridges). In that case, from among the *Escherichia coli* clones that grew in a hygromycin-supplemented medium, clones for which PCR method resulted in correct amplification were selected. Next, at 3' downstream of the human CD3γ gene in the BAC, puromycin-resistance (Puro) gene flanked on both ends by Frt sequences was introduced together with Neo gene cassette to position a Rox sequence further downstream, and insertion was conducted by homologous recombination using a Red/ET system. In that case, from among the *Escherichia coli* clones that grew in a kanamycin-supplemented medium, clones in which the Frt sequences, the Puro gene, the Rox sequence, and the Neo gene were inserted as expected were selected by PCR method.

(4) Introduction of a Human CD3 Gene Region Introduction Vector and a Recombinase Expression Vector into Cd3 Gene Region-Modified Mouse ES Cells The human CD3 gene region introduction vector, a Cre recombinase expression vector, and a Dre recombinase expression vector were introduced via electroporation into ES cell clones (1D4, 5H1, 615, and 3A5) in which the loxP sequences and Rox sequences were correctly inserted at the targeted sites of the mouse Cd3 gene region in the above-mentioned step; and after selective culturing with puromycin, the grown ES cell clones were genotyped.

First, PCR screening was performed for selection of clones in which recombination between the loxP sequences and between the Rox sequences placed at the mouse Cd3 gene region took place by the action of Cre and Dre, and the genomic region from Cd3ε to Cd3γ was deleted. The ES cells used in screening were cultured on a 96-well plate, washed twice using 200 μl of PBS per well, and treated at 55° C. for two hours after adding a cell lysis buffer having the following composition (5 μl of 10×LA buffer II (TAKARA LA for Taq), 5 μl of 25 mM MgCl$_2$, 5 μl of 5% NP-40, 2 μl of proteinase K (TAKARA, 20 mg/mL), and 33 μl of distilled water), and subsequently treated at 95° C. for 15 minutes to inactivate proteinase K, to thereby serve as PCR samples.

Figure 17A:
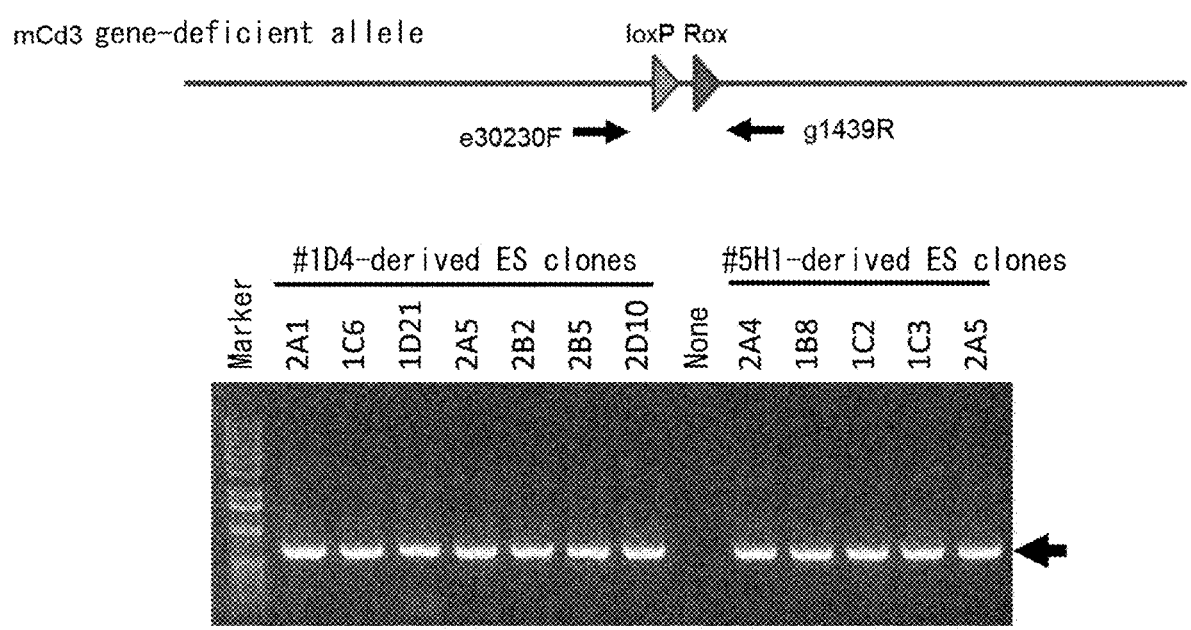
FIG. 17A presents the representative examples of PCR results that detect the deficiency of the mouse Cd3 gene region.

The PCR reaction mixture was made up of 1 µl of the sample, 2.5 µl of 10×LA buffer II, 2.5 µl of 25 mM MgCl$_2$, 4 µl of dNTP (2.5 mM), 0.1 µl each of the primers (50 µM each), 0.25 µl of LA Taq (TAKARA), and 14.55 µl of distilled water (25 µl in total). The PCR conditions included preheating at 94° C. for two minutes, 35 cycles of an amplification cycle of 98° C. for ten seconds and 68° C. for 4 minutes 30 seconds, and additional heating at 68° C. for five minutes. The following primers were used. The primers were e30230F which was positioned as a forward primer at the genomic region on the 5' upstream side of the mouse Cd3ε gene, and g1439R which was positioned as a reverse primer at the genomic region on the 3' downstream side of the mouse Cd3γ gene (see FIG. 17A). In samples of the ES cells in which the Cd3 gene region was deleted, an approximately 0.7-kb band was amplified. e30230F (forward) 5'-TAGCAGCCTTCAGA TGAAGAGGTAGGACTC-3' (SEQ ID NO: 39); and g1439R (reverse) 5'-TTGATGTGC CACCTCACTGCTGCACTGG-3' (SEQ ID NO: 40).

Figure 17B:
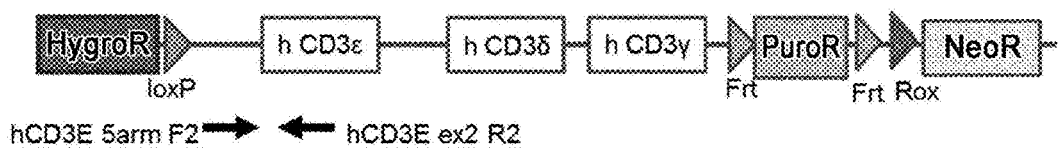
FIG. 17B presents the representative examples of PCR results that detect the introduction of the human CD3 gene region.
Figure 17B:
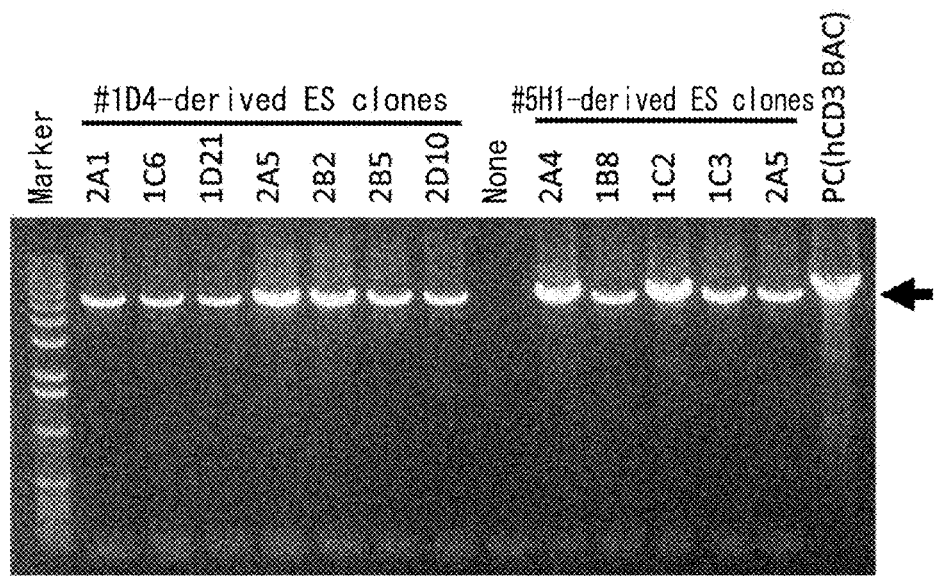
Figure 18:
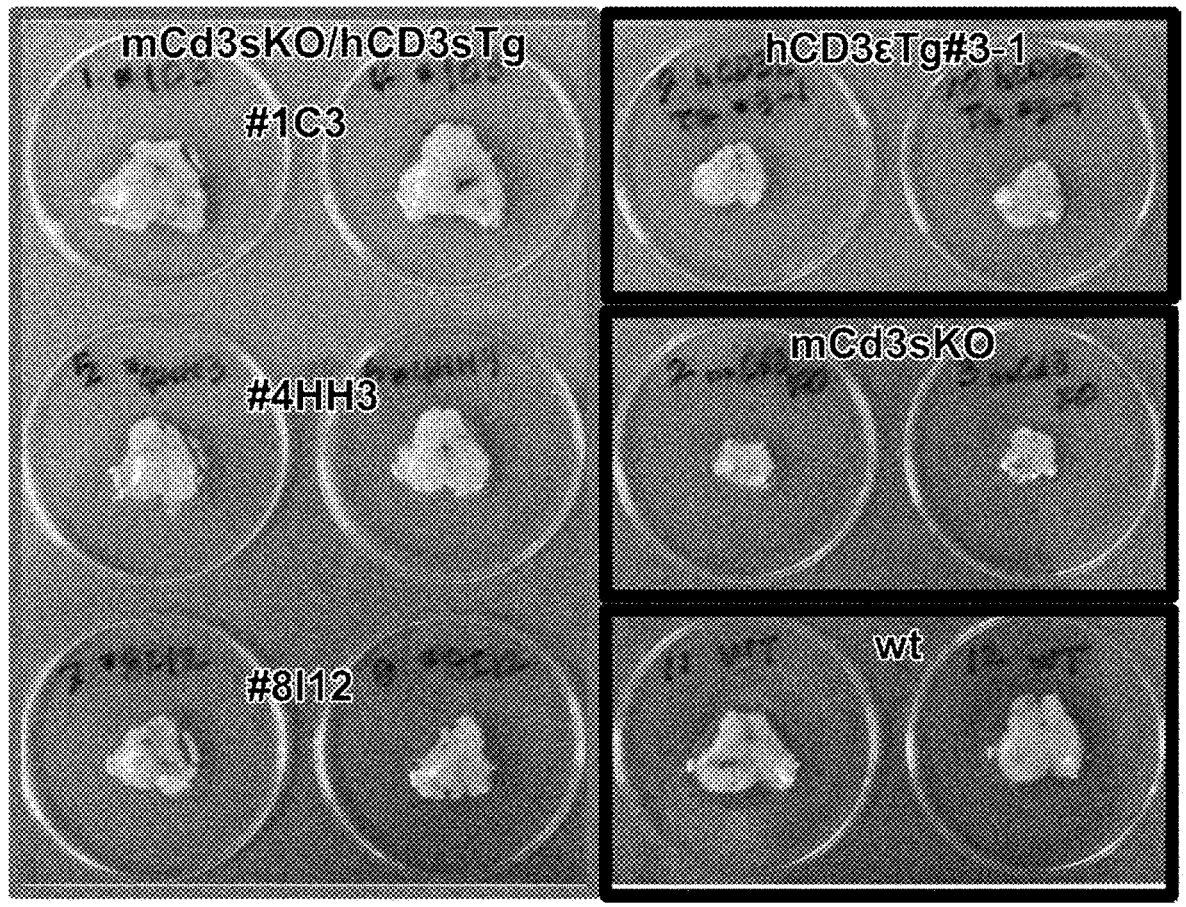
FIG. 18 presents the representative macroscopic photographs of thymuses collected from each of the established lines of human CD3 gene-substituted mice, Cd3 gene-deficient mice, wild type, and human CD3ε gene-introduced mice. Thymuses extirpated from 12 to 13-week-old males are shown for the respective genotypes.

PCR screening was performed for selecting clones in which the human CD3 gene region was introduced from the ES cell clones deficient in the mouse Cd3 gene region. The PCR samples that were used for detecting the deletion of the mouse Cd3 gene region were subjected to the screening. The PCR reaction mixture was made up of 1 µl of the sample, 2.5 µl of 10×LA buffer II, 2.5 µl of 25 mM MgCl$_2$, 4 µl of dNTP (2.5 mM), 0.1 µl each of the primers (50 µM each), 0.25 µl of LA Taq (TAKARA), and 14.55 µl of distilled water (25 µL in total). The PCR conditions included preheating at 94° C. for two minutes, 35 cycles of an amplification cycle of 94° C. for 30 seconds, 58° C. for one minute, and 72° C. for five minutes, and additional heating at 72° C. for five minutes. The following primers were used. The primers were hCD3e_5arm_F2 which was positioned as a forward primer at the genomic region on the 5' upstream side of the human CD3ε gene, and hCD3e_ex2_R2 which was positioned as a reverse primer within the second exon of the human CD3ε gene (see FIG. 17B). In samples of the ES cells in which the human CD3 gene region was introduced, an approximately 5.5-kb band was amplified. hCD3e_5 arm_F2 (forward) 5'-AACTGACAATGGGACATCAGCTGA-3' (SEQ ID NO: 41); and hCD3e_ex2_R2 (reverse) 5'-ATGGGACTGT-TACTTTACTAAGAT-3' (SEQ ID NO: 42).

(5) Production of Mouse Cd3 Gene-Deficient and Human CD3 Gene-Introduced Mice

The homologous recombinant ES clones were suspended by trypsin treatment, and washed with the ES cell medium. Female BALB/c mice which were subjected to superovulation treatment by administering 5 IU of equine chorionic gonadotropin (eCG) and human chorionic gonadotropin (hCG) intraperitoneally at 48-hour intervals were crossed with male mice of the same strain. The day when a plug was confirmed in a female mouse was regarded as day 0.5. On gestation day 3.5, blastocyst-stage embryos collected by perfusing the uterus were used as host embryos, in which 10 to 15 of the ES cells were injected. The embryos after the injection were transferred into the uterus of ICR recipient females on Day 2.5 pseudopregnancy, and their offspring were obtained 17 days later. Screening based on the coat color of the offspring obtained by injection of the ES cells to the blastocysts, yielded chimeric mice having a mixture of the recombinant ES cells (black) and the host blastocyst-derived cells (albino). After sexual maturation, the male chimeric mice were crossed with C57BL/6N-female mice, and transmission of the knock-in allele to the next generation was confirmed by a PCR method using the genomic DNA extracted from the tissues of the second-generation mice as the template. PCR was performed by the above-mentioned method used for screening of the ES cells. As a result, individuals from which the human CD3 gene region-specific 5.5-kb signal and the mouse Cd3 gene region deficiency-specific 0.7-kb signal were detected were obtained, and the human CD3 gene region allele and the mouse Cd3 gene region-deficient allele were confirmed to be transmitted to these individuals. Furthermore, breeding of mice having the above-described genotype yielded mouse individuals whose mouse Cd3 gene region is homozygously deleted and which have the human CD3 gene region, that is, human CD3 gene region-substituted mice were obtained. Transgenic mice in which human CD3ε alone had been introduced (hereinafter, hCD3εTg mice) were produced according to the report by Wang et al. (Wang et al. (1994) PNAS. 91:9402-9406), and they were examined as comparisons in the later experiments.

(6) Thymus Weights and Spleen Weights of Human CD3 Gene-Substituted Mice

Figure 4:
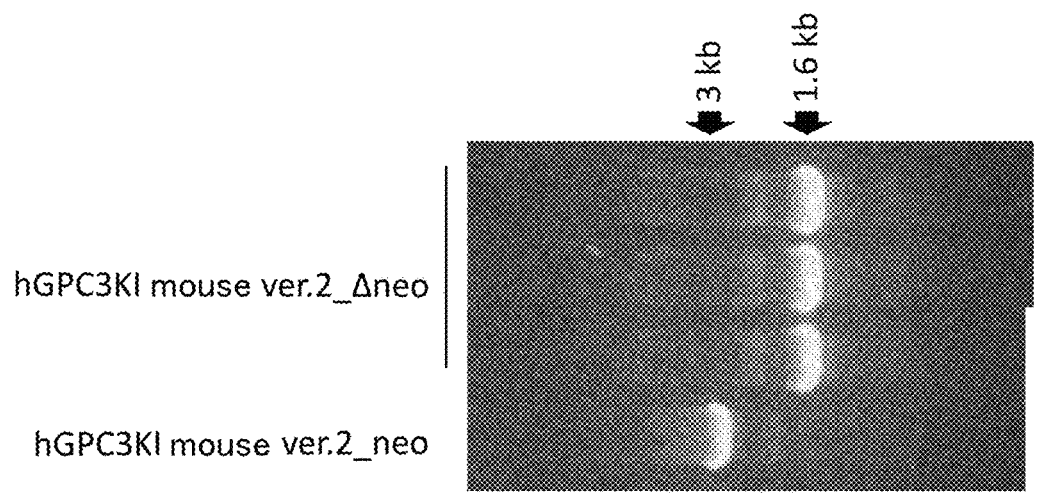
FIG. 4 presents the representative examples of PCR performed to detect neo gene cassette removal in hGPC3 knock-in mice ver. 1 and hGPC3 knock-in mice ver. 2 [hGPC3 knock-in mice ver. 1 (a) and hGPC3 knock-in mice ver. 2 (b)]
Figure 4:
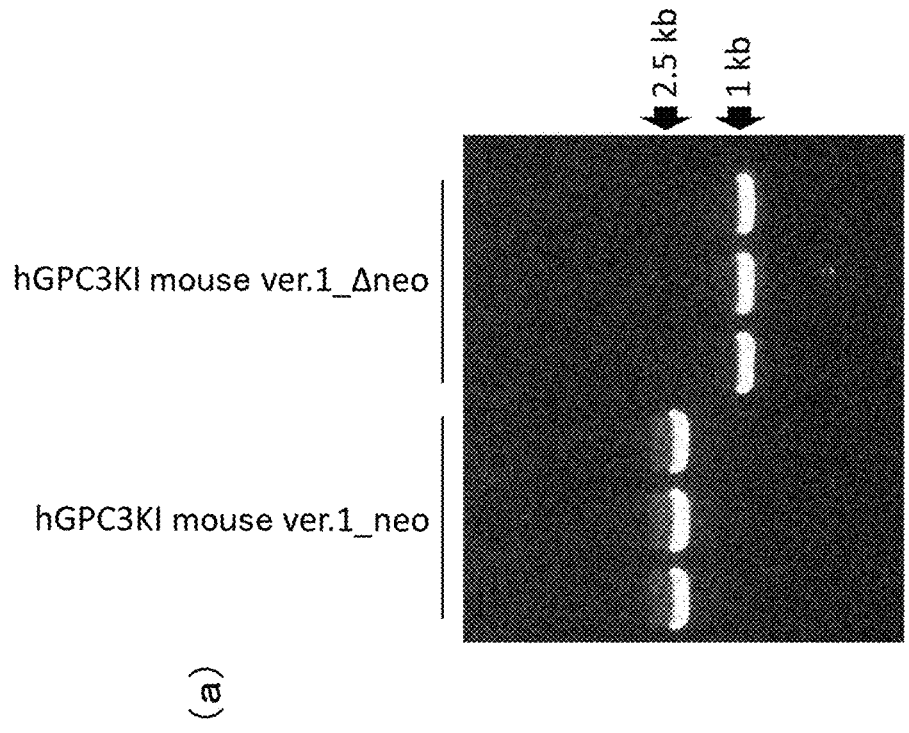
Figure 19:
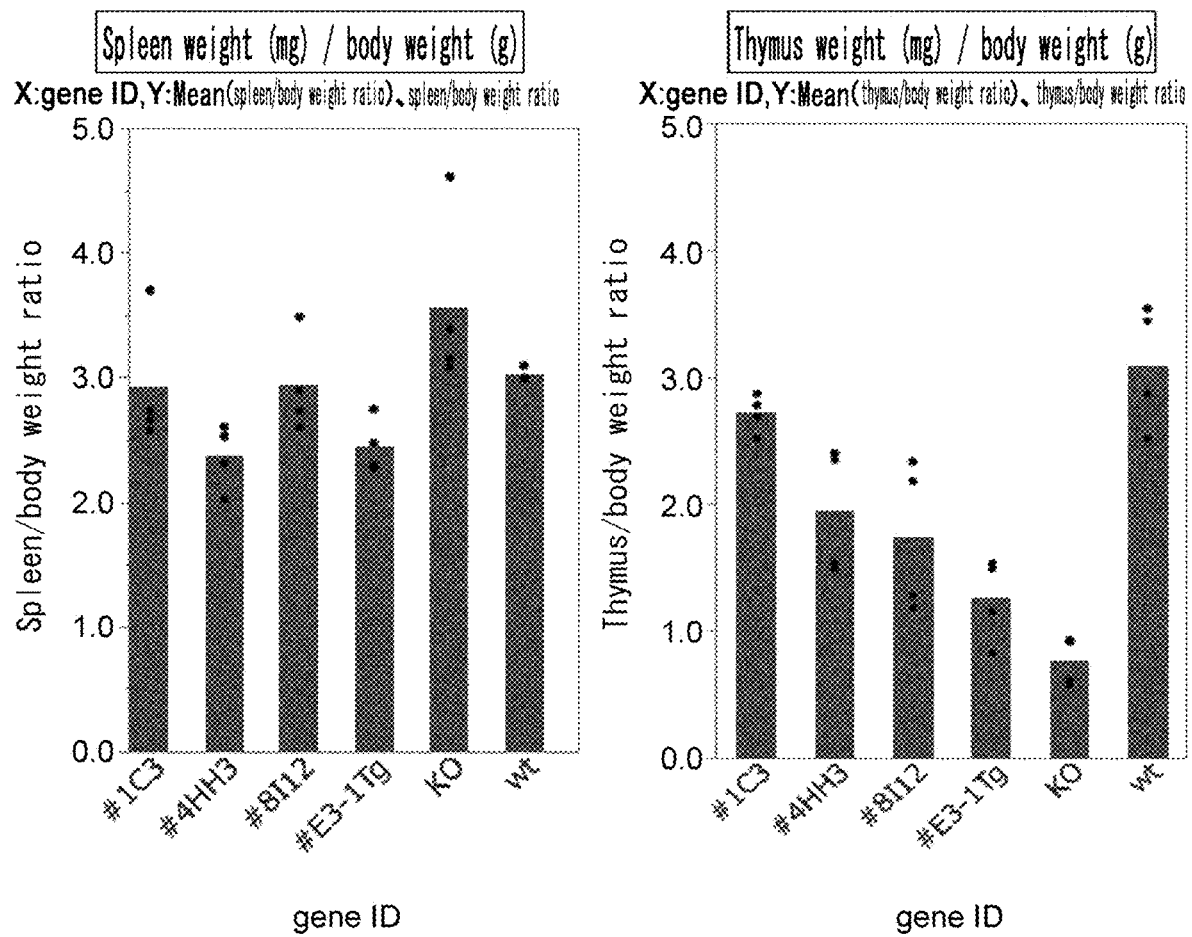
FIG. 19 presents the results of measuring the tissue weights of the spleens and thymuses collected from each of the established lines of human CD3 gene-substituted mice, Cd3 gene-deficient mice, wild-type, and human CD3ε gene-introduced mice. Ratios of tissue weight per body weight were calculated, and the value obtained for each individual is plotted by a black dot and the mean values are shown by columns.

Spleen and thymus were collected from mice (12 to 14-week old, male) and the tissue weights were measured. As shown in FIG. 4, the thymus of the human CD3-substituted mice did not show gross abnormalities. Tissue weight per body weight was calculated for analysis. The body weights and tissue weights (spleen and thymus) were measured for four male mice in each group, and represented as graphs. The tissue weight per body weight ratios were calculated, the values obtained for each individual are plotted by a black dot, and the mean value is shown by a column (FIG. 19). Regarding spleen weight, increasing trend was observed in the Cd3 gene-deficient mice as compared to mice of other genotypes, but no remarkable differences were observed. On the other hand, regarding thymus weight, the Cd3 gene-deficient mice showed decrease down to one third or so as compared to that of the wild-type. In the human CD3 gene-substituted mice produced by introducing a human CD3 gene into the Cd3 gene-deficient mice, recovery of thymus weight was observed, and particularly in the individuals of line no. 1C3, thymus weight was recovered even to the level equivalent to that of the wild-type mice. As reported by Wang et al., thymic atrophy was observed in hCD3εTg mice (Wang et al. (1994) PNAS. 91:9402-9406).

(7) Confirmation of Expressions of Human CD3 and Mouse Cd3 in the Respective Lines of Human CD3 Gene-Substituted Mice —Confirmation by RT-PCR Method Using Hemocyte RNA—

Expressions of human CD3δ, human CD3δ, human CD3γ, mouse Cd3δ, mouse Cd3δ, and mouse Cd3γ were analyzed by RT-PCR using hemocyte RNA. Using a Catrimox-14 RNA Isolation Kit (TaKaRa Bio), total RNA was prepared from blood collected from the dorsal metatarsal vein or the abdominal vena cava. A 1 µg portion each of the total RNAs was used as a template to synthesize cDNAs by performing reverse transcription reactions with a Super-Script III First Strand cDNA Synthesis Kit (Invitrogen) using Oligo dT (20) primers. Human CD3δ, human CD3δ, human CD3γ, mouse Cd3δ, mouse Cd3δ, and mouse Cd3γ were detected by performing PCR using the synthesized cDNAs as templates. Primers for the protein coding regions were designed to detect the expression of all of the genes. Human CD3ε was detected using the combination of forward primer E0333F (5'-AAGAAATGGGTGGTATTA-CACAGACACC-3' (SEQ ID NO: 43)) and reverse primer E0912R (5'-TGGGCCAGCGGGAGGCAGTGTTCTCC AGAGG-3' (SEQ ID NO: 44)). Human CD3δ was detected using the combination of forward primer D0092F (5'-

TAGTTCGGTGACCTGGCTTTATCTACTGG-3' (SEQ ID NO: 45)) and reverse primer D0685R (5'-ATGGCTGCTTCTAGAAGCCACCAGTCT CAGG-3' (SEQ ID NO: 46)). Human CD3γ was detected using the combination of forward primer G0048F (5'-TGCTC-CACGCTTTTGCCGGAGGACAG-3' (SEQ ID NO: 47)) and reverse primer G0666R (5'-TAGGAG-GAGAACACCTGGACTACTC-3' (SEQ ID NO: 48)). On the other hand, mouse Cd3ε was detected using the combination of forward primer e0065F (5'-AGCATTCTGAGAG-GATGCGGTGGAACAC-3' (SEQ ID NO: 49)) and reverse primer e0699R (5'-TGCTCGGAGGGCTG-GATCTGGGTCC ACAG-3' (SEQ ID NO:50)). Mouse Cd3δ was detected using the combination of forward primer d055F (5'-TCATCCTGTGGCTTGCCTCTATTTGTTGC-3' (SEQ ID NO: 51)) and reverse primer d651R (5'-TTGC-TATGGCACTTTGAGAAACCTCCATC-3' (SEQ ID NO: 52)). Mouse Cd3γ was detected using the combination of forward primer g080F (5'-AATACTT CTACTG-GAGAAGCAAAGAG-3' (SEQ ID NO: 53)) and reverse primer g316R (5'-TAGTTGCATTTAGAGGACTTAT-TATGC-3' (SEQ ID NO: 54)).

The composition of the PCR reaction solution (25 μl in total) was made up of 1 μl of the sample, 2.5 μl of 10×Ex buffer, 2 μl of dNTP (2.5 mM), 0.1 μl each of the primers (50 μM each), 0.25 μl of Ex Taq (TAKARA), and 19.05 μl of distilled water. The PCR conditions for human CD3δ, human CD3γ, mouse Cd3δ, and mouse Cd3γ included preheating at 94° C. for two minutes, 35 cycles of an amplification cycle of 94° C. for 30 seconds, 60° C. for 30 seconds, and 72° C. for two minutes, and additional heating at 72° C. for five minutes. For human CD3ε and mouse Cd3ε, the PCR conditions included preheating at 94° C. for two minutes, 40 cycles of an amplification cycle of 94° C. for 30 seconds, 60° C. for 30 seconds, and 72° C. for two minutes, and additional heating at 72° C. for five minutes. PCR primers were designed so that the detected amplification products of human CD3γ, human CD3δ, and human CD3γ will be 580 bp, 594 bp, and 620 bp, respectively, and those of mouse Cd3γ, mouse Cd3δ, and mouse Cd3γ will be 635 bp, 597 bp, and 237 bp, respectively.

Figure 20:
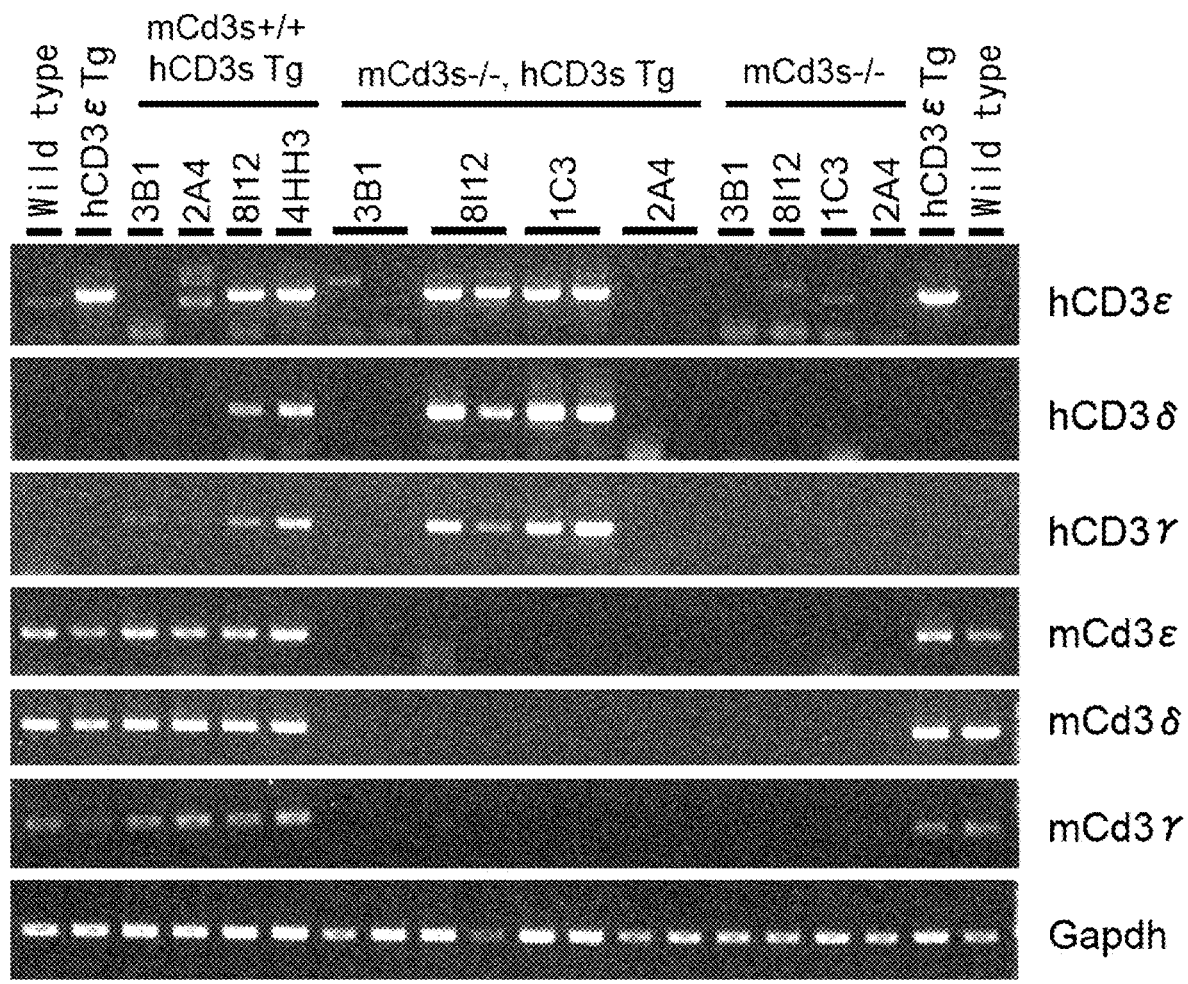
FIG. 20 presents the results of examining by RT-PCR the expressions of each of the human CD3 molecules and each of the mouse Cd3 genes in each of the established lines of human CD3 gene-substituted mice, Cd3 gene-deficient mice, wild-type mice, and human CD3ε gene-introduced (hCD3ε Tg) mice. Among the established lines of the human CD3 gene-substituted mice, signals specific to hCD3ε, hCD3δ, and hCD3γ were detected in line numbers 1C3 and 8I12. The signals were not detected in line numbers 3B1 and 2A4.

In the Cd3 gene-deficient mice, the respective mouse Cd3 molecule-derived PCR signals were not detected. Only human CD3γ, human CD3δ, and human CD3γ were detected, and none of mouse Cd3ε, mouse Cd3δ, and mouse Cd3γ was detected from the samples derived from lines 1C3 and 8I12 of the above-mentioned lines among the human CD3 gene-substituted mouse lines (line nos. 1C3, 3B1, 8I12, and 2A4) produced by introducing the human CD3 gene region to the Cd3 gene-deficient mice (FIG. 20). From the samples derived from wild-type mice, human CD3ε, human CD3δ, and human CD3γ were not detected, and mouse Cd3ε, mouse Cd3δ, and mouse Cd3γ were detected (FIG. 20). These results confirmed that mice expressing human CD3ε, CD3δ, and CD3γ instead of mouse Cd3ε, Cd3δ, and Cd3γ were obtained as designed. Line 4HH3 in FIG. 6 was analyzed in an individual in which the mouse Cd3 allele is a wild-type and the human CD3 gene has been introduced, and the respective human CD3 molecules and the respective mouse Cd3 molecules are both detected. Subsequently, it was cross-bred with Cd3-deficient mice to establish a mouse Cd3 allele-deficient and human CD3 gene-expressing line.

—Analysis by Immunohistological Staining—

Figure 21:
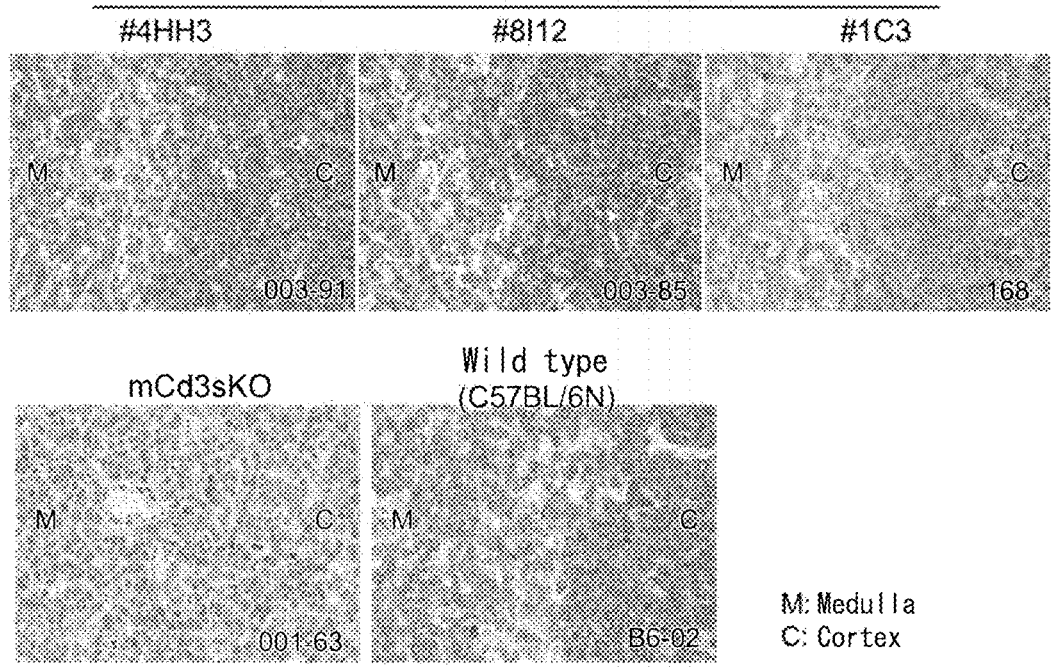
FIG. 21 presents the representative examples of immunohistological staining for CD3 performed on the thymus (A) and spleen (B) of each established line of human CD3 gene-substituted mice (1C3, 8I12, and 4HH3). In both tissues, staining was observed only in the T cell zone as in the wild-type mouse. Furthermore, staining was not observed in the Cd3 gene-deficient mice, and this showed that the staining in the human CD3 gene-substituted mice was due to the expression of the introduced human CD3 genes.
Figure 21:
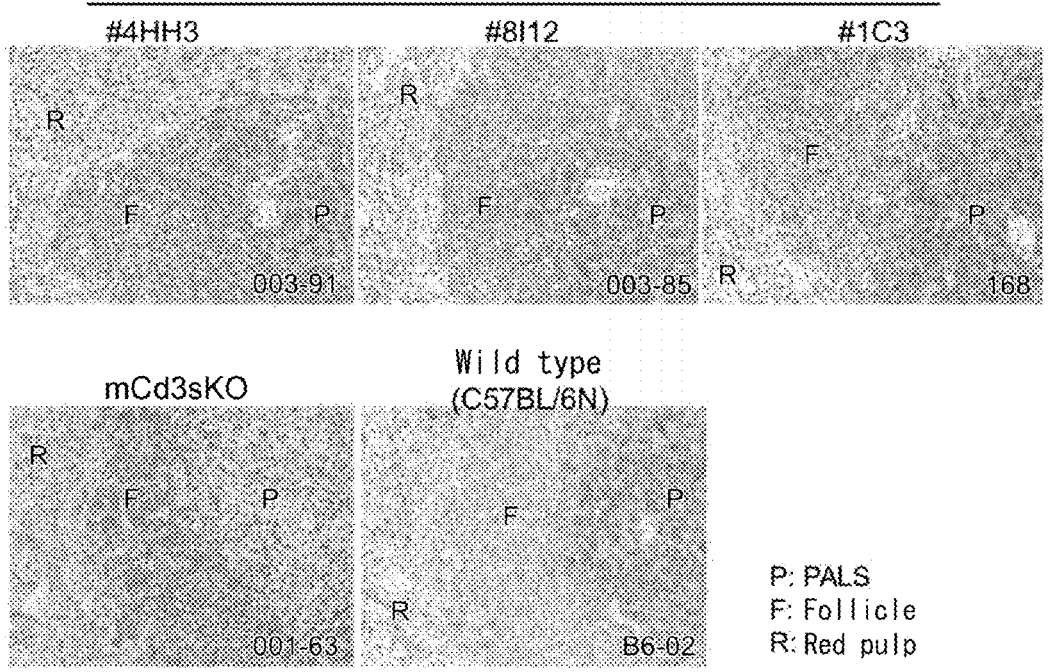
Figure 22:
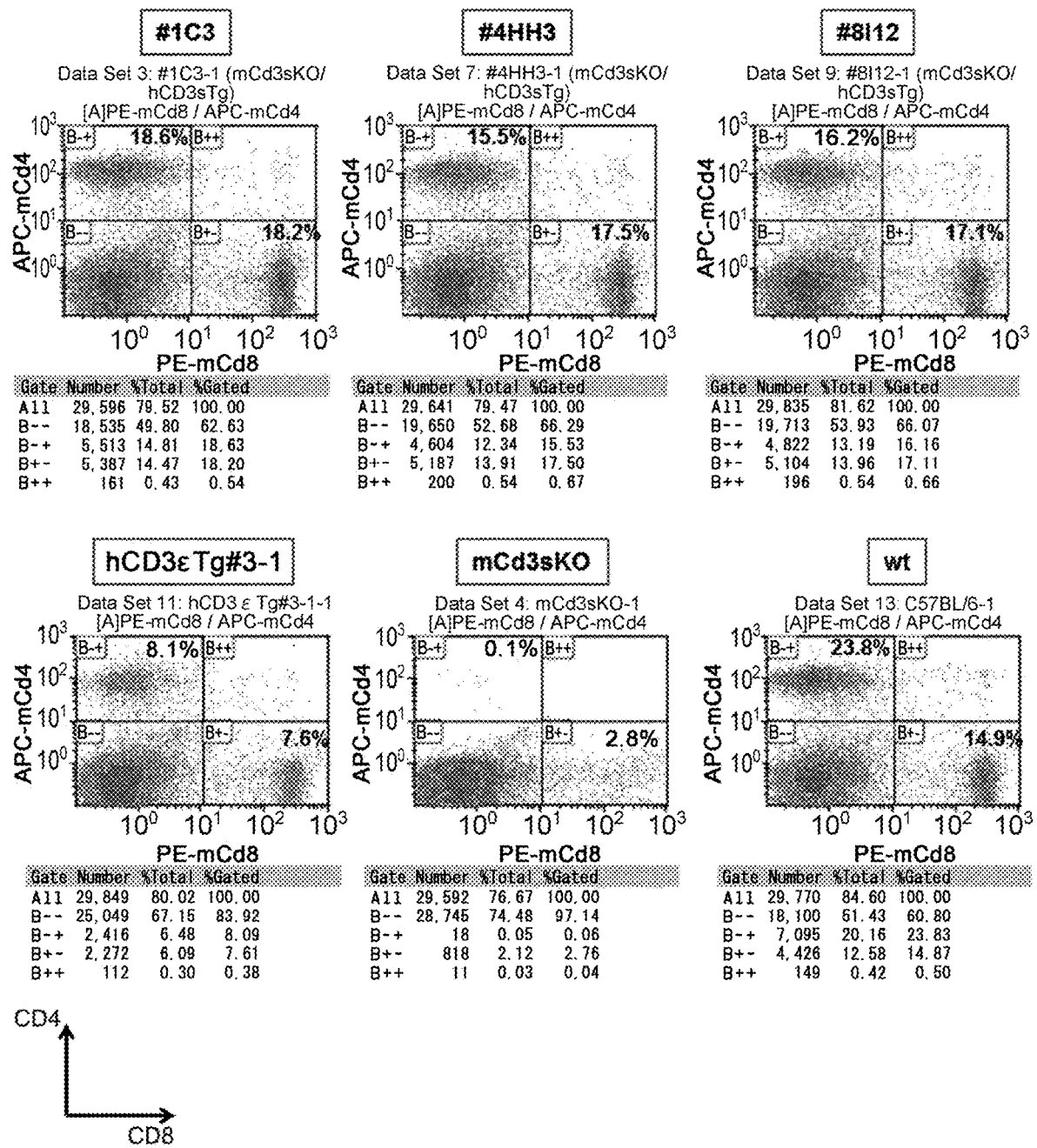
FIG. 22 presents the representative results of analyzing by FACS the abundance ratio of mature T cells in the thymus of each established line of human CD3-substituted mice.

The tissue distribution was examined using the anti-CD3 antibody as the primary antibody. CD3 staining was not observed in any of the tissues from the Cd3-deficient mice, while CD3-specific staining equivalent to that of wild-type mice was observed for the human CD3-substituted mice produced by introducing the human CD3 genes to the Cd3-deficient mice. More specifically, specific staining was observed in the T cell zones in the thymus (FIG. 21A) and spleen (FIG. 21B). In all tissues, staining was observed only in the T cell zone, similarly to the wild-type mice. Furthermore, staining was not observed in the Cd3 gene-deficient mice, indicating that staining in the human CD3 gene-substituted mice was due to the expression of the introduced human CD3 genes. Furthermore, the detection of CD3ε in the major organs was the same as in the wild-type, and ectopic staining was not observed (Table 1).

TABLE 1 hCD3. mCD3KCTG mouse
IACUC 14-074

| | mCD3ko, hCD3TG Line | | | | | | | | |
|---|---|---|---|---|---|---|---|---|---|
| | #4HH3 | | | #BI12 | | | #1C3 | | |
| | Animal No. | | | | | | | | |
| | 008-130 | 010-163 | 003-91 | 003-85 | 003-86 | 001-60 | 168 | 169 | 97 |
| | Gender | | | | | | | | |
| Organs | ♀ | ♀ | ♂ | ♂ | ♂ | ♂ | ♀ | ♀ | ♂ |
| Findings | Date of IHC Staining: A, 2014 Jun. 19; B, 2014 Jun. 25 | | | | | | | | |
| IHC Staining: CD3 | A | A | A | A | A | A | A | A | A |
| Thymus | | | | | | | | | |
| Atrophy | + | ± | − | − | ± | − | − | − | − |
| Lymphocyte, cortex | ++ | +++ | +++ | +++ | +++ | +++ | +++ | +++ | +++ |
| Lymphocyte, medulla | +++ | +++ | +++ | +++ | +++ | +++ | +++ | +++ | +++ |
| Other tissues | − | − | − | − | − | − | − | − | − |
| Mesentery | | | | | | | | | |
| Atrophy | + | + | ± | − | ± | + | − | + | + |
| Lymphocyte, paracortex | ++ | ++ | ++ | +++ | +++ | ++ | +++ | ++ | ++ |
| Lymphocyte, follicle | + | + | + | + | + | + | + | + | + |
| Lymphocyte, medulla | + | + | + | + | + | + | + | + | + |
| Other tissues | − | − | − | − | − | − | − | − | − |
| Ileum | | | | | | | | | |

TABLE 1-continued hCD3. mCD3KCTG mouse
IACUC 14-074

| | | | | | | | | | |
|---|---|---|---|---|---|---|---|---|---|
| Atrophy of GALT | + | − | − | − | − | − | − | − | − |
| Lymphocyte, GALT | + | ± | ± | ± | ++ | + | + | ++ | + |
| Lymphocyte, lamina propria | ± | + | + | ± | + | + | + | + | + |
| Other tissues | − | − | − | − | − | − | − | − | − |
| Spleen | | | | | | | | | |
| Atrophy | ± | − | − | − | − | ± | − | − | − |
| Lymphocyte, PALS | +++ | +++ | +++ | +++ | +++ | +++ | +++ | +++ | +++ |
| Lymphocyte, follicle | + | + | + | + | + | + | + | + | + |
| Lymphocyte, red pulp | ++ | ++ | ++ | ++ | ++ | ++ | ++ | ++ | ++ |
| Other tissues | − | − | − | − | − | − | − | − | − |
| Liver | | | | | | | | | |
| Lymphocyte, sinusoid | + | + | + | + | + | + | + | + | + |
| Other tissues | − | − | − | − | − | − | − | − | − |
| Kidney | | | | | | | | | |
| Lymphocyte, interstitium | ± | − | ± | ± | ± | ± | ± | ± | ± |
| Other tissues | − | − | − | − | − | − | − | − | − |
| Adrenal gland | | | | | | | | | |
| Lymphocyte, interstitium | − | − | − | − | − | ± | ± | − | ± |
| Other tissues | − | − | − | − | − | − | − | − | − |
| Lung | | | | | | | | | |
| Lymphocyte, alveolar wall | ± | − | ± | ± | ± | ± | ± | ± | ± |
| Other tissues | − | − | − | − | − | − | − | − | − |
| Heart | | | | | | | | | |
| Lymphocyte, interstitium | − | − | ± | − | − | − | ± | ± | ± |
| Other tissues | − | − | − | − | − | − | − | − | − |
| Gastrocnemius muscle | − | − | − | − | − | − | − | − | − |

| | hCD3 ε TG | | mCD3KO | | | C57BL/6N | | |
|---|---|---|---|---|---|---|---|---|
| | Line | | | | | | | |
| | #3-1-78 | #195 | None | | | None | | |
| | Animal No. | | | | | | | |
| | 195 | 790 | 001-63 | 001-64 | 001-67 | B6-01 | B6-02 | B6-03 |
| | Gender | | | | | | | |
| Organs | Positive control | | ♀ | ♀ | ♂ | ♀ | ♀ | ♂ |
| Findings | Date of IHC Staining: A, 2014 Jun. 19; B, 2014 Jun. 25 | | | | | | | |
| IHC Staining: CD3 | A | A | A | A | A | B | B | B |
| Thymus | | | | | | | | |
| Atrophy | + | − | ++ | ++ | ++ | − | − | − |
| Lymphocyte, cortex | +++ | +++ | − | − | − | +++ | +++ | +++ |
| Lymphocyte, medulla | +++ | +++ | − | − | − | +++ | +++ | +++ |
| Other tissues | − | − | − | − | − | − | − | − |
| Mesentery | NA | NA | | | | | | |
| Atrophy | | | ++ | ++ | ++ | − | − | − |
| Lymphocyte, paracortex | | | − | − | − | +++ | +++ | +++ |
| Lymphocyte, follicle | | | − | − | − | + | + | + |
| Lymphocyte, medulla | | | − | − | − | + | + | + |
| Other tissues | | | − | − | − | − | − | − |
| Ileum | NA | NA | | | | | | |
| Atrophy of GALT | | | ++ | ++ | ++ | − | − | − |
| Lymphocyte, GALT | | | − | − | − | ++ | + | + |
| Lymphocyte, lamina propria | | | − | − | − | + | + | ± |
| Other tissues | | | − | − | − | − | − | − |
| Spleen | | | | | | | | |
| Atrophy | − | − | + | + | + | − | − | − |
| Lymphocyte, PALS | +++ | +++ | − | − | − | +++ | +++ | +++ |
| Lymphocyte, follicle | + | + | − | − | − | + | + | + |
| Lymphocyte, red pulp | ++ | ++ | − | − | − | ++ | ++ | ++ |
| Other tissues | − | − | − | − | − | − | − | − |
| Liver | | | | | | | | |
| Lymphocyte, sinusoid | NA | NA | − | − | − | + | + | + |
| Other tissues | | | − | − | − | − | − | − |
| Kidney | NA | NA | | | | | | |

TABLE 1-continued hCD3. mCD3KCTG mouse
IACUC 14-074

| | | | | | | ± | ± | ± |
|---|---|---|---|---|---|---|---|---|
| Lymphocyte, interstitium | | | – | – | – | ± | ± | ± |
| Other tissues | | | – | – | – | – | – | – |
| Adrenal gland | NA | NA | | | | | | |
| Lymphocyte, interstitium | | | – | – | – | ± | ± | ± |
| Other tissues | | | – | – | – | – | – | – |
| Lung | NA | NA | | | | | | |
| Lymphocyte, alveolar wall | | | – | – | – | ± | ± | ± |
| Other tissues | | | – | – | – | – | – | – |
| Heart | NA | NA | | | | | | |
| Lymphocyte, interstitium | | | – | – | – | ± | ± | ± |
| Other tissues | | | – | – | – | – | – | – |
| Gastrocnemius muscle | NA | NA | – | – | – | – | – | – |

Findings:
–, negative;
±, very slight;
+, slight;
++, moderate;
+++, severe
IHC Staining:
–, negative;
±, rare;
+, occasional;
++, frequent;
+++, constant (8) Evaluation of Abundance Ratio of Mature T Cells in Human CD3 Gene-Substituted Mice FACS analyses were performed using spleen cells. Spleens were collected from mice (12 to 14-week old, male), and cells were isolated using 70 μm mesh. Erythrocytes were lysed by adding a hemolytic agent (manufactured by SIGMA). After blocking using an Fc blocking solution, FITC-labeled anti-mouse Cd3 antibody, FITC-labeled anti-human CD3 antibody, APC-labeled anti-mouse Cd4 antibody, and PE-labeled anti-mouse Cd8 antibody were used on $2\times10^6$ cells, and the respective positive cell counts were analyzed by a flow cytometer. It was revealed that the Cd3 gene-deficient mice nearly completely lack in mature T cells, that is, Cd4 and Cd8 single positive cells, while these cells were present in the human CD3 gene-substituted mice at a ratio equivalent to that in the wild-type.

Abundance Ratio of Mature T Cells

TABLE 2

| Experimental group | Number of samples | mCd3 | hCD3 | mCd4 | mCd8 |
|---|---|---|---|---|---|
| Human CD3s-substituded mouse #1C3 | n = 4 | ND. | 38.8 (±3.1) | 19.6 (±0.7) | 16.1 (±3.6) |
| Human CD3s-substituted mouse #4HH3 | n = 2 | ND. | 29.8, 28.9 | 15.5, 13.9 | 17.5, 16.4 |
| Human CD3s-substituted mouse #8I12 | n = 4 | ND. | 31.5 (±5.4) | 15.5 (±3.1) | 15.3 (±2.7) |
| hCD3E Tg mouse | n = 4 | 19.5 (±3.76) | 13.0 (±1.4) | 7.4 (±0.6) | 7.8 (±0.8) |
| Cd3s-deficient mouse | n = 4 | ND. | ND. | 1.8 (±1.3) | 2.1 (±0.6) |
| C57BL/6N | n = 4 | 40.4 (±8.42) | ND. | 20.3 (±6.7) | 12.7 (±2.1) |

The table shows the expression ratios of the respective marker-positive cells with respect to the spleen cells (unit were). The mean from four individuals is shown for each the experimental group, except for human CD3s-substituted mice #4HH3, and the expression ratios of two individuals are shown for line #4HH3. (The standard deviation is shown in parenthesis.) ND: not detected.

Figure 23:
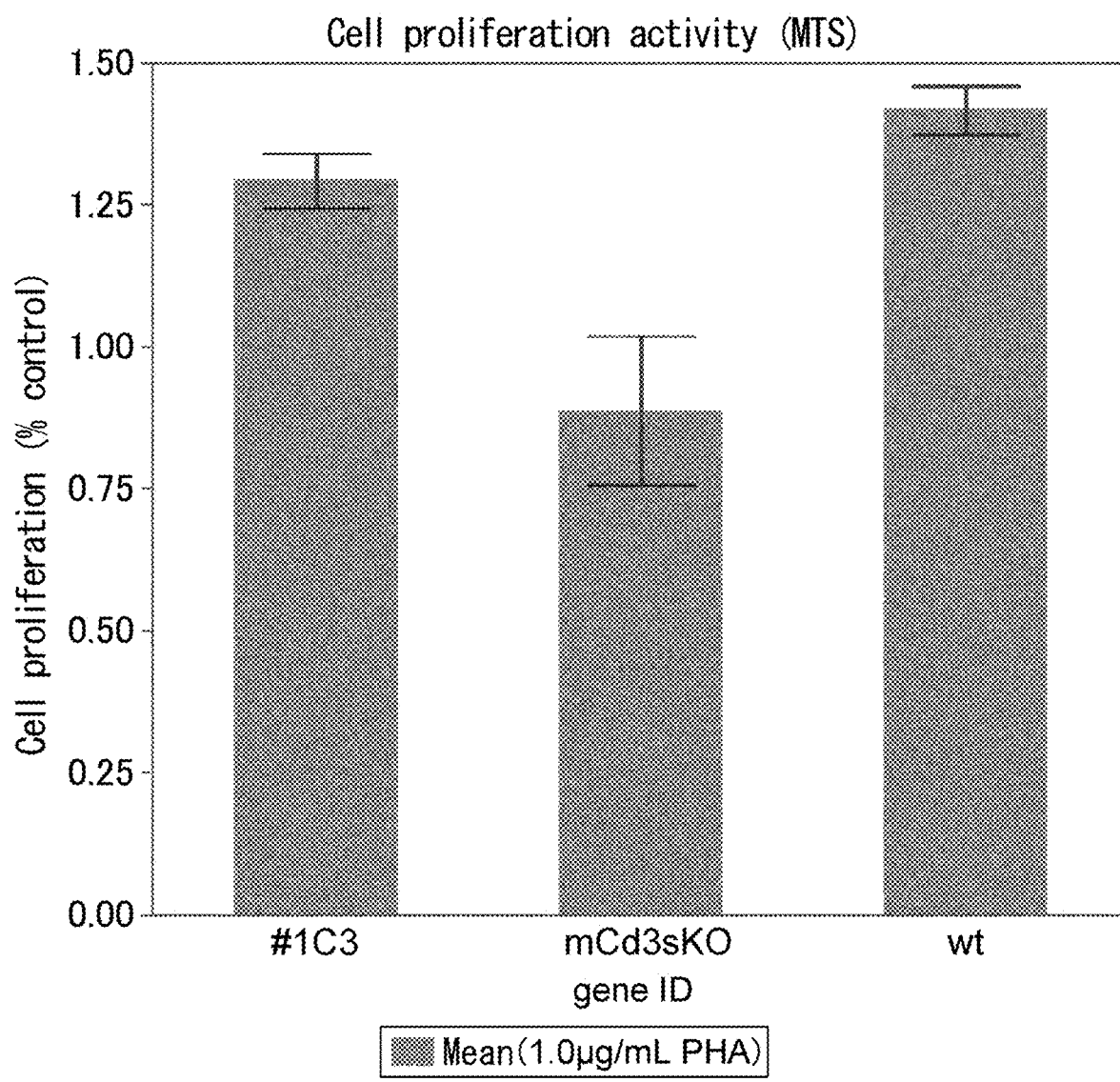
FIG. 23 presents the mitogen-stimulated cell proliferation activities of spleen cells from the human CD3 gene-substituted mice (1C3), Cd3 gene-deficient mice, and wild-type mice. The established human CD3 gene-substituted mice (1C3) showed 90% of cell proliferation activity compared to the wild type.

Example 7: Evaluation of Cell Proliferation Ability of Spleen Cells in Human Cd3 Aqueous One-Substituted Mice Spleens were collected from mice (12-week old, male), and cells were isolated using 70 μm mesh. Erythrocytes were lysed by adding a hemolytic agent (manufactured by SIGMA). Phytohaemagglutinin (PHA, manufactured by SIGMA) which is a T cell mitogen was added to the isolated spleen cells, and after culturing for five days, MTS assay was carried out using a cell proliferation assay reagent (Cell Titer 96. Aqueous One Solution Reagent, manufactured by Promega). Cell proliferation activities of the respective genotypes are shown as relative proportions by defining the activity without mitogen addition as 1 (FIG. 23).

As a result, in spleen cells of the Cd3 gene-deficient mice, cell proliferation activity in response to mitogen stimulation tended to decrease compared to that when mitogen was not added, and was approximately 60% of that of wild-type mice. On the other hand, in spleen cells of the human CD3 gene-substituted mice and wild-type mice, mitogen stimulation resulted in increase of cell proliferation activities, and the activities in the human CD3 gene-substituted mice were shown to be approximately 90% of that of the wild-type mice.

Figure 24:
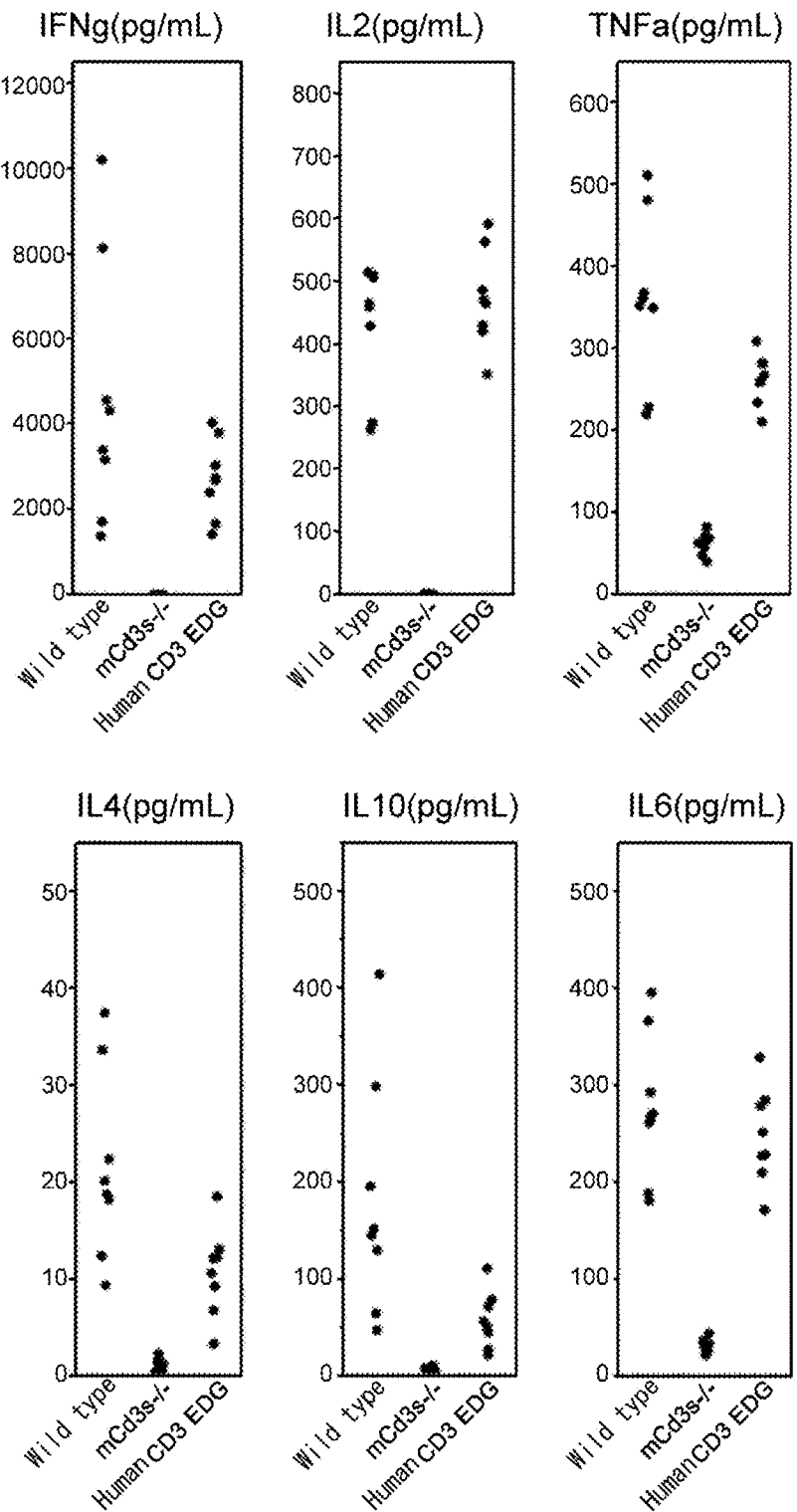
FIG. 24 presents the mitogen-stimulated cytokine production by spleen cells from the human CD3 gene-substituted mice (1C3), Cd3 gene-deficient mice, and wild-type mice. It was shown that cytokine-producing ability that was functionally lost in the Cd3 gene-deficient mice was recovered in the established human CD3 gene-substituted mice (1C3).

Example 8: Evaluation of Cytokine Production in Spleen Cells of Human CD3 Gene-Substituted Mice Spleen cells were prepared by collecting spleens from mice, isolating cells using 70 μm mesh, and lysing erythrocytes by adding a hemolytic agent. After culturing the cells for three days in the medium supplemented with phytohaemagglutinin (PHA) which is a T cell mitogen at a final concentration of 1 μg/mL, cytokines produced in the medium were measured (FIG. 24).

As a result, in spleen cells of the Cd3 gene-deficient mice, mitogen stimulated-cytokine production was not observed, whereas in the human CD3 gene-substituted mice, cytokine production was observed, indicating that the function of producing cytokines was restored.

Figure 25A:
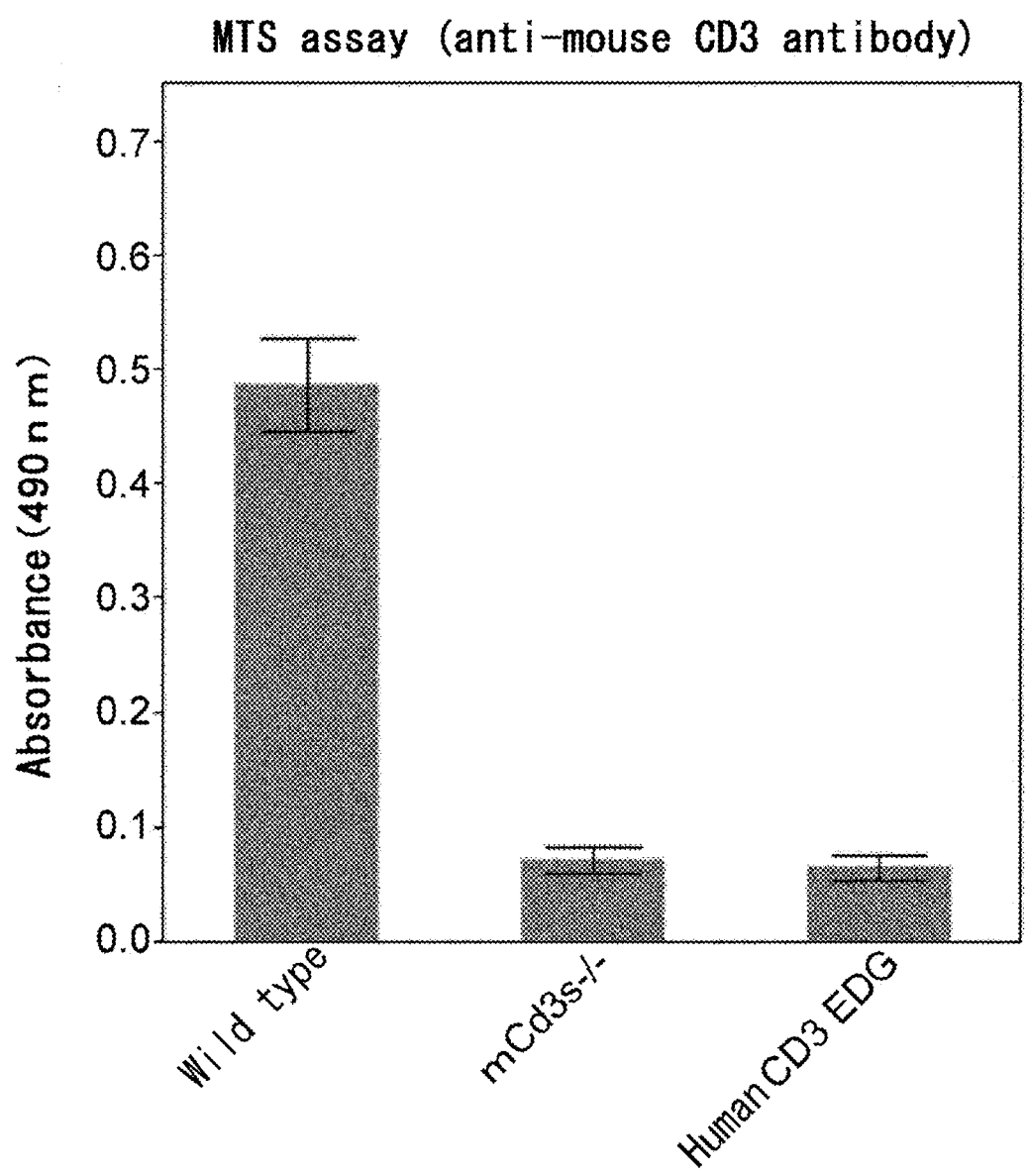
FIGS. 25A to 25D present the anti-CD3 antibody-stimulated cell proliferation activities (FIGS. 25A and 25B) and cytokine productions (FIGS. 25C and 25D) by spleen cells from the human CD3 gene-substituted mice (1C3), Cd3 gene-deficient mice, and wild-type mice. The established human CD3 gene-substituted mice (1C3) responded specifically to the anti-human CD3 antibody stimulation, and showed cell proliferation activity and cytokine production.
Figure 25B:
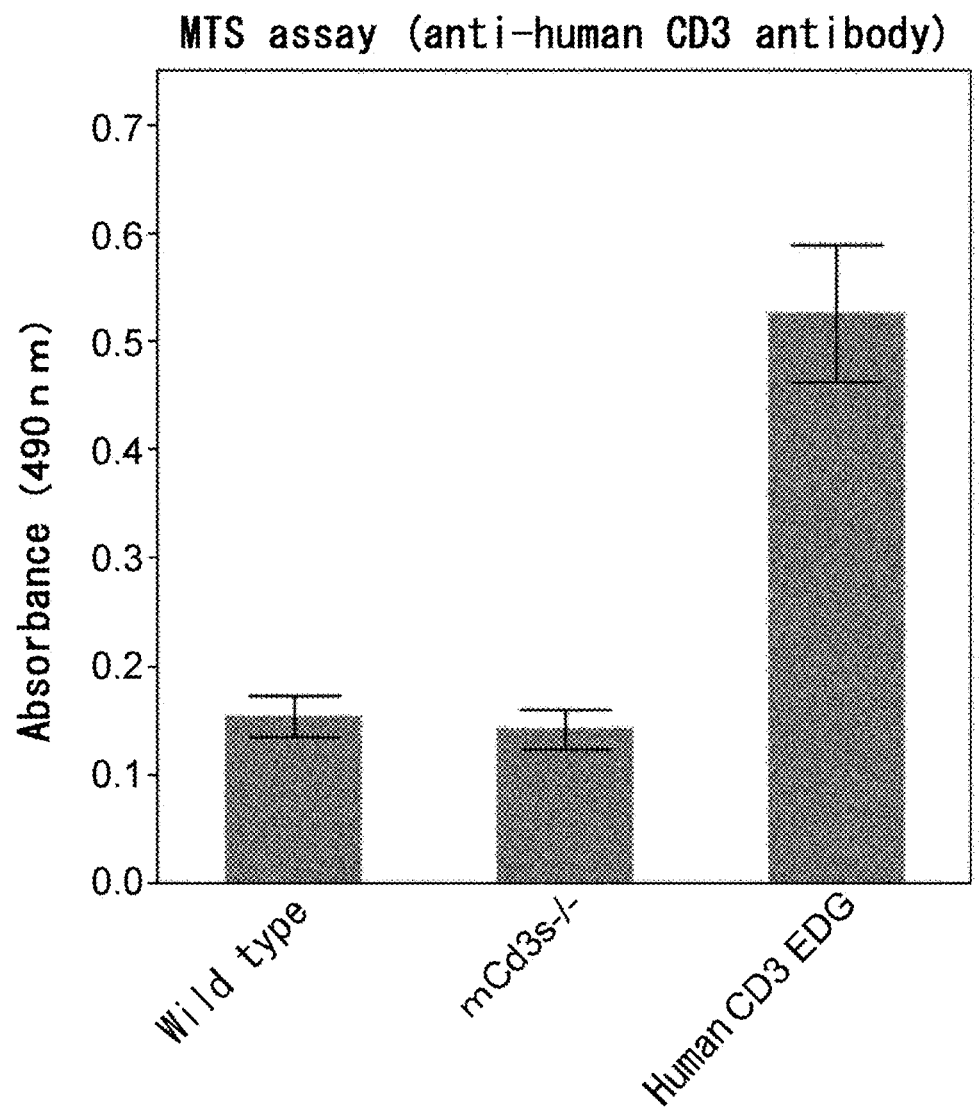
Figure 25C:
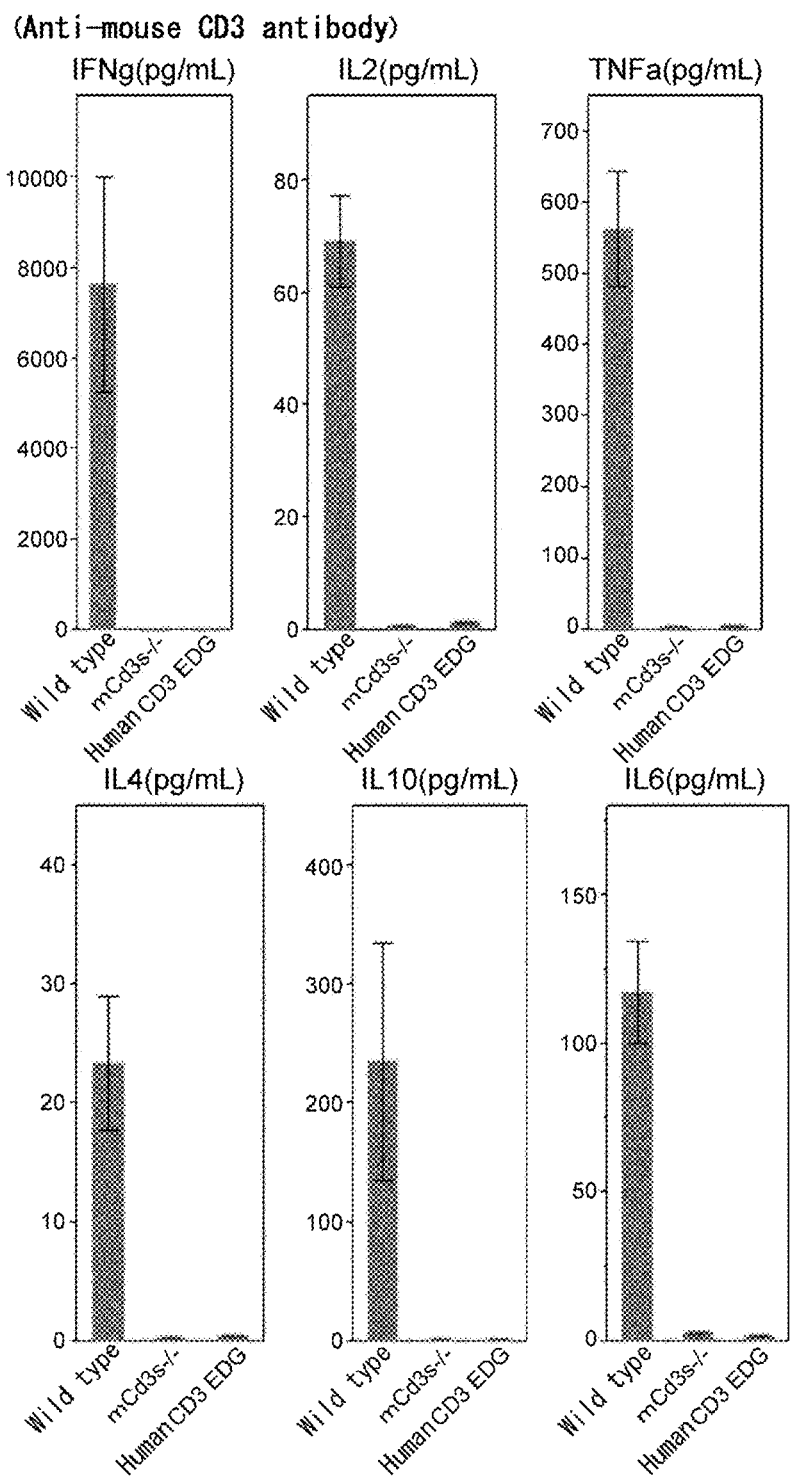

Example 9: Evaluation of Responsiveness to Human CD3 Antibody in Spleen Cells of Human CD3 Gene-Substituted Mice Spleen cells were prepared by collecting spleens from mice, isolating cells using 70 μm mesh, and lysing erythrocytes by adding a hemolytic agent. Cells were seeded into an anti-human CD3 antibody-coated plate, and MTS assay was performed to evaluate the cell proliferation activities after culturing for three days (FIGS. 25A and 25B). Cytokines produced in the culture medium were also measured (FIGS. 25C and 25D).

Figure 25D:
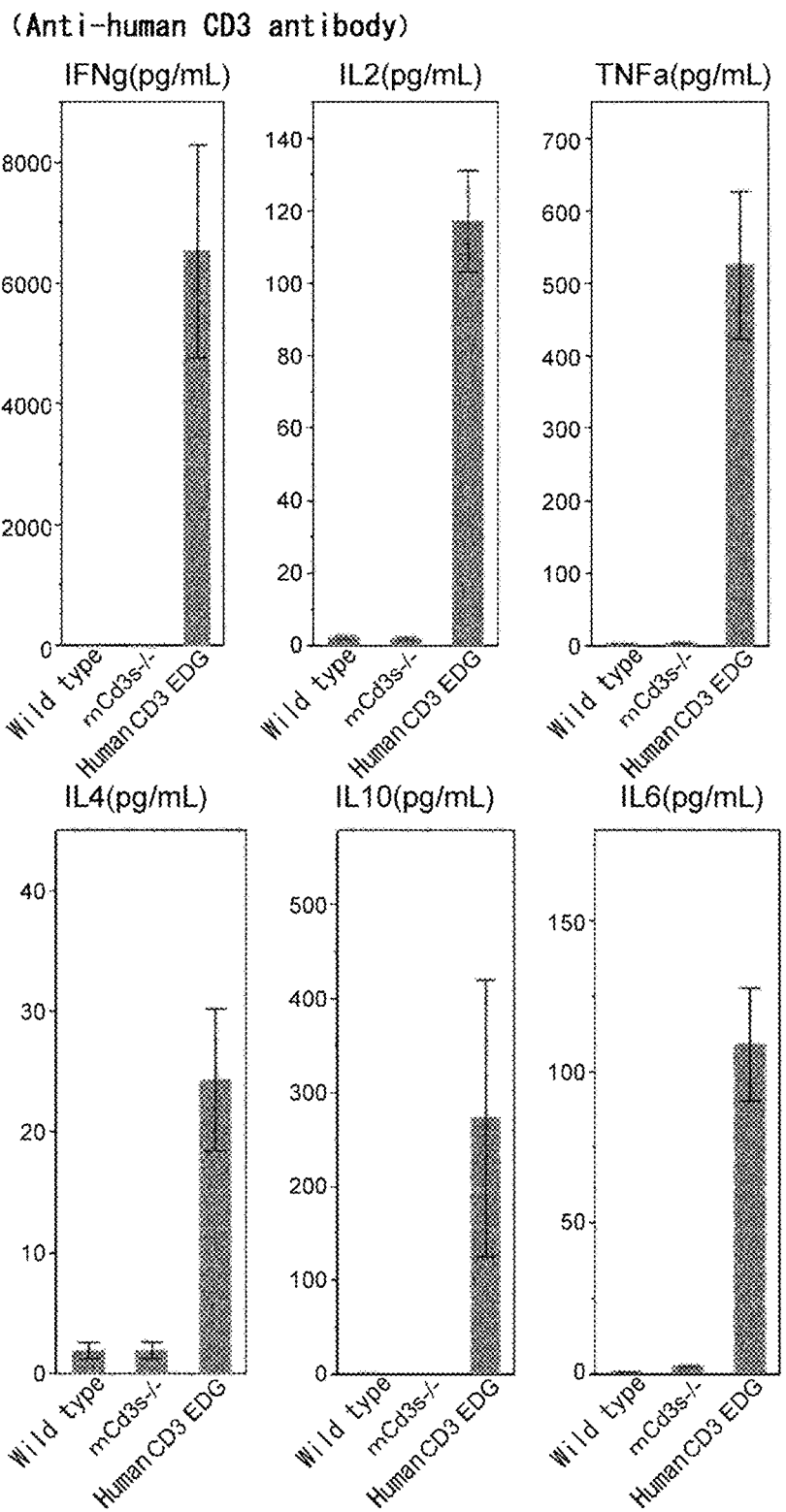

The results revealed that human CD3 gene-substituted mice responded specifically to stimulation by anti-human CD3 antibodies to exert cell proliferation activity (FIG. 25B) and cytokine production (FIG. 25D). Those levels were almost the same as the responsiveness of wild-type mice to anti-mouse CD3 antibody stimulation. These results showed that the human CD3 gene-substituted mice express human CD3ε having normal functions.

Example 10: Evaluation of Immune Function of Human CD3 Gene-Substituted Mice (1) Examination of the Ability to Produce Specific Antibodies in Response to Immunization to Foreign Antigen For production of specific antibodies against foreign antigens, there must exist functional helper T cells that can bind to antigenic peptides presented together with major histocompatibility complex (MHC) antigens on the surface of antigen-presenting cells such as dendritic cells, and the T cells must have functions of giving instructions to antibody-producing cells to produce appropriate antibodies. Whether the above-mentioned human CD3 gene-substituted mice carry helper T cells having normal functions and produce specific antibodies in response to immunization to foreign antigens was examined. Immunization was carried out using chicken ovalbumin (OVA) as the sensitizing antigen together with Freund's adjuvant. Immunization to OVA was performed twice with a four-week interval. More specifically, the first immunization was performed by subcutaneously applying, 100 μg of OVA per animal with complete Freund's adjuvant to the dorsal region, and four weeks later, similar immunization was performed by subcutaneously applying the antigen with incomplete Freund's adjuvant to the dorsal region. As human CD3 gene-substituted mice, two lines (line nos. 1C3 and 8I12), each of which is derived from a different modified ES cell clone, were selected, and compared to human CD3ε-overexpressing mice. Furthermore, as controls, wild-type mice and Cd3 gene-deficient mice were selected and similar antigen immunizations were performed.

Figure 26:
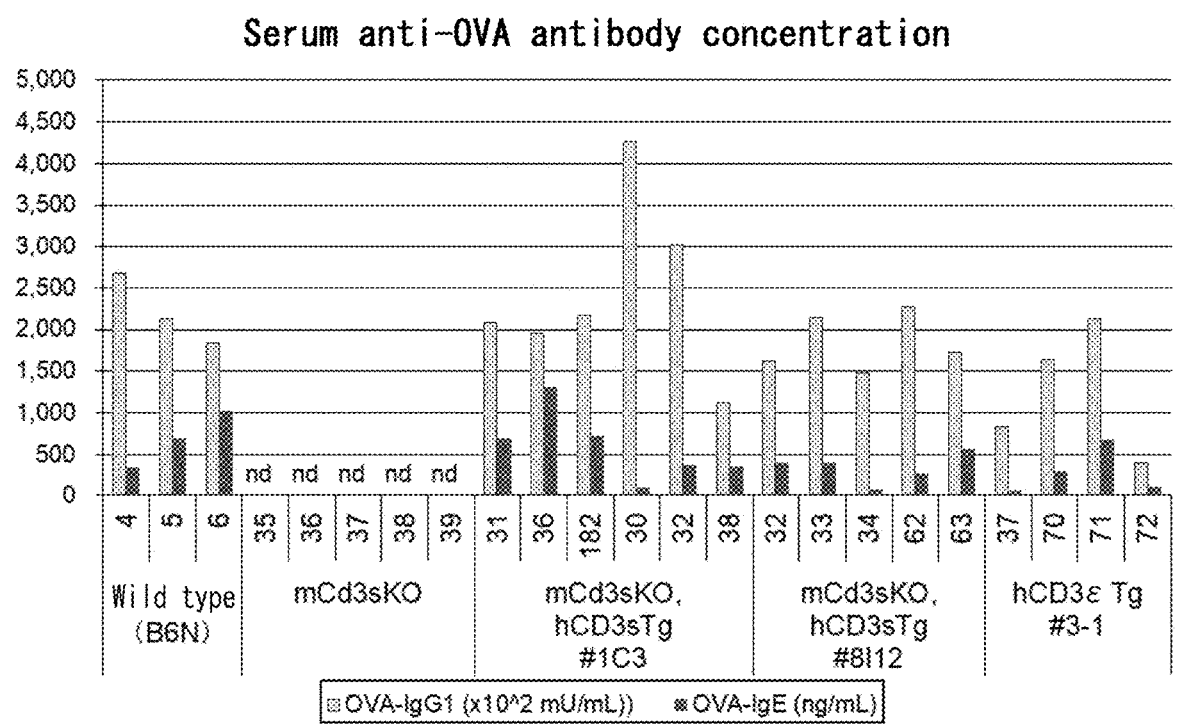
FIG. 26 presents the results of measuring the chicken ovoalbumin (OVA)-specific IgG1 and IgE serum concentrations in each established line of human CD3-substituted mice immunized with OVA. The OVA-specific serum IgG1 and IgE concentrations for each individual are shown as a bar graph. The numbers below the bar graph indicate the individual identification numbers.

One week after the second immunization, the animals were subjected to laparotomy under isoflurane anesthesia, and then euthanized by collecting whole blood and allowing bleeding from the abdominal vena cava. Serum was separated from the collected blood, and the concentrations of OVA-specific IgG1 and OVA-specific IgE were measured (FIG. 26).

As a result, neither IgG1 type nor IgE type OVA-specific antibodies were detected from the serum of mouse Cd3-deficient mice, whereas OVA-specific IgG1 and IgE were detected in both lines of the human CD3 gene-substituted mice, and their levels were equivalent to those of wild-type mice. These results showed that human CD3 gene-substituted mice have normal ability to produce antibodies in response to foreign antigen immunization.

Example 11: Antitumor Effects of Anti-Human HER2 Anti-Human CD3 Bispecific Antibodies on Human HER2-Expressing Mouse Hepatocellular Carcinoma Cell Line-Engrafted Model (1) Cell Line Hepa1-6 cells forced to express human HER2 (Hepa1-6/HER2) were used. The Hepa1-6/HER2 cells were maintained and passaged in Dulbecco's Modified Eagle's Medium (manufactured by SIGMA) containing 10% FBS (manufactured by BOVOGEN) and 0.5 mg/mL Zeocin (manufactured by Nacalai Tesque).

(2) Preparation of Hepa1-6/HER2 Engrafted Models

Hepa1-6/HER2 cells were prepared at $1 \times 10^8$ cells/mL in Dulbecco's Modified Eagle's Medium (manufactured by SIGMA) and MATRIGEL. A 100 μL portion of this cell suspension ($1 \times 10^7$ cells/mouse) was transplanted subcutaneously in the abdominal region of mCd3 KO homo, hCD3 Tg-type mouse #1C3 (19-week old). The tumor volume was calculated using the following equation, and when the tumor volume reached 160-234 mm³, the model was determined to be established.

Bispecific antibody against Her2 and CD3 (HER2_CD3 antibody) was prepared at 0.5 mg/mL using PBS(−) (5 mg/kg administration group). HER2_CD3 antibody (HER2-binding H chain variable region: SEQ ID NOs: 55 and 56; HER2-binding L chain variable region: SEQ ID NOs: 57 and 58; CD3-binding H chain variable region: SEQ ID NOs: 59 and 60; and CD3-binding L chain variable region: SEQ ID NOs: 61 and 62) was prepared according to a method known to those skilled in the art.

(4) Administration of a Pharmaceutical Agent

The Hepa1-6/HER2 engrafted models prepared in (2) were grouped according to the tumor volume, and the antibody samples prepared in the above-mentioned (3) were administered at 10 mL/kg through the tail vein. As a negative control, PBS(−) (Vehicle) was similarly administered at 10 mL/kg through the tail vein.

(5) Evaluation of Antitumor Effects

Figure 27:
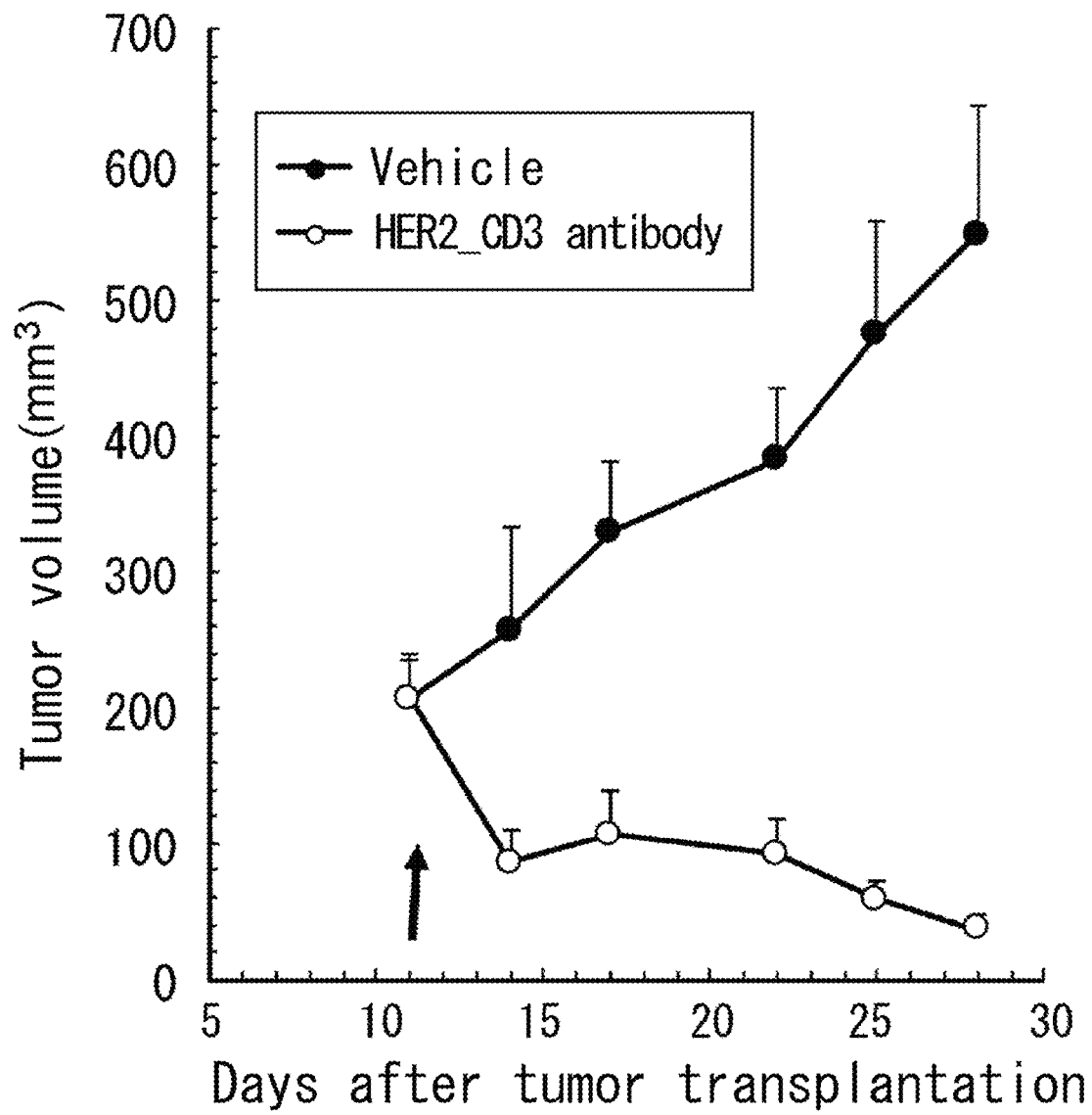
FIG. 27 presents the change in tumor volume in Hepa1-6/HER2 cell-transplanted hCD3 transgenic mouse model to which the HER2_CD3 antibody was administered. The arrow indicates antibody administration (*: P<0.05 (t-test))

The antitumor effect of the HER2_CD3 antibody in Hepa1-6/HER2 engrafted models was evaluated from the tumor volume at 28 days after transplantation (FIG. 27). JMP (SAS Institute Inc.) was used for statistical analysis, and the statistical analysis was confirmed by Wilcoxon test using the tumor volume on the final day of measurement. (Significance level was 5% on both sides.) As a result, tumor growth was found to be significantly inhibited by HER2_CD3 antibody administration.

Example 12: Antitumor Effects of Immune Checkpoint Inhibitors in Human Glypican 3 (GPC3)-Expressing Mouse Hepatocellular Carcinoma Cell Line-Engrafted Model (1) Cell Line
Hepa1-6 cells forced to express human GPC3 (Hepa1-6/hGPC3) were used. The Hepa1-6/hGPC3 cells were maintained and passaged in Dulbecco's Modified Eagle's Medium (manufactured by SIGMA) containing 10% FBS (manufactured by BOVOGEN) and 0.6 mg/mL G418 (manufactured by Nacalai Tesque).
(2) Preparation of Hepa1-6/hGPC3 Engrafted Model
Hepa1-6/hGPC3 cells were prepared at $5\times10^7$ cells/mL in Dulbecco's Modified Eagle's Medium (manufactured by SIGMA) and MATRIGEL. A 200 mL portion of this cell suspension ($1\times10^7$ cells/mouse) was transplanted subcutaneously in the abdominal region of mCd3 KO homo, hCD3 Tg-type mouse #1C3 (20-week old). The tumor volume was calculated using the following equation, and when the tumor volume reached 160-300 mm$^3$, the model was determined to be established.

Tumor volume=long diameter×short diameter×short diameter/2

Figure 28:
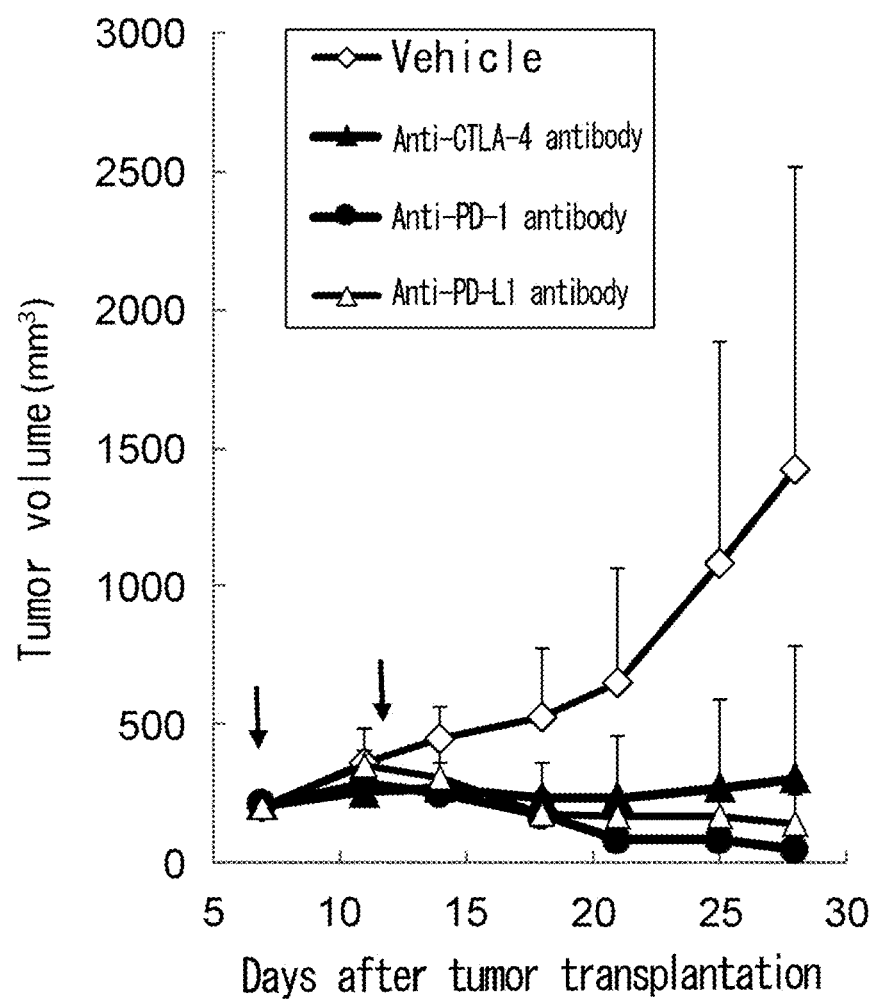
FIG. 28 presents the change in tumor volume in Hepa1-6/hGPC3 cell-transplanted hCD3 transgenic mouse model to which anti-mouse CTLA-4 antibody, anti-mouse PD-1 antibody, or anti-mouse PD-L1 antibody was administered. The arrows indicate antibody administration.

(3) Preparation of Pharmaceutical Agents for Administration
Anti-mouse CTLA-4 antibody (clone: UC10-4F10-11, manufactured by BioXcell), anti-mouse PD-1 antibody (clone: RMPI-14, manufactured by BioXcell), and anti-mouse PD-L1 antibody (clone: 10F.9G2, manufactured by BioXcell), which are immune checkpoint inhibitors, were prepared at 1 mg/mL (administration of 0.2 mg/head) using PBS(−).
(4) Administration of Pharmaceutical Agents
The Hepa1-6/hGPC3 engrafted models prepared in (2) were grouped according to the tumor volume, and the anti-mouse CTLA-4 antibodies, anti-mouse PD-1 antibodies, and anti-mouse PD-L1 antibodies prepared in the above-mentioned (3) were administered at 0.2 mL/mouse through the tail vein. As a negative control, PBS(−) (Vehicle) was similarly administered through the tail vein. The administration was carried out twice, which were 7 days (day of separation into groups) and 12 days (5 days after separation into groups) after tumor transplantation.
(5) Evaluation of Antitumor Effects
Antitumor effects in Hepa1-6/hGPC3 engrafted models were evaluated from the changes in tumor volume (FIG. 28). As a result, it was confirmed that tumor growth is inhibited by administration of the immune checkpoint inhibitors.

Example 13: Evaluation of In Vivo Drug Efficacy by Anti-Human CTLA4/Anti-Human CD3 Bispecific Antibody 13-1. Expression and Purification of a Bispecific Antibody that Binds Specifically to Human CTLA4 and Human CD3
Heavy chain variable region MDX10D1H (SEQ ID NO: 63) and light chain variable region MDX10D1L (SEQ ID NO: 64) were used for the anti-human CTLA4 arm. In that case, the constant regions used were heavy chain constant region mF18mN4 (SEQ ID NO: 65), which had been modified so that Fcγ receptor-binding is decreased and the two heavy chains undergo heterologous association, and light chain constant region mk1 (SEQ ID NO: 66). These genes were inserted into plasmids for expression in animals.
Heavy chain variable region TR01H113 (SEQ ID NO: 67) and light chain variable region L0011 (SEQ ID NO: 68) were used for the anti-human CD3 arm. In that case, the constant regions used were heavy chain constant region mFF18mP4 (SEQ ID NO: 69), which had been modified so that Fcγ receptor-binding is decreased and the two heavy chains undergo heterologous association, and light chain constant region mk1 (SEQ ID NO: 66). These genes were inserted into plasmids for expression in animals.
The anti-human CTLA4 antibody and the anti-human CD3 antibody were expressed using the following method. Cells of human embryonic kidney cell-derived FreeStyle 293-F strain (Invitrogen) were suspended in FreeStyle 293 Expression Medium (Invitrogen) at a cell density of 1.33× 10$^6$ cells/mL, and plated. The prepared plasmids were introduced into the cells by a lipofection method. The cells were cultured for four days in a CO$_2$ incubator (37° C., 8% CO$_2$, 90 rpm). From the culture supernatants, the antibodies were purified using Hi Trap™ Protein G HP column (GE Healthcare) by a method known to those skilled in the art. Absorbance of the purified antibody solutions at 280 nm were measured using a spectrophotometer. Concentrations of the purified antibodies were calculated from the obtained measurements using an extinction coefficient calculated by the PACE method (Protein Science (1995) 4: 2411-2423).
The respective purified homologous forms were mixed in the combinations shown in Table 3 by a method known to those skilled in the art (WO2015/046467) that utilizes charge differences of the constant regions to prepare the bispecific antibodies of interest.

TABLE 3

| No. | Clone name | Antibody 1 | Antibody 2 |
|---|---|---|---|
| 1 | MDX10//TR01H113 | MDX10-mF18mN4 | TR01H113/L0011-mF18mP4 |

13-2. Evaluation of Antitumor Effects in Syngeneic Tumor Line-Engrafted Mouse Model
13-2-1. Cell Line
Colon 38 cells transferred from the Japanese Foundation for Cancer Research were used. Colon 38 cells were maintained and passaged in RPMI1640 (manufactured by SIGMA) containing 10% FBS (manufactured by SIGMA).
13-2-2. Preparation of Syngeneic Tumor Line-Engrafted Mouse Model
A human CD3 gene-substituted and human CTLA4 gene-substituted mouse was established by crossing a human CD3 gene-substituted mouse with a human CTLA4 gene-substituted mouse (Blood 2005 106: 3127-3133), and used as a mouse model for evaluating antitumor effects.
Colon 38 was used as the tumor cell line to be transplanted autologously to mice. The cells were transplanted subcutaneously to the mice, and when the volume of the grafted tumor reached approximately 100 mm$^3$ or greater, the model was determined to be established. The volume of the grafted tumor was calculated by the following equation Tumor volume=long diameter×short diameter×short diameter/2

13-2-3. Preparation of Pharmaceutical Agents for Administration
Anti-human CTLA4/anti-human CD3 bispecific monoclonal antibody (MDX10//TR01H113) prepared in 13-1 was used as the pharmaceutical agent for administration to Colon 38 cell-engrafted models. Histidine buffer (150 mM NaCl/20 mM His-HCl buffer, pH 6.0; hereinafter, simply referred to as buffer) was used as the vehicle, and the antibody was prepared at 1000 μg/mL.
13-2-4. Administration of Pharmaceutical Agents
In the evaluation of the MDX10//TR01H113 antibody using Colon 38 cell-engrafted models, on the 12th day after transplantation, MDX10//TR01H113 was administered at 200 μg/mouse, or for the Control group (vehicle-administered group), the buffer was administered at 0.2 mL/mouse, through the tail vein.

Details relating to treatment with the pharmaceutical agents are shown in Table 4.

TABLE 4

Colon 38 cell-engrafted model (MDX10//TR01H113 administration experiment)

| Group | Number of animals | Pharmaceutical agent | Dose | Method of administration | Day of administration |
|---|---|---|---|---|---|
| 1 | 5 | Buffer | — | Tail vein | 12 days after transplantation |
| 2 | 5 | MDX10//TR01H113 | 200 μg/mouse | Tail vein | 12 days after transplantation |

13-2-5. Evaluation of Antitumor Effects

Antitumor effects were evaluated from the tumor volumes calculated using the equation shown in 8-2-2. JMPTM 11.2.1 (SAS Institute Inc.) was used for statistical analysis.

Figure 29:
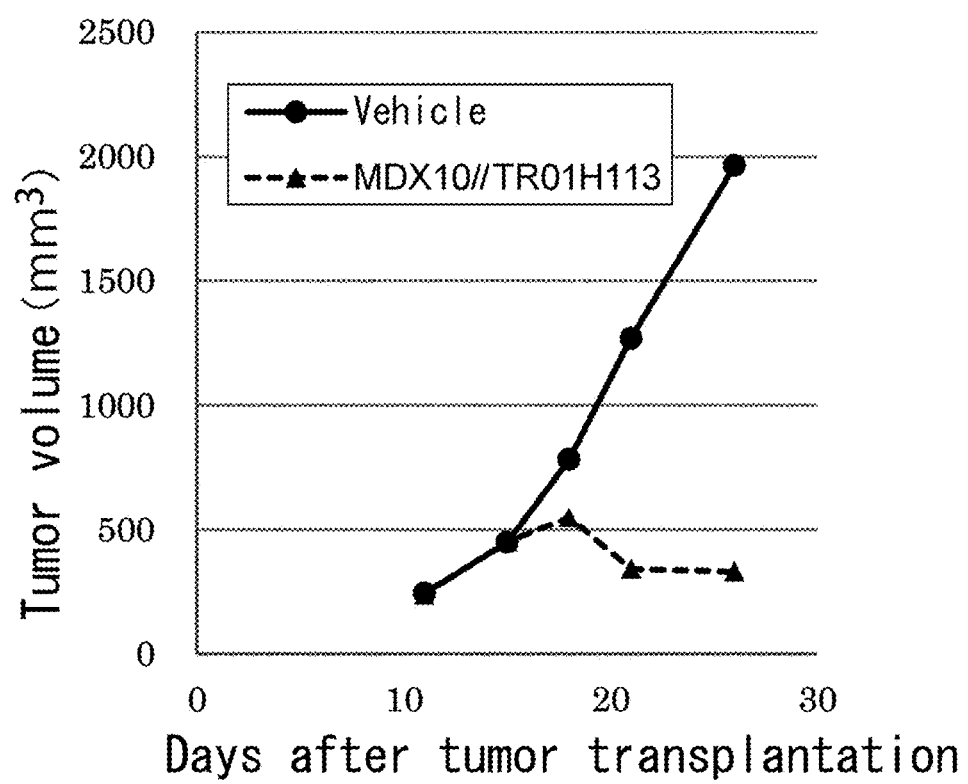
FIG. 29 presents the change in tumor volume in Colon 38 cell line-transplanted mouse model to which MDX10// TR01H113 or the buffer as a control (in the figure, referred to as "MDX10//TRO01H1333" and "vehicle", respectively) was administered. Each point shows the mean value of tumor volumes for n=5 per group. When the mean values were compared at the final measurement points, significant difference was observed between the two groups, the MDX10//TR01H113-administered group and the buffer-administered group (p=0.0021, Student's t-test).

As a result, compared to the control group, tumor growth was found to be significantly inhibited by anti-mouse CTLA4/CD3 bispecific monoclonal antibody administration (FIG. 29).

Example 14: Production of Human GPC3 Knock-In Human CD3 Gene-Substituted Mice

Human GPC3 knock-in mice and human CD3 gene-substituted mice were crossed, and by genotyping of the obtained next-generation animals, mouse strains in which the human GPC3 knock-in allele, mouse Cd3 gene region-deficient allele, and allele having a human CD3 gene region have been transmitted were established.

Example 15: Antitumor Studies of Anti-Human GPC3 Anti-Mouse CD3 Bispecific Antibodies Using Human GPC3-Knock-in Human CD3 Gene-Substituted Mice (1) Cell Line Hepa1-6 cells (Hepa1-6/hGPC3) forced to express human GPC3 in Hepa1-6 cells (obtainable from ATCC; ATCC number: CRL-1830) were used. Hepa1-6/hGPC3 cells were maintained and passaged in Dulbecco's Modified Eagle's Medium (manufactured by SIGMA) containing 10% FBS (manufactured by BIONET) and 0.6 mg/mL G418 (manufactured by Nacalai Tesque).

(2) Preparation of Hepa1-6/hGPC3 Engrafted Models

Hepa1-6/hGPC3 cells were prepared at $2\times10^8$ cells/mL in Dulbecco's Modified Eagle's Medium (manufactured by SIGMA) and an equivalent volume of Matrigel was added ($1\times10^8$ cells/mL). A 100 mL portion of this cell suspension ($1\times10^7$ cells/mouse) was transplanted subcutaneously in the abdominal region of human GPC3 knock-in human CD3 gene-substituted mice. The tumor volume was calculated using the following equation, and when the tumor volume reached approximately 160-360 mm³, the model was determined to be established.

Tumor volume=long diameter×short diameter×short diameter/2

(3) Preparation of a Pharmaceutical Agent for Administration

Bispecific antibody against human GPC3 and human CD3 (hGPC3_hCD3 antibody) was prepared at 0.5 mg/mL (5 mg/kg administration group), 0.1 mg/mL (1 mg/kg administration group), and 0.02 mg/mL (0.2 mg/kg administration group) using PBS(-). hGPC3_hCD3 antibody was prepared according to a method known to those skilled in the art using heavy chain variable region TR01H113 (SEQ ID NO: 67) and heavy chain constant region E2702sKsc (SEQ ID NO: 70) as the anti-human CD3 arm, heavy chain variable region GCH065 (SEQ ID NO: 71) and heavy chain constant region E2704sEpsc (SEQ ID NO: 72) as the anti-human GPC3 arm, and light chain variable region L0011 (SEQ ID NO: 73) and light chain constant region k0 (SEQ ID NO: 74) as the common light chain.

(4) Administration of a Pharmaceutical Agent

The Hepa1-6/hGPC3 engrafted models prepared in (2) above were grouped according to the tumor volume, and the antibody samples prepared in the above-mentioned (3) above were administered at 10 mL/kg through the tail vein. As a negative control, PBS(-) (Vehicle) was similarly administered at 10 mL/kg through the tail vein.

(5) Evaluation of Antitumor Effects

Figure 30:
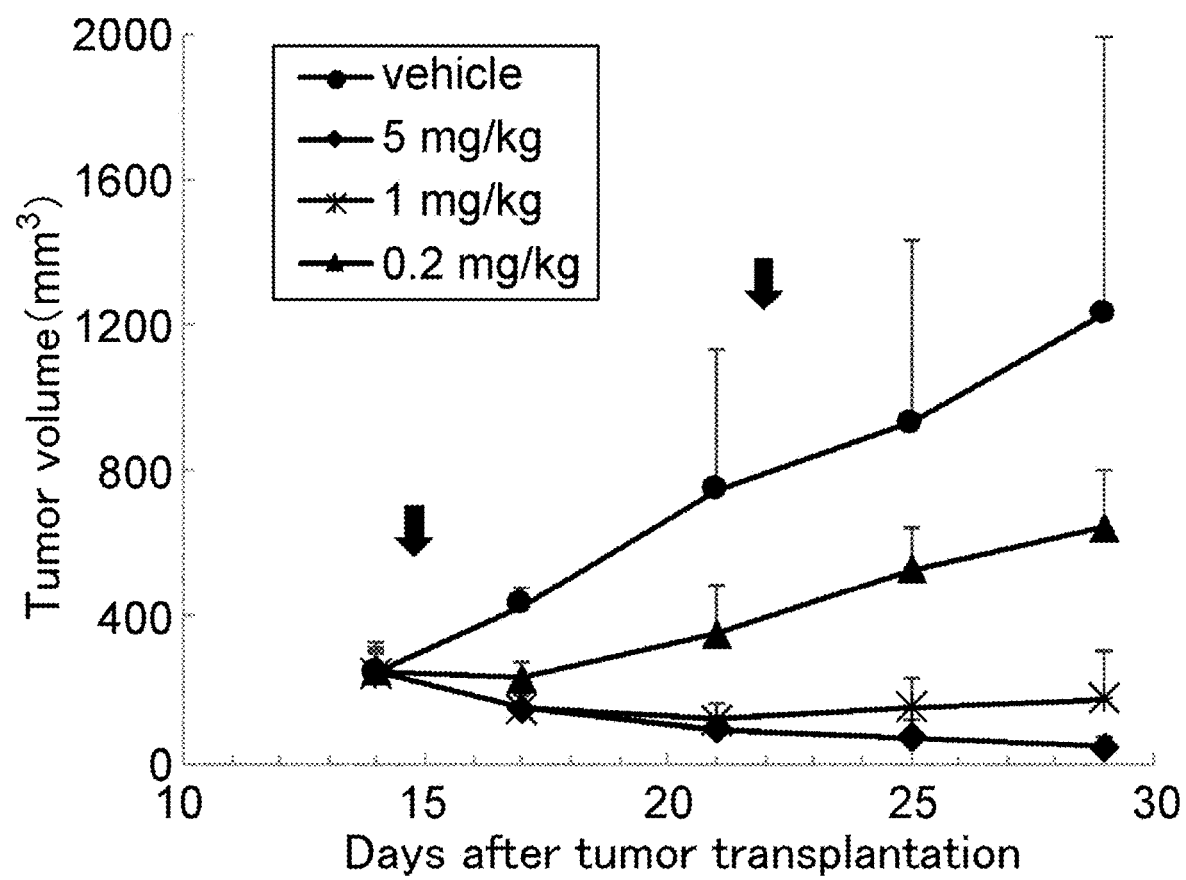
FIG. 30 shows the change in tumor volume in Hepa1-6/ hGPC3 cell-transplanted human GPC3 knock-in human CD3 gene-substituted mouse model to which the hGPC3_hCD3 antibody was administered. The arrows indicate antibody administration. *: P<0.05 (Steel test, JMP software, SAS institute Inc.)

The antitumor effect of the hGPC3_hCD3 antibody in Hepa1-6/hGPC3 engrafted models was evaluated from the tumor volume at 29 days after transplantation. As a result, tumor growth was found to be inhibited by hGPC3_hCD3 antibody administration in a dose-dependent manner (FIG. 30).

(6) Cytokine Release in hGPC3_hCD3 Antibody Administration

Figure 31:
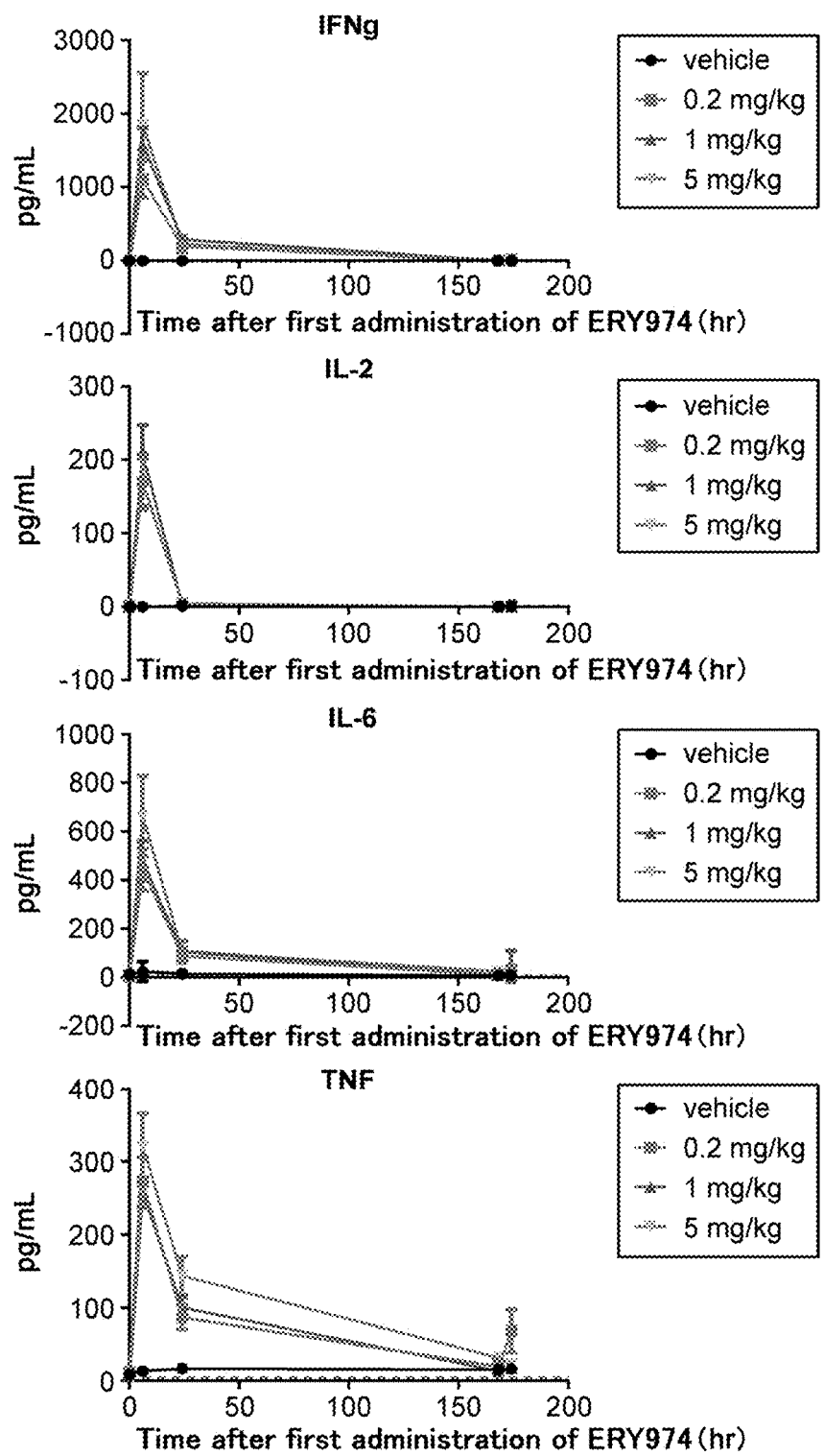
FIG. 31 shows the changes in blood plasma cytokine concentration in Hepa1-6/hGPC3 cell-transplanted human GPC3 knock-in human CD3 gene-substituted mouse model on the day before hGPC3_hCD3 antibody administration, and 6 hours and 24 hours after the administration, and 6 hours after the second administration. The broken lines indicate the detection limit.

Approximately 30 μL of blood was collected with heparin treatment to obtain plasma on the day before administration, and six hours and 24 hours after the first administration, on the day before the second administration, and six hours after the second administration. Using the obtained plasma samples, concentrations of IFNγ, IL-10, IL-17, IL-2, IL-4, IL-6, and TNF were determined using a BDTM cytometric bead array (CBA) mouse Th1/Th2/Th17 cytokine kit 2 (manufactured by BD Bioscience). As a result, hGPC3 antigen-dependent cytokine release was confirmed in human GPC3 knock-in human CD3 gene-substituted mice. However, cytokine release was hardly observed after the second administration (FIG. 31). Increase in cytokine is caused by activation of T cells due to binding of the hGPC3_hCD3 antibody to hGPC3 expressed in tissues. Increased cytokine in human GPC3 knock-in human CD3 gene-substituted mouse indicates that the knocked-in hGPC3 gene reflects the original characteristics of GPC3 expression, such as expression on the membrane, as in the hGPC3KI mice. Furthermore, when the anti-human GPC3 anti-human CD3 bispecific antibody was administered to monkeys, cytokine increase was observed; therefore, human GPC3 knock-in human CD3 gene-substituted mice were also considered to be mice with which pharmacological action as in humans and monkeys can be seen, and since they can be used to evaluate antibodies having a CD3 arm that cross-react with human and monkey, they were suggested to be useful for evaluation of their pharmacological actions, and usable in the development of pharmaceutical agents that act specifically to human-derived disease-related molecules.

INDUSTRIAL APPLICABILITY

The present invention provides genetically modified non-human animals which are deficient in expression of non-human animal endogenous GPC3 polypeptide and express human GPC3 polypeptide at a physiologically adequate level; methods for producing the non-human animals; and methods for evaluating test substances using the non-human animals. Therefore, the present invention can be used particularly for developing therapeutic agents for a disease including human GPC3 polypeptide-expressing cancer.

The invention claimed is:

1. A genetically modified mouse whose genome comprises a human glypican-3 (GPC3) gene-coding DNA sequence inserted between the translation start site and the translation stop codon of the endogenous GPC3 gene of the mouse,
    wherein the inserted DNA comprises the mouse beta globin second exon, the mouse beta globin second intron, and the mouse beta globin third exon 5' to the inserted human GPC3 gene-coding sequence as set forth in SEQ ID NO: 10 and an untranslated region of the mouse GPC3 gene 3' to the inserted human GPC3 gene-coding sequence,
    wherein the inserted DNA is in the same reading frame as the endogenous mouse GPC3 coding sequence,
    wherein the genetically modified mouse expresses human GPC3 polypeptide or human GPC3 mRNA in lung tissue at a level equivalent to the expression level of the human GPC3 polypeptide or human GPC3 mRNA in the lung tissue of a human; and
    wherein the mouse is deficient in expression of an endogenous GPC3 polypeptide.

2. The genetically modified mouse of claim 1, wherein the mouse shows immune tolerance to the human GPC3 polypeptide or a fragment thereof.

3. A lung tissue or cell isolated from the genetically modified mouse of claim 1, wherein the isolated lung tissue or cell expresses a human GPC3 polypeptide at a level equivalent to the expression level of the human GPC3 polypeptide in the corresponding lung tissue or cell of a human.

4. The genetically modified mouse of claim 1, wherein the mouse further comprises a human GPC3 polypeptide-expressing cancer tissue or cancer cell.

* * * * *

SEQUENCE LISTING

<160> NUMBER OF SEQ ID NOS: 74

<210> SEQ ID NO 1
<211> LENGTH: 580
<212> TYPE: PRT
<213> ORGANISM: Homo sapiens

<400> SEQUENCE: 1

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
                35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
        355                 360                 365

```
Asp Lys Lys Val Leu Lys Val Ala His Val Glu His Glu Glu Thr Leu
    370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
                405                 410                 415

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
        435                 440                 445

Glu Leu Lys Met Lys Gly Pro Glu Pro Val Val Ser Gln Ile Ile Asp
    450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
                485                 490                 495

Asp Cys Gly Asp Glu Asp Glu Cys Ile Gly Gly Ser Gly Asp Gly
            500                 505                 510

Met Ile Lys Val Lys Asn Gln Leu Arg Phe Leu Ala Glu Leu Ala Tyr
    515                 520                 525

Asp Leu Asp Val Asp Asp Ala Pro Gly Asn Ser Gln Gln Ala Thr Pro
530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580

<210> SEQ ID NO 2
<211> LENGTH: 580
<212> TYPE: PRT
<213> ORGANISM: Macaca fascicularis

<400> SEQUENCE: 2

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160
```

```
Ile Asn Val Asp Asp Met Val Asn Glu Leu Phe Asp Ser Leu Phe Pro
                165                 170                 175
Val Ile Tyr Thr Gln Leu Met Asn Pro Gly Leu Pro Asp Ser Ala Leu
            180                 185                 190
Asp Ile Asn Glu Cys Leu Arg Gly Ala Arg Arg Asp Leu Lys Val Phe
        195                 200                 205
Gly Asn Phe Pro Lys Leu Ile Met Thr Gln Val Ser Lys Ser Leu Gln
    210                 215                 220
Val Thr Arg Ile Phe Leu Gln Ala Leu Asn Leu Gly Ile Glu Val Ile
225                 230                 235                 240
Asn Thr Thr Asp His Leu Lys Phe Ser Lys Asp Cys Gly Arg Met Leu
                245                 250                 255
Thr Arg Met Trp Tyr Cys Ser Tyr Cys Gln Gly Leu Met Met Val Lys
            260                 265                 270
Pro Cys Gly Gly Tyr Cys Asn Val Val Met Gln Gly Cys Met Ala Gly
        275                 280                 285
Val Val Glu Ile Asp Lys Tyr Trp Arg Glu Tyr Ile Leu Ser Leu Glu
    290                 295                 300
Glu Leu Val Asn Gly Met Tyr Arg Ile Tyr Asp Met Glu Asn Val Leu
305                 310                 315                 320
Leu Gly Leu Phe Ser Thr Ile His Asp Ser Ile Gln Tyr Val Gln Lys
                325                 330                 335
Asn Ala Gly Lys Leu Thr Thr Thr Ile Gly Lys Leu Cys Ala His Ser
            340                 345                 350
Gln Gln Arg Gln Tyr Arg Ser Ala Tyr Tyr Pro Glu Asp Leu Phe Ile
        355                 360                 365
Asp Lys Lys Val Leu Lys Val Ala His Val Glu His Glu Glu Thr Leu
    370                 375                 380
Ser Ser Arg Arg Arg Glu Leu Ile Gln Lys Leu Lys Ser Phe Ile Ser
385                 390                 395                 400
Phe Tyr Ser Ala Leu Pro Gly Tyr Ile Cys Ser His Ser Pro Val Ala
                405                 410                 415
Glu Asn Asp Thr Leu Cys Trp Asn Gly Gln Glu Leu Val Glu Arg Tyr
            420                 425                 430
Ser Gln Lys Ala Ala Arg Asn Gly Met Lys Asn Gln Phe Asn Leu His
        435                 440                 445
Glu Leu Lys Met Lys Gly Pro Glu Pro Val Val Ser Gln Ile Ile Asp
    450                 455                 460
Lys Leu Lys His Ile Asn Gln Leu Leu Arg Thr Met Ser Val Pro Lys
465                 470                 475                 480
Gly Arg Val Leu Asp Lys Asn Leu Asp Glu Glu Gly Phe Glu Ser Gly
                485                 490                 495
Asp Cys Gly Asp Asp Glu Asp Glu Cys Ile Gly Gly Ser Gly Asp Gly
            500                 505                 510
Met Met Lys Val Lys Asn Gln Leu Arg Phe Leu Ala Glu Leu Ala Tyr
        515                 520                 525
Asp Leu Asp Val Asp Asp Val Pro Gly Asn Asn Gln Gln Ala Thr Pro
    530                 535                 540
Lys Asp Asn Glu Ile Ser Thr Phe His Asn Leu Gly Asn Val His Ser
545                 550                 555                 560
Pro Leu Lys Leu Leu Thr Ser Met Ala Ile Ser Val Val Cys Phe Phe
                565                 570                 575
```

```
Phe Leu Val His
            580

<210> SEQ ID NO 3
<211> LENGTH: 579
<212> TYPE: PRT
<213> ORGANISM: Mus musculus

<400> SEQUENCE: 3

Met Ala Gly Thr Val Arg Thr Ala Cys Leu Leu Val Ala Met Leu Leu
1               5                   10                  15

Gly Leu Gly Cys Leu Gly Gln Ala Gln Pro Pro Pro Pro Pro Asp Ala
            20                  25                  30

Thr Cys His Gln Val Arg Ser Phe Phe Gln Arg Leu Gln Pro Gly Leu
        35                  40                  45

Lys Trp Val Pro Glu Thr Pro Val Pro Gly Ser Asp Leu Gln Val Cys
50                  55                  60

Leu Pro Lys Gly Pro Thr Cys Cys Ser Arg Lys Met Glu Glu Lys Tyr
65                  70                  75                  80

Gln Leu Thr Ala Arg Leu Asn Met Glu Gln Leu Leu Gln Ser Ala Ser
                85                  90                  95

Met Glu Leu Lys Phe Leu Ile Ile Gln Asn Ala Ala Val Phe Gln Glu
            100                 105                 110

Ala Phe Glu Ile Val Val Arg His Ala Lys Asn Tyr Thr Asn Ala Met
        115                 120                 125

Phe Lys Asn Asn Tyr Pro Ser Leu Thr Pro Gln Ala Phe Glu Phe Val
130                 135                 140

Gly Glu Phe Phe Thr Asp Val Ser Leu Tyr Ile Leu Gly Ser Asp Ile
145                 150                 155                 160

Asn Val Asp Asp Met Val Asn Glu Leu Phe Asp Ser Leu Phe Pro Val
                165                 170                 175

Ile Tyr Thr Gln Met Met Asn Pro Gly Leu Pro Glu Ser Val Leu Asp
            180                 185                 190

Ile Asn Glu Cys Leu Arg Gly Ala Arg Arg Asp Leu Lys Val Phe Gly
        195                 200                 205

Ser Phe Pro Lys Leu Ile Met Thr Gln Val Ser Lys Ser Leu Gln Val
210                 215                 220

Thr Arg Ile Phe Leu Gln Ala Leu Asn Leu Gly Ile Glu Val Ile Asn
225                 230                 235                 240

Thr Thr Asp His Leu Lys Phe Ser Lys Asp Cys Gly Arg Met Leu Thr
                245                 250                 255

Arg Met Trp Tyr Cys Ser Tyr Cys Gln Gly Leu Met Met Val Lys Pro
            260                 265                 270

Cys Gly Gly Tyr Cys Asn Val Val Met Gln Gly Cys Met Ala Gly Val
        275                 280                 285

Val Glu Ile Asp Lys Tyr Trp Arg Glu Tyr Ile Leu Ser Leu Glu Glu
290                 295                 300

Leu Val Asn Gly Met Tyr Arg Ile Tyr Asp Met Glu Asn Val Leu Leu
305                 310                 315                 320

Gly Leu Phe Ser Thr Ile His Asp Ser Ile Gln Tyr Val Gln Lys Asn
                325                 330                 335

Gly Gly Lys Leu Thr Thr Thr Ile Gly Lys Leu Cys Ala His Ser Gln
            340                 345                 350

Gln Arg Gln Tyr Arg Ser Ala Tyr Tyr Pro Glu Asp Leu Phe Ile Asp
        355                 360                 365
```

Lys Lys Ile Leu Lys Val Ala His Val Glu His Glu Thr Leu Ser
370                 375                 380

Ser Arg Arg Arg Glu Leu Ile Gln Lys Leu Lys Ser Phe Ile Asn Phe
385                 390                 395                 400

Tyr Ser Ala Leu Pro Gly Tyr Ile Cys Ser His Ser Pro Val Ala Glu
                405                 410                 415

Asn Asp Thr Leu Cys Trp Asn Gly Gln Glu Leu Val Glu Arg Tyr Ser
                420                 425                 430

Gln Lys Ala Ala Arg Asn Gly Met Lys Asn Gln Phe Asn Leu His Glu
            435                 440                 445

Leu Lys Met Lys Gly Pro Glu Pro Val Val Ser Gln Ile Ile Asp Lys
450                 455                 460

Leu Lys His Ile Asn Gln Leu Leu Arg Thr Met Ser Val Pro Lys Gly
465                 470                 475                 480

Lys Val Leu Asp Lys Ser Leu Asp Glu Glu Gly Leu Glu Ser Gly Asp
                485                 490                 495

Cys Gly Asp Asp Glu Asp Glu Cys Ile Gly Ser Ser Gly Asp Gly Met
                500                 505                 510

Val Lys Val Lys Asn Gln Leu Arg Phe Leu Ala Glu Leu Ala Tyr Asp
            515                 520                 525

Leu Asp Val Asp Ala Pro Gly Asn Lys Gln His Gly Asn Gln Lys
530                 535                 540

Asp Asn Glu Ile Thr Thr Ser His Ser Val Gly Asn Met Pro Ser Pro
545                 550                 555                 560

Leu Lys Ile Leu Ile Ser Val Ala Ile Tyr Val Ala Cys Phe Phe Phe
                565                 570                 575

Leu Val His

<210> SEQ ID NO 4
<211> LENGTH: 2329
<212> TYPE: DNA
<213> ORGANISM: Homo sapiens

<400> SEQUENCE: 4
agccccgccc tgccccgcgc cgccaagcgg ttcccgccct cgcccagcgc ccaggtagct    60
gcgaggaaac ttttgcagcg gctgggtagc agcacgtctc ttgctcctca gggccactgc   120
caggcttgcc gagtcctggg actgctctcg ctccggctgc cactctcccg cgctctccta   180
gctccctgcg aagcaggatg gccgggaccg tgcgcaccgc gtgcttggtg gtggcgatgc   240
tgctcagctt ggacttcccg ggacaggcgc agccccgcc gccgccgccg gacgccacct   300
gtcaccaagt ccgctccttc ttccagagac tgcagcccgg actcaagtgg gtgccagaaa   360
ctcccgtgcc aggatcagat tgcaagtat gtctccctaa gggcccaaca tgctgctcaa   420
gaaagatgga agaaaaatac caactaacag cacgattgaa catggaacag ctgcttcagt   480
ctgcaagtat ggagctcaag ttcttaatta ttcagaatgc tgcggttttc caagaggcct   540
ttgaaattgt tgttcgccat gccaagaact acaccaatgc catgttcaag aacaactacc   600
caagcctgac tccacaagct tttgagtttg tgggtgaatt tttcacagat gtgtctctct   660
acatcttggg ttctgacatc aatgtagatg acatggtcaa tgaattgttt gacagcctgt   720
ttccagtcat ctatacccag ctaatgaacc aggcctgcc tgattcagcc ttggacatca   780
atgagtgcct ccgaggagca agacgtgacc tgaaagtatt tgggaatttc cccaagctta   840
ttatgaccca ggtttccaag tcactgcaag tcactaggat cttccttcag gctctgaatc   900

```
ttggaattga agtgatcaac acaactgatc acctgaagtt cagtaaggac tgtggccgaa      960
tgctcaccag aatgtggtac tgctcttact gccagggact gatgatggtt aaaccctgtg     1020
gcggttactg caatgtggtc atgcaaggct gtatggcagg tgtggtggag attgacaagt     1080
actggagaga atacattctg tcccttgaag aacttgtgaa tggcatgtac agaatctatg     1140
acatggagaa cgtactgctt ggtctctttt caacaatcca tgattctatc cagtatgtcc     1200
agaagaatgc aggaaagctg accaccacta ttggcaagtt atgtgcccat tctcaacaac     1260
gccaatatag atctgcttat tatcctgaag atctctttat tgacaagaaa gtattaaaag     1320
ttgctcatgt agaacatgaa gaaaccttat ccagccgaag aagggaacta attcagaagt     1380
tgaagtcttt catcagcttc tatagtgctt tgcctggcta catctgcagc catagccctg     1440
tggcggaaaa cgacacccct tgctggaatg acaagaact cgtggagaga tacagccaaa      1500
aggcagcaag gaatggaatg aaaaaccagt tcaatctcca tgagctgaaa atgaagggcc     1560
ctgagccagt ggtcagtcaa attattgaca aactgaagca cattaaccag ctcctgagaa     1620
ccatgtctat gcccaaaggt agagttctgg ataaaaacct ggatgaggaa gggtttgaaa     1680
gtggagactg cggtgatgat gaagatgagt gcattggagg ctctggtgat ggaatgataa     1740
aagtgaagaa tcagctccgc ttccttgcag aactggccta tgatctggat gtggatgatg     1800
cgcctggaaa cagtcagcag gcaactccga aggacaacga gataagcacc tttcacaacc     1860
tcgggaacgt tcattcccccg ctgaagcttc tcaccagcat ggccatctcg gtggtgtgct    1920
tcttcttcct ggtgcactga ctgcctggtg cccagcacat gtgctgccct acagcaccct    1980
gtggtcttcc tcgataaagg gaaccacttt cttattttt tctattttt tttttttgtt       2040
atcctgtata cctcctccag ccatgaagta gaggactaac catgtgttat gttttcgaaa    2100
atcaaatggt atcttttgga ggaagataca ttttagtggt agcatataga ttgtccttt      2160
gcaaagaaag aaaaaaaacc atcaagttgt gccaaattat tctcctatgt ttggctgcta    2220
gaacatggtt accatgtctt tctctctcac tccctccctt tctatcgttc tctctttgca    2280
tggatttctt tgaaaaaaaa taaattgctc aaataaaaaa aaaaaaaa                  2329
```

<210> SEQ ID NO 5
<211> LENGTH: 2566
<212> TYPE: DNA
<213> ORGANISM: Macaca fascicularis

<400> SEQUENCE: 5

```
gtagagcggc ggcgaacggg cagcttggct cggctgccgg gagccaccgc gcgcgctccg       60
caccctcctc tcgcactgtc tccgcccggt ccccgcacgc ggtgccctag tggccccgc       120
cgccctccac gccgcgcccc cgcacccgc aggctaccgg ctgcacaacc gccgccgcc        180
cctggccgcg cggctcgcct cgccccgccc cgtctctcct cgctccgccc caccccagtc      240
agccccgccc tgccccgcgc cgccaagcgg ttcccgccct cgcccagcgc ccaggtagct      300
gcgaggaaac ttttgcagcg gctgggtagc agcacgtctc ttgctccaca gggccactgc      360
caggcttgcc gagtcctggg actgctctcg ctccggctgc cactctcctg cgctctccta      420
gctccctgcg aagcaggatg gccgggaccg tgcgcaccgc gtgcttggtg gtggcgatgc      480
tgctcagctt ggacttcccc ggacaggcgc agccccgcc gccgcgcccg gacgccacct      540
gtcaccaagt ccgctccttc ttccagagac tgcagcccgg actcaagtgg gtgcccgaaa     600
ctcccgtgcc aggatcagat ttgcaagtat gtctccctaa gggcccaaca tgctgctcaa     660
```

| gaaagatgga agaaaaatac caactaacag cacgattgaa catggaacag ctgcttcagt | 720 |
| ctgcaagtat ggagctcaag ttcttaatta ttcagaatgc tgcagttttc caagaggcct | 780 |
| ttgaaattgt tgttcgccat gccaagaact acaccaatgc catgttcaag aacaactacc | 840 |
| caagcctgac tccacaagct tttgagtttg tgggtgaatt tttcacagat gtgtctctct | 900 |
| atatcttggg ttctgacatc aatgtggatg acatggtcaa tgaattgttt gatagcctgt | 960 |
| ttccagtcat ctatacccaa ctaatgaacc aggtctgcc tgattcagcc ttggacatca | 1020 |
| atgagtgcct ccgaggagca agacgtgacc tgaaagtatt tgggaacttc cccaagctta | 1080 |
| ttatgaccca ggtttctaag tcactgcaag tcactaggat cttccttcag gctctgaatc | 1140 |
| ttggaattga agtgatcaac acaaccgatc acctgaagtt cagtaaggac tgtggccgaa | 1200 |
| tgctcaccag aatgtggtac tgctcttact gccagggact gatgatggtt aaaccttgtg | 1260 |
| gtggttactg caatgtggtc atgcaaggct gtatggcagg tgtggtggag attgacaagt | 1320 |
| actggagaga atacattctg tctcttgaag agcttgtgaa tggcatgtac agaatctatg | 1380 |
| acatggaaaa cgtactgctt ggtctctttt caacaatcca cgattctatc cagtatgtcc | 1440 |
| agaagaatgc aggaaagctg accaccacta ttggcaagtt atgtgcccat tctcaacaac | 1500 |
| gccaatatag atctgcttat tatcctgaag atctgtttat tgacaagaaa gtattaaaag | 1560 |
| ttgctcatgt agaacatgaa gaaaccttat ccagccgaag aagggaacta attcagaagt | 1620 |
| tgaagtcttt catcagcttc tatagtgctt tgcctggcta catctgcagc catagccctg | 1680 |
| tggcggaaaa cgacaccctt tgctggaatg acaagaact cgtggagaga tacagccaaa | 1740 |
| aggcggcaag gaatggaatg aaaaaccagt tcaatctcca tgagctgaaa atgaagggcc | 1800 |
| ctgagccagt agtcagtcaa attattgaca aattgaagca cattaaccag ctcctgagaa | 1860 |
| ccatgtctgt gcccaaaggt agagttctgg ataaaaaccct ggatgaggaa gggttttgaaa | 1920 |
| gtggagactg tggtgatgat gaagatgagt gcattggagg ctctggtgat ggaatgatga | 1980 |
| aagtgaagaa tcagctccgc ttccttgcag aactggccta tgatctggat gtggatgatg | 2040 |
| tgcctggaaa caatcagcag gcgactccga aggacaatga gataagcacc tttcacaacc | 2100 |
| ttgggaacgt tcattcccg ctgaagcttc tcaccagcat ggccatctca gtggtgtgct | 2160 |
| tcttcttcct ggtgcactga ctgcctggtg cccagcacat gtgctgccct acagcaccct | 2220 |
| gtggtcttcc tcgataaagg gaaccacttt cttatttttt tcttttttttt ttttttatcc | 2280 |
| tgtataccct ctccagccat taagtagaag actaaccatg tgttatgttt ttgaaaatca | 2340 |
| aatggtatct tttggaggaa gataaatttt agtggtagta tatagattgt ccttttgcaa | 2400 |
| agaaaagaaa accatcaagt tgtgccaaat tattttccta tgtttggctg ctagaacatg | 2460 |
| gttaccatgt ctttctctct gtcttactcc ctccctttct atctttcttt ctctctctct | 2520 |
| ttgcatggat ttctttgaaa aaaaaaataa attgctcaaa taaaaa | 2566 |

<210> SEQ ID NO 6
<211> LENGTH: 2272
<212> TYPE: DNA
<213> ORGANISM: Mus musculus

<400> SEQUENCE: 6

| tgttcccgcc ctcgcccagc gcccaggtag ctgcgaggaa acttttgcgg cggctgggta | 60 |
| gcggctcctc tcttgctctg tcgggctact gccagacttg ctgagtctcg ggaccgctcc | 120 |
| ggctcttatt gccactctct cgtgctctcc tcgctccccc aagaagcagg atggccggga | 180 |
| ccgtgcgcac cgcgtgcttg ctggtggcga tgctgctagg cttgggctgc ctgggacagg | 240 |

```
cgcagccccc gccgcctcca gacgccacct gtcaccaggt ccgttctttc ttccagagac    300
tgcagcccgg actcaaatgg gttccagaaa cccctgtacc aggatcagat ttgcaagtat    360
gtctccccaa gggcccaaca tgctgctcaa gaaagatgga agaaaaatac caactaacag    420
cacggctgaa catggaacaa ctgctccagt ctgcgagtat ggaactcaag ttcttaatta    480
ttcagaatgc tgcggttttc aagaggcctt tgaaattgt tgttcgccat gccaagaact    540
acaccaacgc catgttcaag aataactacc ccagcctgac tccacaagct tttgagtttg    600
tcggtgaatt tttcacagat gtgtctctct acatcttggg ttctgatatc aacgtggatg    660
atatggtcaa tgaattgttc gacagcctct ttccagtcat ctacacccag atgatgaacc    720
caggcctgcc tgagtcagtc ttagacatca acgagtgcct ccgaggagca agacgtgacc    780
tgaaagtatt tggcagtttc cccaagctta ttatgaccca ggtttccaag tcactgcaag    840
tcactcgaat cttccttcaa gccctgaatc tcggaattga agtcatcaac actaccgacc    900
acctcaagtt tagtaaggac tgtggccgta tgctcacccg aatgtggtat tgctcttact    960
gccagggact gatgatggtt aagccttgcg gtggttattg caatgtggtc atgcaaggct   1020
gtatggctgg tgtggtggag atcgacaagt actggagaga atacattctg tctcttgaag   1080
agctcgtgaa tggcatgtac agaatctacg acatggagaa tgtgctgctc ggcctctttt   1140
ctaccatcca tgattccatc cagtatgtgc agaagaacgg aggcaagctg accaccacca   1200
ttggcaagtt gtgtgcccac tcccagcaac gccaatatag atctgcttat taccctgaag   1260
atctgtttat tgacaagaag atattaaaag tcgctcatgt cgaacatgaa gaaacccttat  1320 ccagccgaag aagggaactg attcagaaac tgaagtcttt catcaacttc tatagcgctt   1380
tgccgggcta catctgcagc catagccccg tggccgaaaa tgatacccctg tgctggaacg   1440 gacaagaact tgtggagaga tacagccaga aggcggcaag gaacgggatg aagaatcagt   1500
ttaacctcca tgagctgaaa atgaagggcc ctgagccggt ggttagccag atcattgaca   1560
aactgaagca cattaaccag ctcctgagaa ccatgtctgt gcccaagggt aaagttctgg   1620
ataaaagcct ggatgaagaa ggacttgaaa gtggagactg cggtgatgat gaagatgaat   1680
gcattggaag ctctggtgac gggatggtga agtgaagaa tcaactgcgc ttccttgcag   1740
aactggccta tgatctggat gtggacgatg ctccggggaa caagcagcat ggaaatcaga   1800
aggacaacga gatcaccacc tctcacagcg tggggaacat gccgtcccca ctgaagatcc   1860
tcatcagtgt ggccatctat gtggcgtgct ttttttttcct ggtgcactga cttgccagcg   1920
tccagtgcct gtgctgccct gcagcacctg tggtccctac agaaagggag ccaccttctt   1980 tttttttct tttttttttt tttttatct tttatgcctc ctcccaccac cattaagtag     2040
gagactaacc gcgtgttatg ttttcgaaaa tcaaatggta tctttatgag gatggtaaat    2100
tttagtggta ggatagattg tcttttttgca agaaaaaaa aaaccttcaa gttgtgccaa    2160
attattttct tacatttgac tgttggaaca tggttgtcat gtttccctct tttctctttc    2220
tctgcatgga tttctttgac aaaaaaaaat aaataaacat tcaaataaaa aa            2272
```

<210> SEQ ID NO 7
<211> LENGTH: 34
<212> TYPE: DNA
<213> ORGANISM: Bacteriophage P1

<400> SEQUENCE: 7
ataacttcgt atagcataca ttatacgaag ttat                                34

<210> SEQ ID NO 8
<211> LENGTH: 32
<212> TYPE: DNA
<213> ORGANISM: Bacteriophage D6

<400> SEQUENCE: 8
taactttaaa taattggcat tatttaaagt ta                                   32

<210> SEQ ID NO 9
<211> LENGTH: 34
<212> TYPE: DNA
<213> ORGANISM: Saccharomyces cerevisiae

<400> SEQUENCE: 9
gaagttccta ttctctagaa agtataggaa cttc                                 34

<210> SEQ ID NO 10
<211> LENGTH: 1743
<212> TYPE: DNA
<213> ORGANISM: Homo sapiens

<400> SEQUENCE: 10

```
atggccggga ccgtgcgcac cgcgtgcttg gtggtggcga tgctgctcag cttggacttc     60
ccgggacagg cgcagccccc gccgccgccg ccggacgcca cctgtcacca gtccgctcc     120 ttcttccaga gactgcagcc cggactcaag tgggtgccag aaactcccgt gccaggatca    180
gatttgcaag tatgtctccc taagggccca acatgctgct caagaaagat ggaagaaaaa    240
taccaactaa cagcacgatt gaacatggaa cagctgcttc agtctgcaag tatggagctc    300
aagttcttaa ttattcagaa tgctgcggtt tccaagaggc cttttgaaat tgttgttcgc    360
catgccaaga actacaccaa tgccatgttc aagaacaact acccaagcct gactccacaa    420
gcttttgagt ttgtgggtga atttttcaca gatgtgtctc tctacatctt gggttctgac    480
atcaatgtag atgacatggt caatgaattg tttgacagcc tgtttccagt catctatacc    540
cagctaatga acccaggcct gcctgattca gccttggaca tcaatgagtg cctccgagga    600
gcaagacgtg acctgaaagt atttgggaat tcccccaagc ttattatgac ccaggttttcc    660 aagtcactgc aagtcactag atcttccttc aggctctga atcttggaat tgaagtgatc     720
aacacaactg atcacctgaa gttcagtaag gactgtggcc aatgctcac cagaatgtgg     780 tactgctctt actgccaggg actgatgatg gttaaaccct gtggcggtta ctgcaatgtg     840
gtcatgcaag gctgtatggc aggtgtggtg gagattgaca gtactggag agaatacatt     900 ctgtcccttg aagaacttgt gaatggcatg tacagaatct atgacatgga aacgtactg     960 cttggtctct tttcaacaat ccatgattct atccagtatg tccagaagaa tgcaggaaag   1020
ctgaccacca ctattggcaa gttatgtgcc cattctcaac aacgccaata tagatctgct   1080
tattatcctg aagatctctt tattgacaag aaagtattaa aagttgctca tgtagaacat   1140
gaagaaacct tatccagccg aagaagggaa ctaattcaga agttgaagtc tttcatcagc   1200
ttctatagtg ctttgcctgg ctacatctgc agccatagcc ctgtggcgga aaacgacacc   1260
ctttgctgga tggacaaga actcgtggag agatacagcc aaaaggcagc aaggaatgga   1320
atgaaaaacc agttcaatct ccatgagctg aaaatgaagg gccctgagcc agtggtcagt   1380
caaattattg acaaactgaa gcacattaac cagctcctga gaaccatgtc tatgcccaaa   1440
ggtagagttc tggataaaaa cctggatgag gaagggtttg aaagtggaga ctgcggtgat   1500
gatgaagatg agtgcattgg aggctctggt gatggaatga taaaagtgaa gaatcagctc   1560
```

-continued

```
cgcttccttg cagaactggc ctatgatctg gatgtggatg atgcgcctgg aaacagtcag    1620
caggcaactc cgaaggacaa cgagataagc acctttcaca acctcgggaa cgttcattcc    1680
ccgctgaagc ttctcaccag catggccatc tcggtggtgt gcttcttctt cctggtgcac    1740
tga                                                                  1743
```

<210> SEQ ID NO 11
<211> LENGTH: 40
<212> TYPE: DNA
<213> ORGANISM: Artificial Sequence
<220> FEATURE:
<223> OTHER INFORMATION: an artificially synthesized sequence

<400> SEQUENCE: 11

```
ggggcgcgtg gtggcggctg cagccgccac cacgcgcccc                            40
```

<210> SEQ ID NO 12
<211> LENGTH: 122
<212> TYPE: DNA
<213> ORGANISM: Unknown
<220> FEATURE:
<223> OTHER INFORMATION: an artificially synthesized sequence

<400> SEQUENCE: 12

```
gcgggactct ggggttcgaa taaagaccga ccaagcgacg tctgagagct ccctggcgaa      60
ttcggtacca ataaaagagc tttatttca tgatctgtgt gttggttttt gtgtgcggcg     120
cg                                                                   122
```

<210> SEQ ID NO 13
<211> LENGTH: 1513
<212> TYPE: DNA
<213> ORGANISM: Escherichia coli

<400> SEQUENCE: 13

```
ctaccgggta ggggaggcgc ttttcccaag gcagtctgga gcatgcgctt tagcagcccc      60
gctgggcact tggcgctaca caagtggcct ctggcctcgc acacattcca catccaccgg    120
taggcgccaa ccggctccgt tctttggtgg ccccgtcgcg ccaccttcta ctcctcccct    180
agtcaggaag ttccccccg ccccgcagct cgcgtcgtgc aggacgtgac aaatggaagt    240
agcacgtctc actagtctcg tgcagatgga cagcaccgct gagcaatgga agcgggtagg    300
cctttggggc agcggccaat agcagctttg ctccttcgct ttctgggctc agaggctggg    360
aaggggtggg tccgggggcg ggctcagggg cgggctcagg ggcggggcgg gcgcccgaag    420
gtcctccgga ggcccggcat tctgcacgct tcaaaagcgc acgtctgccg cgctgttctc    480
ctcttcctca tctccgggcc tttcgacctg cagcagcacg tgttgacaat taatcatcgg    540
catagtatat cggcatagta taatacgaca aggtgaggaa ctaaaccatg ggatcggcca    600
ttgaacaaga tggattgcac gcaggttctc cggccgcttg ggtggagagg ctattcggct    660
atgactgggc acaacagacg atcggctgct ctgatgccgc cgtgttccgg ctgtcagcgc    720
aggggcgccc ggttcttttt gtcaagaccg acctgtccgg tgccctgaat gaactgcagg    780
acgaggcagc gcggctatcg tggctggcca cgacgggcgt tccttgcgca gctgtgctcg    840
acgttgtcac tgaagcggga agggactggc tgctattggg cgaagtgccg gggcaggatc    900
tcctgtcatc tcaccttgct cctgccgaga agtatccat catggctgat gcaatgcggc    960
ggctgcatac gcttgatccg gctacctgcc cattcgacca ccaagcgaaa catcgcatcg   1020
```

```
agcgagcacg tactcggatg gaagccggtc ttgtcgatca ggatgatctg gacgaagagc    1080
atcaggggct cgcgccagcc gaactgttcg ccaggctcaa ggcgcgcatg cccgacggcg    1140
aggatctcgt cgtgacccat ggcgatgcct gcttgccgaa tatcatggtg gaaaatggcc    1200
gcttttctgg attcatcgac tgtggccggc tgggtgtggc ggaccgctat caggacatag    1260
cgttggctac ccgtgatatt gctgaagagc ttggcggcga atgggctgac cgcttcctcg    1320
tgctttacgg tatcgccgcc cccgattcgc agcgcatcgc cttctatcgc cttcttgacg    1380
agttcttctg agcgggactc tggggttcga ataaagaccg accaagcgac gtctgagagc    1440
tccctggcga attcggtacc aataaaagag ctttatttc atgatctgtg tgttggtttt     1500
tgtgtgcggc gcg                                                        1513

<210> SEQ ID NO 14
<211> LENGTH: 20
<212> TYPE: DNA
<213> ORGANISM: Mus musculus

<400> SEQUENCE: 14
tggatcctga gaacttcagg                                                   20

<210> SEQ ID NO 15
<211> LENGTH: 654
<212> TYPE: DNA
<213> ORGANISM: Mus musculus

<400> SEQUENCE: 15
gtgagtctga tgggcacctc ctgggtttcc ttcccctggc tattctgctc aaccttccta      60
tcagaaggaa aggggaagcg attctaggga gcagtctcca tgactgtgtg tggagtgttg     120
acaagagttt ggatatttta ttctctactc agaatcgctg ctccccctca ctctgttctg     180
tgttgtcatt tcctctttct ttggtaagct tttaatttcc agttgcattt tactaaatta     240
attaagctgg ttatttactt cccatcctga tatcagcttc ccctcctcct ttcctcccag     300
tccttctctc tctcctctct ctttctctaa tccttccctt tccctcagtt catttcttct     360
tctttgatct acttttgttt gtcttttta aatattgcctt gtaacttact cagaggacaa     420
ggaagatatg tccctgtttc ttctcatagc tctcaagaat agtagcataa ttggcttta      480 tgccagggtg acaggggaag aatatatttt acatataaat tctgtttgac ataggattct     540
tataataatt tgtcagcagt ttaaggttgc aaacaaatgt ctttataaat aagcctgcag     600
tatctggtat ttttgctcta cagttatgtt gatggttctt ccatattccc acag           654

<210> SEQ ID NO 16
<211> LENGTH: 871
<212> TYPE: DNA
<213> ORGANISM: Mus musculus

<400> SEQUENCE: 16
ctcctgggca atcggaattc gcggccgcga tcgtgattgt gctgggccac caccttggca      60
aggatttcac ccccgctgca caggctgcct tccagaaggt ggtggctgga gtggccgctg     120
ccctggctca caagtaccac taaaccccct ttcctgctct tgcctgtgaa caatggttaa     180
ttgttcccaa gagagcatct gtcagttgtt ggcaaaatga taaagacatt tgaaaatctg     240
tcttctgaca aataaaaagc atttatttca ctgcaatgat gttttaaatt atttgtctgt     300
gtcatagaag ggtttatgct aagttttcaa gatacaaaga agtgagggtt caggtctgac     360
cttggggaaa taaatgaatt acacttcaaa tgtatgggac agcaagcagt aagccacaga     420
```

```
tcctattgcc atgccctaaa cactcagaga aaaattcaac aaatggtttc atttatacac    480
tacattatga ttcattttta tgtaaattat ttgttttttc tactcttcca cataaatgtc    540 ttttttcct  cttacctacc cagcacttca cagttctcaa gccataatt  tttcttttgt    600 aaaattacca ttattctcta aacttttccc tctgtgttta ccaagcaaca ttatttatct    660
tttcataaat cctgttgcct tagacagctc caatagcaat agaggtatga ttaaggagag    720
aatagaagtg ccctgtttgt cataccatgc ctgcacagtc aatagtcact atgagatttc    780
aaatggcact ttgcctggga cctttacacc tcacaccata ctctggcttg agttaggagt    840
taagaatgag agaaatataa gatctgtcga c                                  871
```

<210> SEQ ID NO 17
<211> LENGTH: 359
<212> TYPE: DNA
<213> ORGANISM: Mus musculus

<400> SEQUENCE: 17

```
cttgccagcg tccagtgcct gtgctgccct gcagcacctg tggtccctac agaaagggag     60
ccaccttctt ttttttttct tttttttttt tttttatct  tttatgcctc ctcccaccac    120
cattaagtag gagactaacc gcgtgttatg ttttcgaaaa tcaatggta  tctttatgag    180 gatggtaaat tttagtggta ggatagattg tcttttgca  aagaaaaaaa aaaccttcaa    240
gttgtgccaa attattttct tacatttgac tgttggaaca tggttgtcat gtttccctct    300
tttctctttc tctgcatgga tttctttgac aaaaaaaaat aaataaacat tcaaataaa    359
```

<210> SEQ ID NO 18
<211> LENGTH: 31
<212> TYPE: DNA
<213> ORGANISM: Artificial Sequence
<220> FEATURE:
<223> OTHER INFORMATION: an artificially synthesized sequence

<400> SEQUENCE: 18

```
agatggctgc ctgtgacatt tctggaagtg t                                   31
```

<210> SEQ ID NO 19
<211> LENGTH: 30
<212> TYPE: DNA
<213> ORGANISM: Artificial Sequence
<220> FEATURE:
<223> OTHER INFORMATION: an artificially synthesized sequence

<400> SEQUENCE: 19

```
ctgaattagt tcccttcttc ggctggataa                                     30
```

<210> SEQ ID NO 20
<211> LENGTH: 26
<212> TYPE: DNA
<213> ORGANISM: Artificial Sequence
<220> FEATURE:
<223> OTHER INFORMATION: an artificially synthesized sequence

<400> SEQUENCE: 20

```
atgagaccca gcaagctaca cgggct                                         26
```

<210> SEQ ID NO 21
<211> LENGTH: 24
<212> TYPE: DNA
<213> ORGANISM: Artificial Sequence
<220> FEATURE:

<223> OTHER INFORMATION: an artificially synthesized sequence

<400> SEQUENCE: 21
acttgagctc catacttgca gact                                          24

<210> SEQ ID NO 22
<211> LENGTH: 25
<212> TYPE: DNA
<213> ORGANISM: Artificial Sequence
<220> FEATURE:
<223> OTHER INFORMATION: an artificially synthesized sequence

<400> SEQUENCE: 22
tgatgatgaa gatgagtgca ttgga                                         25

<210> SEQ ID NO 23
<211> LENGTH: 23
<212> TYPE: DNA
<213> ORGANISM: Artificial Sequence
<220> FEATURE:
<223> OTHER INFORMATION: an artificially synthesized sequence

<400> SEQUENCE: 23
tggccagaac tacgggtcca gct                                           23

<210> SEQ ID NO 24
<211> LENGTH: 23
<212> TYPE: DNA
<213> ORGANISM: Artificial Sequence
<220> FEATURE:
<223> OTHER INFORMATION: an artificially synthesized sequence

<400> SEQUENCE: 24
agggccctga gccagtggtc agt                                           23

<210> SEQ ID NO 25
<211> LENGTH: 23
<212> TYPE: DNA
<213> ORGANISM: Artificial Sequence
<220> FEATURE:
<223> OTHER INFORMATION: an artificially synthesized sequence

<400> SEQUENCE: 25
tagcggctcc tctcttgctc tgt                                           23

<210> SEQ ID NO 26
<211> LENGTH: 30
<212> TYPE: DNA
<213> ORGANISM: Artificial Sequence
<220> FEATURE:
<223> OTHER INFORMATION: an artificially synthesized sequence

<400> SEQUENCE: 26
gcccggggca tgtggacaga gtcccatact                                    30

<210> SEQ ID NO 27
<211> LENGTH: 21
<212> TYPE: DNA
<213> ORGANISM: Artificial Sequence
<220> FEATURE:
<223> OTHER INFORMATION: an artificially synthesized sequence

<400> SEQUENCE: 27
gaaaccttat ccagccgaag a                                             21

```
<210> SEQ ID NO 28
<211> LENGTH: 19
<212> TYPE: DNA
<213> ORGANISM: Artificial Sequence
<220> FEATURE:
<223> OTHER INFORMATION: an artificially synthesized sequence

<400> SEQUENCE: 28
gcaaagggtg tcgttttcc                                                   19

<210> SEQ ID NO 29
<211> LENGTH: 20
<212> TYPE: DNA
<213> ORGANISM: Artificial Sequence
<220> FEATURE:
<223> OTHER INFORMATION: an artificially synthesized sequence

<400> SEQUENCE: 29
caggtagctg cgaggaaact                                                  20

<210> SEQ ID NO 30
<211> LENGTH: 20
<212> TYPE: DNA
<213> ORGANISM: Artificial Sequence
<220> FEATURE:
<223> OTHER INFORMATION: an artificially synthesized sequence

<400> SEQUENCE: 30
ccgacagagc aagagaggag                                                  20

<210> SEQ ID NO 31
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 31
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly

```
                180                 185                 190
Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Arg Gly Gly Pro Lys Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ala Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Tyr Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Glu Ser Leu Ser Leu Ser Pro
            435                 440

<210> SEQ ID NO 32
<211> LENGTH: 219
<212> TYPE: PRT
<213> ORGANISM: Artificial Sequence
<220> FEATURE:
<223> OTHER INFORMATION: an artificially synthesized sequence

<400> SEQUENCE: 32

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
```

```
            100                 105                 110
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 33
<211> LENGTH: 444
<212> TYPE: PRT
<213> ORGANISM: Artificial Sequence
<220> FEATURE:
<223> OTHER INFORMATION: an artificially synthesized sequence

<400> SEQUENCE: 33

```
Glu Val Gln Leu Val Glu Ser Gly Gly Gly Leu Val Gln Pro Gly Lys
1               5                   10                  15

Ser Leu Lys Leu Ser Cys Glu Ala Ser Gly Phe Thr Phe Ser Gly Tyr
            20                  25                  30

Gly Met His Trp Val Arg Gln Ala Pro Gly Arg Gly Leu Glu Ser Val
        35                  40                  45

Ala Tyr Ile Thr Ser Ser Ile Asn Ile Lys Tyr Ala Asp Ala Val
    50                  55                  60

Lys Gly Arg Phe Thr Val Ser Arg Asp Asn Ala Lys Asn Leu Leu Phe
65                  70                  75                  80

Leu Gln Met Asn Ile Leu Lys Ser Glu Asp Thr Ala Met Tyr Tyr Cys
                85                  90                  95

Ala Arg Phe Asp Trp Asp Lys Asn Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Arg Gly Gly Pro Lys Val Phe
225                 230                 235                 240

Leu Phe Pro Pro Lys Pro Lys Asp Thr Leu Met Ile Ser Arg Thr Pro
```

```
            245                 250                 255
Glu Val Thr Cys Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Ala Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Lys Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro
                435                 440

<210> SEQ ID NO 34
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 34

Asp Ile Gln Met Thr Gln Ser Pro Ser Ser Leu Pro Ala Ser Leu Gly
1               5                   10                  15

Asp Arg Val Thr Ile Asn Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Asn Lys Leu Ala Asp Gly Val Pro Ser Arg Phe Ser Gly
    50                  55                  60

Ser Gly Ser Gly Arg Asp Ser Phe Thr Ile Ser Ser Leu Glu Ser
65                  70                  75                  80

Glu Asp Ile Gly Ser Tyr Tyr Cys Gln Gln Tyr Tyr Asn Tyr Pro Trp
                85                  90                  95

Thr Phe Gly Pro Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 35
<211> LENGTH: 20
<212> TYPE: DNA
<213> ORGANISM: Artificial Sequence
<220> FEATURE:
<223> OTHER INFORMATION: an artificially synthesized sequence

<400> SEQUENCE: 35
tatcagagct tggttgacgg                                              20

<210> SEQ ID NO 36
<211> LENGTH: 32
<212> TYPE: DNA
<213> ORGANISM: Artificial Sequence
<220> FEATURE:
<223> OTHER INFORMATION: an artificially synthesized sequence

<400> SEQUENCE: 36
actcgttgtg gcttagaagc agtaacaata cc                                32

<210> SEQ ID NO 37
<211> LENGTH: 30
<212> TYPE: DNA
<213> ORGANISM: Artificial Sequence
<220> FEATURE:
<223> OTHER INFORMATION: an artificially synthesized sequence

<400> SEQUENCE: 37
actgtaatcc tagtacttag gaggctgagg                                   30

<210> SEQ ID NO 38
<211> LENGTH: 26
<212> TYPE: DNA
<213> ORGANISM: Artificial Sequence
<220> FEATURE:
<223> OTHER INFORMATION: an artificially synthesized sequence

<400> SEQUENCE: 38
aatccatctt gttcaatggc cgatcc                                       26

<210> SEQ ID NO 39
<211> LENGTH: 30
<212> TYPE: DNA
<213> ORGANISM: Artificial Sequence
<220> FEATURE:
<223> OTHER INFORMATION: an artificially synthesized sequence

<400> SEQUENCE: 39
tagcagcctt cagatgaaga ggtaggactc                                   30

<210> SEQ ID NO 40
<211> LENGTH: 28
<212> TYPE: DNA
<213> ORGANISM: Artificial Sequence
<220> FEATURE:
<223> OTHER INFORMATION: an artificially synthesized sequence
```

<400> SEQUENCE: 40
ttgatgtgcc acctcactgc tgcactgg    28

<210> SEQ ID NO 41
<211> LENGTH: 24
<212> TYPE: DNA
<213> ORGANISM: Artificial Sequence
<220> FEATURE:
<223> OTHER INFORMATION: an artificially synthesized sequence

<400> SEQUENCE: 41
aactgacaat gggacatcag ctga    24

<210> SEQ ID NO 42
<211> LENGTH: 24
<212> TYPE: DNA
<213> ORGANISM: Artificial Sequence
<220> FEATURE:
<223> OTHER INFORMATION: an artificially synthesized sequence

<400> SEQUENCE: 42
atgggactgt tactttacta agat    24

<210> SEQ ID NO 43
<211> LENGTH: 28
<212> TYPE: DNA
<213> ORGANISM: Artificial Sequence
<220> FEATURE:
<223> OTHER INFORMATION: an artificially synthesized sequence

<400> SEQUENCE: 43
aagaaatggg tggtattaca cagacacc    28

<210> SEQ ID NO 44
<211> LENGTH: 31
<212> TYPE: DNA
<213> ORGANISM: Artificial Sequence
<220> FEATURE:
<223> OTHER INFORMATION: an artificially synthesized sequence

<400> SEQUENCE: 44
tgggccagcg ggaggcagtg ttctccagag g    31

<210> SEQ ID NO 45
<211> LENGTH: 29
<212> TYPE: DNA
<213> ORGANISM: Artificial Sequence
<220> FEATURE:
<223> OTHER INFORMATION: an artificially synthesized sequence

<400> SEQUENCE: 45
tagttcggtg acctggcttt atctactgg    29

<210> SEQ ID NO 46
<211> LENGTH: 31
<212> TYPE: DNA
<213> ORGANISM: Artificial Sequence
<220> FEATURE:
<223> OTHER INFORMATION: an artificially synthesized sequence

<400> SEQUENCE: 46
atggctgctt ctagaagcca ccagtctcag g    31

<210> SEQ ID NO 47
<211> LENGTH: 26

```
<212> TYPE: DNA
<213> ORGANISM: Artificial Sequence
<220> FEATURE:
<223> OTHER INFORMATION: an artificially synthesized sequence

<400> SEQUENCE: 47
tgctccacgc ttttgccgga ggacag                                    26

<210> SEQ ID NO 48
<211> LENGTH: 25
<212> TYPE: DNA
<213> ORGANISM: Artificial Sequence
<220> FEATURE:
<223> OTHER INFORMATION: an artificially synthesized sequence

<400> SEQUENCE: 48
taggaggaga acacctggac tactc                                     25

<210> SEQ ID NO 49
<211> LENGTH: 28
<212> TYPE: DNA
<213> ORGANISM: Artificial Sequence
<220> FEATURE:
<223> OTHER INFORMATION: an artificially synthesized sequence

<400> SEQUENCE: 49
agcattctga gaggatgcgg tggaacac                                  28

<210> SEQ ID NO 50
<211> LENGTH: 29
<212> TYPE: DNA
<213> ORGANISM: Artificial Sequence
<220> FEATURE:
<223> OTHER INFORMATION: an artificially synthesized sequence

<400> SEQUENCE: 50
tgctcggagg gctggatctg ggtccacag                                 29

<210> SEQ ID NO 51
<211> LENGTH: 29
<212> TYPE: DNA
<213> ORGANISM: Artificial Sequence
<220> FEATURE:
<223> OTHER INFORMATION: an artificially synthesized sequence

<400> SEQUENCE: 51
tcatcctgtg gcttgcctct atttgttgc                                 29

<210> SEQ ID NO 52
<211> LENGTH: 29
<212> TYPE: DNA
<213> ORGANISM: Artificial Sequence
<220> FEATURE:
<223> OTHER INFORMATION: an artificially synthesized sequence

<400> SEQUENCE: 52
ttgctatggc actttgagaa acctccatc                                 29

<210> SEQ ID NO 53
<211> LENGTH: 26
<212> TYPE: DNA
<213> ORGANISM: Artificial Sequence
<220> FEATURE:
<223> OTHER INFORMATION: an artificially synthesized sequence

<400> SEQUENCE: 53
```
aatacttcta ctggagaagc aaagag                                                                         26

<210> SEQ ID NO 54
<211> LENGTH: 27
<212> TYPE: DNA
<213> ORGANISM: Artificial Sequence
<220> FEATURE:
<223> OTHER INFORMATION: an artificially synthesized sequence

<400> SEQUENCE: 54
tagttgcatt tagaggactt attatgc                                                                        27

<210> SEQ ID NO 55
<211> LENGTH: 360
<212> TYPE: DNA
<213> ORGANISM: Artificial Sequence
<220> FEATURE:
<223> OTHER INFORMATION: an artificially synthesized sequence
<220> FEATURE:
<221> NAME/KEY: CDS
<222> LOCATION: (1)..(360)

<400> SEQUENCE: 55

```
gaa gtg cag ctg gtc gag agc ggg ggg ggg ctg gtg cag cca gga gga     48
Glu Val Gln Leu Val Glu Ser Gly Gly Gly Leu Val Gln Pro Gly Gly
1               5                   10                  15 tct ctg agg ctg agt tgc gcc gct tca ggc ttc aac atc aag gac act     96
Ser Leu Arg Leu Ser Cys Ala Ala Ser Gly Phe Asn Ile Lys Asp Thr
            20                  25                  30 tac att cac tgg gtg cga cag gca cca ggg aaa gga ctg gag tgg gtc    144
Tyr Ile His Trp Val Arg Gln Ala Pro Gly Lys Gly Leu Glu Trp Val
        35                  40                  45 gcc cgg atc tat ccc aca aat gga tac act cgg tat gcc gac tcc gtg    192
Ala Arg Ile Tyr Pro Thr Asn Gly Tyr Thr Arg Tyr Ala Asp Ser Val
    50                  55                  60 aag ggc aga ttc acc att agc gcc gat acc tcc aaa aac aca gct tac    240
Lys Gly Arg Phe Thr Ile Ser Ala Asp Thr Ser Lys Asn Thr Ala Tyr
65                  70                  75                  80 ctg cag atg aac agc ctg agg gct gaa gat aca gca gtg tac tat tgc    288
Leu Gln Met Asn Ser Leu Arg Ala Glu Asp Thr Ala Val Tyr Tyr Cys
                85                  90                  95 tct cgc tgg gga ggc gac ggc ttt tac gca atg gat tat tgg ggc cag    336
Ser Arg Trp Gly Gly Asp Gly Phe Tyr Ala Met Asp Tyr Trp Gly Gln
            100                 105                 110 ggg act ctg gtg acc gtc agc tcc                                    360
Gly Thr Leu Val Thr Val Ser Ser
        115                 120
```

<210> SEQ ID NO 56
<211> LENGTH: 120
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 57
<211> LENGTH: 321
<212> TYPE: DNA
<213> ORGANISM: Artificial Sequence
<220> FEATURE:
<223> OTHER INFORMATION: an artificially synthesized sequence
<220> FEATURE:
<221> NAME/KEY: CDS
<222> LOCATION: (1)..(321)

<400> SEQUENCE: 57 gac att cag atg act cag agc cct tca agc ctg agt gct tca gtc ggg    48
Asp Ile Gln Met Thr Gln Ser Pro Ser Ser Leu Ser Ala Ser Val Gly
1               5                   10                  15 gac agg gtg aca atc act tgc cgc gca agc cag gat gtc aac acc gct    96
Asp Arg Val Thr Ile Thr Cys Arg Ala Ser Gln Asp Val Asn Thr Ala
            20                  25                  30 gtg gca tgg tac cag cag aag cca ggc aaa gca ccc aag ctg ctg atc   144
Val Ala Trp Tyr Gln Gln Lys Pro Gly Lys Ala Pro Lys Leu Leu Ile
        35                  40                  45 tac agc gcc tcc ttc ctg tat tcc ggg gtg cca tct cgg ttt tct ggc   192
Tyr Ser Ala Ser Phe Leu Tyr Ser Gly Val Pro Ser Arg Phe Ser Gly
    50                  55                  60 agt aga tca ggg acc gac ttc acc ctg aca atc agc tcc ctg cag ccc   240
Ser Arg Ser Gly Thr Asp Phe Thr Leu Thr Ile Ser Ser Leu Gln Pro
65                  70                  75                  80 gaa gat ttt gcc aca tac tat tgc cag cag cac tac acc aca ccc cct   288
Glu Asp Phe Ala Thr Tyr Tyr Cys Gln Gln His Tyr Thr Thr Pro Pro
                85                  90                  95 aca ttc ggg cag gga act aaa gtg gag att aag                       321
Thr Phe Gly Gln Gly Thr Lys Val Glu Ile Lys
            100                 105

<210> SEQ ID NO 58
<211> LENGTH: 107
<212> TYPE: PRT
<213> ORGANISM: Artificial Sequence
<220> FEATURE:
<223> OTHER INFORMATION: Synthetic Construct

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 59
<211> LENGTH: 321
<212> TYPE: DNA
<213> ORGANISM: Artificial Sequence
<220> FEATURE:
<223> OTHER INFORMATION: an artificially synthesized sequence
<220> FEATURE:
<221> NAME/KEY: CDS
<222> LOCATION: (1)..(321)

<400> SEQUENCE: 59 gat att cag atg act cag agc cct tct tca ctg agt gca tca gtg ggc    48
Asp Ile Gln Met Thr Gln Ser Pro Ser Ser Leu Ser Ala Ser Val Gly
1               5                   10                  15 gac cga gtc acc atc aca tgc cgg gcc agc cag gat att aga aac tac    96
Asp Arg Val Thr Ile Thr Cys Arg Ala Ser Gln Asp Ile Arg Asn Tyr
            20                  25                  30 ctg aat tgg tat cag cag aag cct ggc aaa gct cca aag ctg ctg atc   144
Leu Asn Trp Tyr Gln Gln Lys Pro Gly Lys Ala Pro Lys Leu Leu Ile
        35                  40                  45 tac tat acc tct agg ctg gag agt gga gtg cca tca cgc ttc agc gga   192
Tyr Tyr Thr Ser Arg Leu Glu Ser Gly Val Pro Ser Arg Phe Ser Gly
    50                  55                  60 tcc gga tct ggg acc gac tac act ctg acc att agc tcc ctg cag cca   240
Ser Gly Ser Gly Thr Asp Tyr Thr Leu Thr Ile Ser Ser Leu Gln Pro
65                  70                  75                  80 gaa gat ttc gcc aca tac tat tgt cag cag gga aac act ctg ccc tgg   288
Glu Asp Phe Ala Thr Tyr Tyr Cys Gln Gln Gly Asn Thr Leu Pro Trp
                85                  90                  95 acc ttt gga cag ggc acc aaa gtg gag atc aag                       321
Thr Phe Gly Gln Gly Thr Lys Val Glu Ile Lys
            100                 105

<210> SEQ ID NO 60
<211> LENGTH: 107
<212> TYPE: PRT
<213> ORGANISM: Artificial Sequence
<220> FEATURE:
<223> OTHER INFORMATION: Synthetic Construct

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 61
<211> LENGTH: 366
<212> TYPE: DNA
<213> ORGANISM: Artificial Sequence
<220> FEATURE:
<223> OTHER INFORMATION: an artificially synthesized sequence
<220> FEATURE:
<221> NAME/KEY: CDS
<222> LOCATION: (1)..(366)

<400> SEQUENCE: 61

```
gag gtg cag ctg gtc gaa tcc gga gga gga ctg gtg cag cca gga gga      48
Glu Val Gln Leu Val Glu Ser Gly Gly Gly Leu Val Gln Pro Gly Gly
1               5                   10                  15 agc ctg cga ctg tcc tgc gcc gct agc gga tac tcc ttt aca ggc tat      96
Ser Leu Arg Leu Ser Cys Ala Ala Ser Gly Tyr Ser Phe Thr Gly Tyr
            20                  25                  30 act atg aat tgg gtg cga cag gct ccc ggg aaa gga ctg gag tgg gtg     144
Thr Met Asn Trp Val Arg Gln Ala Pro Gly Lys Gly Leu Glu Trp Val
        35                  40                  45 gca ctg atc aac cct tac aag ggc gtc agt acc tat aat cag aag ttc     192
Ala Leu Ile Asn Pro Tyr Lys Gly Val Ser Thr Tyr Asn Gln Lys Phe
    50                  55                  60 aaa gac cgg ttc acc att tct gtg gat aag agt aaa aac acc gct tac     240
Lys Asp Arg Phe Thr Ile Ser Val Asp Lys Ser Lys Asn Thr Ala Tyr
65                  70                  75                  80 ctg cag atg aat agc ctg aga gca gag gac aca gcc gtg tac tat tgc     288
Leu Gln Met Asn Ser Leu Arg Ala Glu Asp Thr Ala Val Tyr Tyr Cys
                85                  90                  95 gca agg agt ggc tac tat ggg gac tca gat tgg tat ttc gac gtg tgg     336
Ala Arg Ser Gly Tyr Tyr Gly Asp Ser Asp Trp Tyr Phe Asp Val Trp
            100                 105                 110 gga cag ggg acc ctg gtg aca gtc tct agt                             366
Gly Gln Gly Thr Leu Val Thr Val Ser Ser
        115                 120
```

<210> SEQ ID NO 62
<211> LENGTH: 122
<212> TYPE: PRT
<213> ORGANISM: Artificial Sequence
<220> FEATURE:
<223> OTHER INFORMATION: Synthetic Construct

<400> SEQUENCE: 62

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120
```

-continued

<210> SEQ ID NO 63
<211> LENGTH: 118
<212> TYPE: PRT
<213> ORGANISM: Artificial Sequence
<220> FEATURE:
<223> OTHER INFORMATION: an artificially synthesized sequence

<400> SEQUENCE: 63

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 64
<211> LENGTH: 108
<212> TYPE: PRT
<213> ORGANISM: Artificial Sequence
<220> FEATURE:
<223> OTHER INFORMATION: an artificially synthesized sequence

<400> SEQUENCE: 64

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Phe Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 65
<211> LENGTH: 324
<212> TYPE: PRT
<213> ORGANISM: Artificial Sequence
<220> FEATURE:
<223> OTHER INFORMATION: an artificially synthesized sequence

<400> SEQUENCE: 65

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr

```
            20                  25                  30
Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Lys
            100                 105                 110

Glu Val Ser Lys Val Phe Ile Phe Pro Pro Lys Pro Lys Asp Val Leu
            115                 120                 125

Thr Ile Thr Leu Thr Pro Lys Val Thr Cys Val Val Asp Ile Ser
        130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
            210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Glu Leu Asn
            275                 280                 285

Val Gln Lys Ser Asn Trp Glu Ala Gly Asn Thr Phe Thr Cys Ser Val
            290                 295                 300

Leu His Glu Gly Leu His Asn His His Thr Glu Lys Ser Leu Ser His
305                 310                 315                 320

Ser Pro Gly Lys

<210> SEQ ID NO 66
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 66

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
            35                  40                  45

Gln Asn Gly Val Leu Asn Ser Trp Thr Asp Gln Asp Ser Lys Asp Ser
        50                  55                  60
```

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 67
<211> LENGTH: 122
<212> TYPE: PRT
<213> ORGANISM: Artificial Sequence
<220> FEATURE:
<223> OTHER INFORMATION: an artificially synthesized sequence

<400> SEQUENCE: 67

Gln Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Ser Asn Ala
                20                  25                  30

Trp Met His Val Arg Gln Ala Pro Gly Lys Gly Leu Glu Trp Val
            35                  40                  45

Ala Gln Ile Lys Asp Lys Ser Gln Asn Tyr Ala Thr Tyr Val Ala Glu
    50                  55                  60

Ser Val Lys Gly Arg Phe Thr Ile Ser Arg Ala Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Ala Ala Gly Tyr Gly Val Asp Ile Trp
            100                 105                 110

Gly Gln Gly Thr Thr Val Thr Val Ser Ser
        115                 120

<210> SEQ ID NO 68
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 68

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Pro Leu Val His Ser
                20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Val Pro Tyr Thr Phe Gly Gln Gly Thr Lys Leu Glu Ile Lys
            100                 105                 110

<210> SEQ ID NO 69
<211> LENGTH: 324
<212> TYPE: PRT

<213> ORGANISM: Artificial Sequence
<220> FEATURE:
<223> OTHER INFORMATION: an artificially synthesized sequence

<400> SEQUENCE: 69

| | | | | | | | | | | | | | | |
|---|---|---|---|---|---|---|---|---|---|---|---|---|---|---|
| Ala | Lys | Thr | Thr | Pro | Pro | Ser | Val | Tyr | Pro | Leu | Ala | Pro | Gly | Ser | Ala |
| 1 | | | | 5 | | | | | 10 | | | | | 15 | |
| Ala | Gln | Thr | Asn | Ser | Met | Val | Thr | Leu | Gly | Cys | Leu | Val | Lys | Gly | Tyr |
| | | | 20 | | | | | 25 | | | | | 30 | | |
| Phe | Pro | Glu | Pro | Val | Thr | Val | Thr | Trp | Asn | Ser | Gly | Ser | Leu | Ser | Ser |
| | | 35 | | | | | 40 | | | | | 45 | | | |
| Gly | Val | His | Thr | Phe | Pro | Ala | Val | Leu | Gln | Ser | Asp | Leu | Tyr | Thr | Leu |
| | 50 | | | | | 55 | | | | | 60 | | | | |
| Ser | Ser | Ser | Val | Thr | Val | Pro | Ser | Ser | Thr | Trp | Pro | Ser | Glu | Thr | Val |
| 65 | | | | | 70 | | | | | 75 | | | | | 80 |
| Thr | Cys | Asn | Val | Ala | His | Pro | Ala | Ser | Ser | Thr | Lys | Val | Asp | Lys | Lys |
| | | | | 85 | | | | | 90 | | | | | 95 | |
| Ile | Val | Pro | Arg | Asp | Cys | Gly | Cys | Lys | Pro | Cys | Ile | Cys | Thr | Val | Lys |
| | | | 100 | | | | | 105 | | | | | 110 | | |
| Glu | Val | Ser | Lys | Val | Phe | Ile | Phe | Pro | Pro | Lys | Pro | Lys | Asp | Val | Leu |
| | | | 115 | | | | | 120 | | | | | 125 | | |
| Thr | Ile | Thr | Leu | Thr | Pro | Lys | Val | Thr | Cys | Val | Val | Val | Asp | Ile | Ser |
| | | | 130 | | | | | 135 | | | | | 140 | | |
| Lys | Asp | Asp | Pro | Glu | Val | Gln | Phe | Ser | Trp | Phe | Val | Asp | Asp | Val | Glu |
| 145 | | | | | 150 | | | | | 155 | | | | | 160 |
| Val | His | Thr | Ala | Gln | Thr | Gln | Pro | Arg | Glu | Glu | Gln | Phe | Asn | Ser | Thr |
| | | | | 165 | | | | | 170 | | | | | 175 | |
| Phe | Arg | Ser | Val | Ser | Glu | Leu | Pro | Ile | Met | His | Gln | Asp | Trp | Leu | Asn |
| | | | 180 | | | | | 185 | | | | | 190 | | |
| Gly | Lys | Glu | Phe | Lys | Cys | Arg | Val | Asn | Ser | Ala | Ala | Phe | Pro | Ala | Pro |
| | | | 195 | | | | | 200 | | | | | 205 | | |
| Ile | Glu | Lys | Thr | Ile | Ser | Lys | Thr | Lys | Gly | Arg | Pro | Lys | Ala | Pro | Gln |
| | | | 210 | | | | | 215 | | | | | 220 | | |
| Val | Tyr | Thr | Ile | Pro | Pro | Pro | Lys | Glu | Gln | Met | Ala | Lys | Asp | Lys | Val |
| 225 | | | | | 230 | | | | | 235 | | | | | 240 |
| Ser | Leu | Thr | Cys | Met | Ile | Thr | Asp | Phe | Phe | Pro | Glu | Asp | Ile | Thr | Val |
| | | | | 245 | | | | | 250 | | | | | 255 | |
| Glu | Trp | Gln | Trp | Asn | Gly | Gln | Pro | Ala | Glu | Asn | Tyr | Lys | Asn | Thr | Gln |
| | | | 260 | | | | | 265 | | | | | 270 | | |
| Pro | Ile | Met | Arg | Thr | Asp | Gly | Ser | Tyr | Phe | Val | Tyr | Ser | Lys | Leu | Asn |
| | | | 275 | | | | | 280 | | | | | 285 | | |
| Val | Gln | Lys | Ser | Asn | Trp | Glu | Ala | Gly | Asn | Thr | Phe | Thr | Cys | Ser | Val |
| | 290 | | | | | 295 | | | | | 300 | | | | |
| Leu | His | Glu | Gly | Leu | His | Asn | His | His | Thr | Glu | Lys | Ser | Leu | Ser | His |
| 305 | | | | | 310 | | | | | 315 | | | | | 320 |
| Ser | Pro | Gly | Lys | | | | | | | | | | | | |

<210> SEQ ID NO 70
<211> LENGTH: 325
<212> TYPE: PRT
<213> ORGANISM: Artificial Sequence
<220> FEATURE:
<223> OTHER INFORMATION: An artificially generated sequence

<400> SEQUENCE: 70

Ala Ser Thr Lys Gly Pro Ser Val Phe Pro Leu Ala Pro Cys Ser Arg

```
               1               5                  10                 15
         Ser Thr Ser Glu Ser Thr Ala Ala Leu Gly Cys Leu Val Lys Asp Tyr
                          20                  25                 30

Phe Pro Glu Pro Val Thr Val Ser Trp Asn Ser Gly Ala Leu Thr Ser
                          35                  40                 45

Gly Val His Thr Phe Pro Ala Val Leu Gln Ser Ser Gly Leu Tyr Ser
                          50                  55                 60

Leu Ser Ser Val Val Thr Val Pro Ser Ser Leu Gly Thr Lys Thr
          65                  70                  75                 80

Tyr Thr Cys Asn Val Asp His Lys Pro Ser Asn Thr Lys Val Asp Lys
                          85                  90                 95

Arg Val Glu Ser Lys Tyr Gly Pro Pro Cys Pro Pro Cys Pro Ala Pro
                          100                 105                110

Glu Phe Arg Gly Gly Pro Lys Val Phe Leu Phe Pro Pro Lys Pro Lys
                          115                 120                125

Asp Thr Leu Met Ile Ser Arg Thr Pro Glu Val Thr Cys Val Val Val
          130                 135                 140

Asp Val Ser Gln Glu Asp Pro Glu Val Gln Phe Asn Trp Tyr Val Asp
          145                 150                 155                160

Gly Val Glu Val His Asn Ala Lys Thr Lys Pro Arg Glu Glu Gln Phe
                          165                 170                175

Ala Ser Thr Tyr Arg Val Val Ser Val Leu Thr Val Leu His Gln Asp
                          180                 185                190

Trp Leu Asn Gly Lys Glu Tyr Lys Cys Lys Val Ser Asn Lys Gly Leu
                          195                 200                205

Pro Ser Ser Ile Glu Lys Thr Ile Ser Lys Ala Lys Gly Gln Pro Arg
          210                 215                 220

Glu Pro Gln Val Tyr Thr Leu Pro Pro Ser Gln Lys Glu Met Thr Lys
          225                 230                 235                240

Asn Gln Val Ser Leu Thr Cys Leu Val Lys Gly Phe Tyr Pro Ser Asp
                          245                 250                255

Ile Ala Val Glu Trp Glu Ser Asn Gly Gln Pro Glu Asn Asn Tyr Lys
                          260                 265                270

Thr Thr Pro Pro Val Leu Asp Ser Asp Gly Ser Phe Phe Leu Tyr Ser
                          275                 280                285

Lys Leu Thr Val Asp Lys Ser Arg Trp Gln Glu Gly Asn Val Phe Ser
                          290                 295                300

Cys Ser Val Met His Glu Ala Leu His Asn His Tyr Thr Gln Lys Ser
          305                 310                 315                320

Leu Ser Leu Ser Pro
                          325

<210> SEQ ID NO 71
<211> LENGTH: 115
<212> TYPE: PRT
<213> ORGANISM: Artificial Sequence
<220> FEATURE:
<223> OTHER INFORMATION: An artificially generated sequence

<400> SEQUENCE: 71

Gln Val Gln Leu Val Gln Ser Gly Ala Glu Val Lys Lys Pro Gly Ala
 1               5                  10                 15

Ser Val Thr Val Ser Cys Lys Ala Ser Gly Tyr Thr Phe Thr Asp Tyr
                 20                  25                 30

Glu Met His Trp Ile Arg Gln Pro Pro Gly Glu Gly Leu Glu Trp Ile
```

```
            35                  40                  45
Gly Ala Ile Asp Gly Pro Thr Pro Asp Thr Ala Tyr Ser Glu Lys Phe
     50                  55                  60

Lys Gly Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                 85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 72
<211> LENGTH: 325
<212> TYPE: PRT
<213> ORGANISM: Artificial Sequence
<220> FEATURE:
<223> OTHER INFORMATION: An artificially generated sequence

<400> SEQUENCE: 72

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Arg Gly Gly Pro Lys Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Ala Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
```

```
                275                 280                 285
Lys Leu Thr Val Asp Lys Ser Arg Trp Gln Glu Gly Asn Val Phe Ser
            290                 295                 300

Cys Ser Val Met His Glu Ala Leu His Asn His Tyr Thr Gln Glu Ser
305                 310                 315                 320

Leu Ser Leu Ser Pro
            325

<210> SEQ ID NO 73
<211> LENGTH: 112
<212> TYPE: PRT
<213> ORGANISM: Artificial Sequence
<220> FEATURE:
<223> OTHER INFORMATION: An artificially generated sequence

<400> SEQUENCE: 73

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Pro Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Val Pro Tyr Thr Phe Gly Gln Gly Thr Lys Leu Glu Ile Lys
            100                 105                 110

<210> SEQ ID NO 74
<211> LENGTH: 107
<212> TYPE: PRT
<213> ORGANISM: Artificial Sequence
<220> FEATURE:
<223> OTHER INFORMATION: An artificially generated sequence

<400> SEQUENCE: 74

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```